(12) United States Patent
Callewaert et al.

(10) Patent No.: US 11,421,209 B2
(45) Date of Patent: Aug. 23, 2022

(54) CELLS PRODUCING FC CONTAINING MOLECULES HAVING ALTERED GLYCOSYLATION PATTERNS AND METHODS AND USE THEREOF

(71) Applicants: VIB VZW, Ghent (BE); Universiteit Gent, Ghent (BE)

(72) Inventors: Nico L. M. Callewaert, Nevele (BE); Francis Santens, Ghent (BE)

(73) Assignees: VIB VZW, Ghent (BE); Universiteit Gent, Ghent (BE)

(*) Notice: Subject to any disclaimer, the term of this patent is extended or adjusted under 35 U.S.C. 154(b) by 112 days.

(21) Appl. No.: 16/153,257

(22) Filed: Oct. 5, 2018

(65) Prior Publication Data
US 2019/0024066 A1 Jan. 24, 2019

Related U.S. Application Data

(62) Division of application No. 14/917,248, filed as application No. PCT/EP2014/068946 on Sep. 5, 2014, now Pat. No. 10,202,590.

(30) Foreign Application Priority Data

Sep. 5, 2013 (EP) .................................. 13183124

(51) Int. Cl.
*A61K 39/395* (2006.01)
*C12N 9/24* (2006.01)
*C12P 21/00* (2006.01)
*C07K 16/28* (2006.01)

(52) U.S. Cl.
CPC ........ *C12N 9/2402* (2013.01); *C07K 16/2887* (2013.01); *C12P 21/005* (2013.01); *C12Y 302/01096* (2013.01); *C07K 2317/41* (2013.01); *C07K 2317/71* (2013.01); *C07K 2317/732* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,721,121 A | 2/1998 | Etcheverry et al. |
| 2009/0069232 A1 | 3/2009 | Callewaert et al. |
| 2011/0191913 A1 | 8/2011 | Callewaert et al. |
| 2011/0201540 A1 | 8/2011 | Callewaert et al. |
| 2011/0207676 A1 | 8/2011 | Callewaert et al. |
| 2011/0263828 A1 | 10/2011 | Wong et al. |
| 2013/0190253 A1 | 7/2013 | Callewaert et al. |
| 2013/0195835 A1 | 8/2013 | Callewaert et al. |
| 2014/0345004 A1 | 11/2014 | Callewaert et al. |

FOREIGN PATENT DOCUMENTS

| | | |
|---|---|---|
| EP | 549062 A2 | 6/1993 |
| EP | 2331701 A1 | 6/2011 |
| WO | WO0200879 A2 | 1/2002 |
| WO | WO0248187 A2 | 6/2002 |
| WO | WO2008120107 A2 | 10/2008 |
| WO | WO2010015722 A1 | 2/2010 |
| WO | WO2013120066 A1 | 8/2013 |
| WO | WO2015032899 A1 | 3/2015 |

OTHER PUBLICATIONS

Kai-Ting C. Shade and Robert M. Anthony. Antibody glycosylation and inflammation. Antibodies. 2, pp. 392-414, Jun. 25, 2013 (Year: 2013).*
Wang W., et al. Antibody structure, instability, and formulation. Journal of Pharmaceutical Sciences. 96(1) 26 pages, Jan. 2007 (Year: 2007).*
Anyaogu et al., Manipulating the glycosylation pathway in bacterial and lower eukaryotes for production of therapeutic protein, Current Opinion in Biotechnology, 2015, pp. 122-128, vol. 36.
Baldwin et al., Develop Systems for Manufacturing 100,000,000 Doses of an Emergency Pharmaceutical (e.g., Vaccine or Monoclonal Antibody) Within 2 Months of Production Identification, Jun. 6, 2006, pp. FP-21.
Dwek, Raymond A., Glycobiology: Toward Understanding the Function of Sugars, Chem. Rev., 1996, pp. 683-720, vol. 96.
PCT International Search Report and Written Opinion, PCT/EP2014/068946, dated Dec. 19, 2014.
Rodriguez et al., High level expression of the B. microplus Bm86 antigen in the yeast *Pichia pastoris* forming highly immunogenic particles for cattle, Journal of Biotechnology, 1994, pp. 135-146, vol. 33.
Chan, Kuan Rong, et al. Fc receptors and their influence on efficacy of therapeutic antibodies for treatment of viral diseases. Expert Reviews, Anti Infect Ther. vol. 13(11), 1351-1360 (2015).
Chen, Xiaoyu, et al. The Effect of Fc Glycan Forms on Human IgG2 Antibody Clearance in Humans. Glycobiology. vol. 19 No. 3, pp. 240-249 (2009).

* cited by examiner

*Primary Examiner* — Michael D Pak
(74) *Attorney, Agent, or Firm* — Patent Law Works, LLP

(57) ABSTRACT

The present application relates to the field of glyco-engineering, more specifically to glyco-engineering of Fc-containing molecules, such as antibodies. It is shown herein that Fc-containing molecules with a specific glycosylation pattern have a considerably longer circulating half-life in vivo, without having an altered binding affinity for their respective antigen. This has therapeutic implications in reducing the frequency with which these molecules need to be administered, without affecting therapeutic efficacy. Also, cells are provided that can produce the Fc molecules with the desired glycosylation pattern.

15 Claims, 22 Drawing Sheets
(20 of 22 Drawing Sheet(s) Filed in Color)
Specification includes a Sequence Listing.

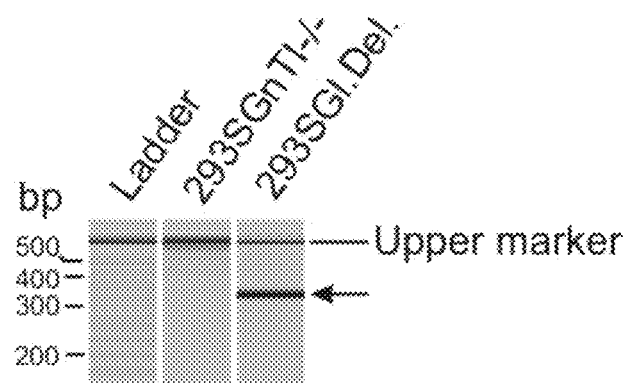
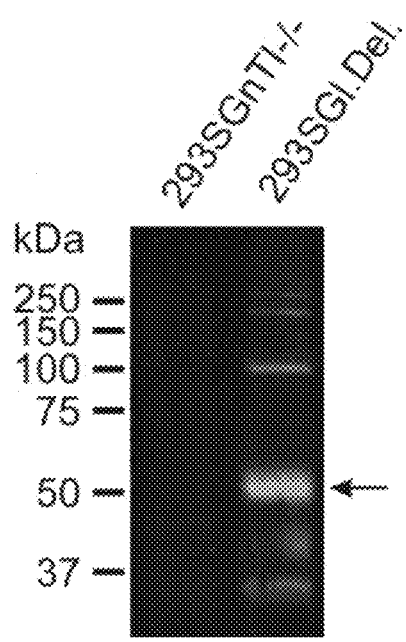
FIG. 5A  FIG. 5B
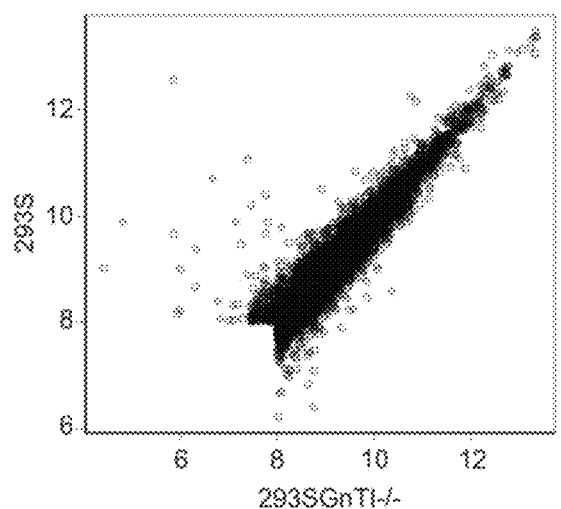
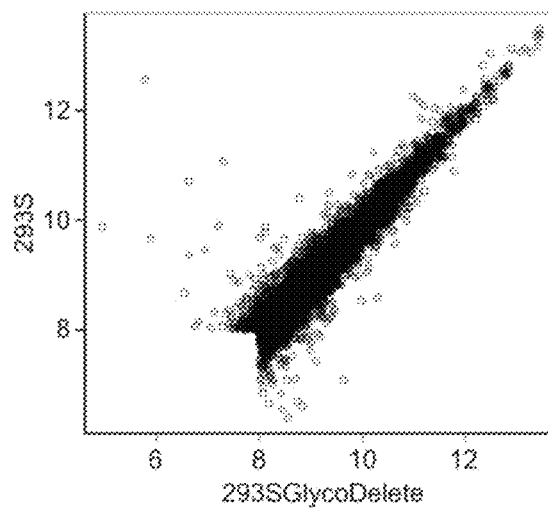
FIG. 6A  FIG. 6B

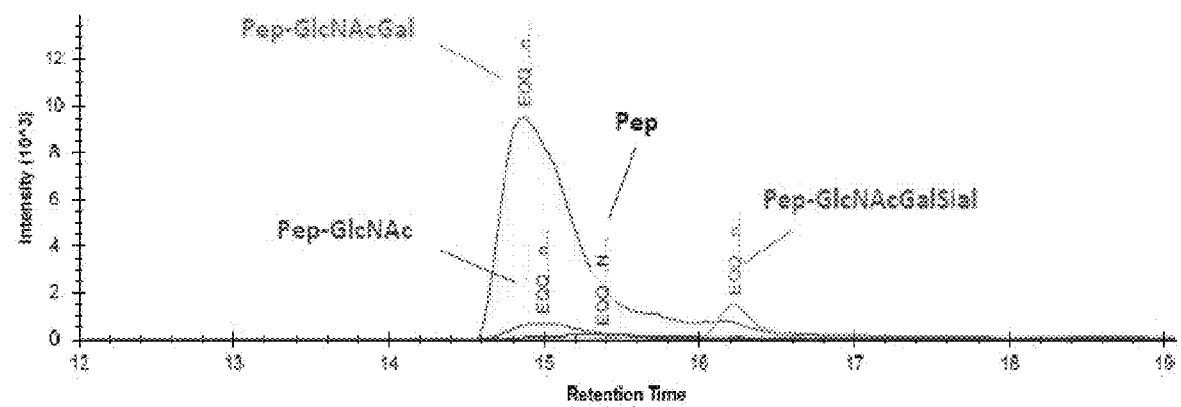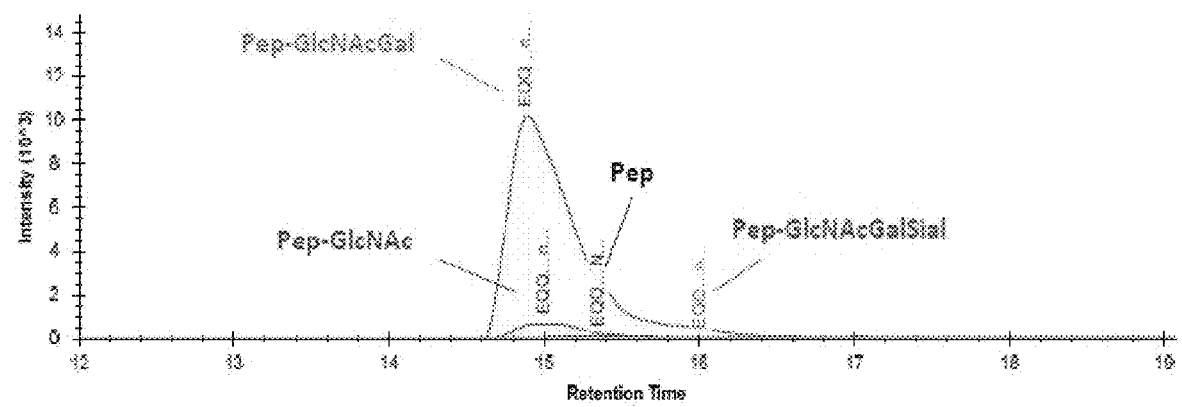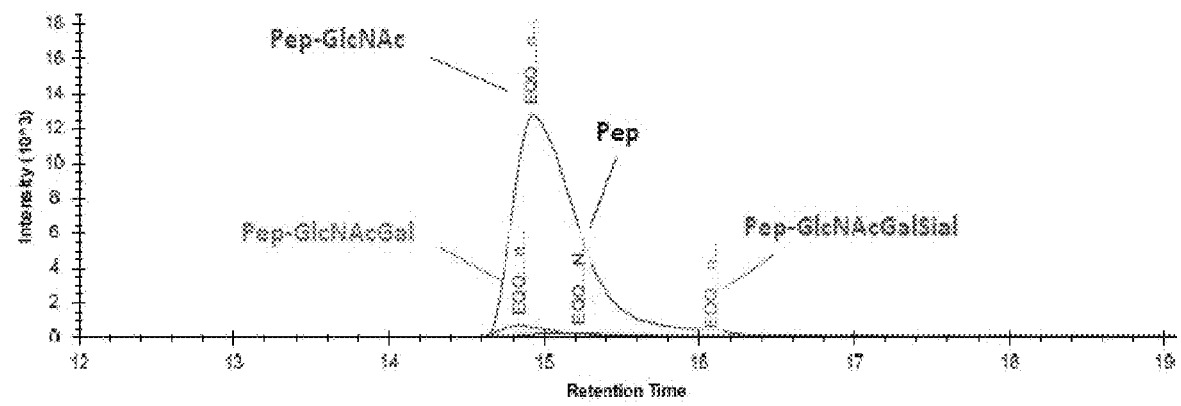
FIG. 18

CELLS PRODUCING FC CONTAINING MOLECULES HAVING ALTERED GLYCOSYLATION PATTERNS AND METHODS AND USE THEREOF

CROSS-REFERENCE TO RELATED APPLICATIONS

This application is a divisional of and claims priority to U.S. application Ser. No. 14/917,248, filed Mar. 7, 2016, which claims priority to a national phase entry under 35 U.S.C. § 371 of International Patent Application PCT/EP2014/068946, filed Sep. 5, 2014, designating the United States of America and published in English as International Patent Publication WO 2015/032899 A1 on Mar. 12, 2015, which claims the benefit under Article 8 of the Patent Cooperation Treaty to European Patent Application Serial No. 13183124.0, filed Sep. 5, 2013.

TECHNICAL FIELD

This application relates to the field of glyco-engineering, more specifically to glyco-engineering of Fc-containing molecules, such as antibodies. It is shown herein that Fc-containing molecules with a specific glycosylation pattern have a considerably longer circulating half-life in vivo, without having an altered binding affinity for their respective antigen. This has therapeutic implications in reducing the frequency with which these molecules need to be administered, without affecting therapeutic efficacy. Also, cells are provided that can produce the Fc molecules with the desired glycosylation pattern.

BACKGROUND

Antibodies, and particularly IgG antibodies, are the basis of some of the most successful therapeutics developed over the last 20 years (e.g., bevacizumab, rituximab, infliximab, adalimumab, trastuzumab, or cetuximab, to name but a few). This success is at least in part attributable to the fact that they are highly specific, have long serum half-lives, and can be produced relatively routinely, making them ideal drugs for immunotherapy. The basic structure of an antibody molecule (or immunoglobulin, Ig) is comprised of two identical heavy and two identical light polypeptide chains. These chains are linked by disulfide bonds forming a "Y"-shaped structure. Human immunoglobulins can be categorized into five classes (IgG, IgA, IgD, IgE, and IgM) referencing the heavy chain. IgG and IgA antibodies are further separated into four (IgG1-4) and two subclasses (IgA1-2), respectively. Recognition of specific antigens is mediated by the antigen-binding fragment (Fab), which includes the variable regions and one constant domain of the light and heavy chains. Effector functions are initiated by binding of the fragment-crystallizable region (Fc), corresponding to the other two domains of the constant region of the heavy chain (CH2 and CH3), to effector proteins such as Fc receptors (FcRs). Thus, the Fab fragments are comprised of variable and constant domains of light and heavy chains, while Fc fragments are comprised entirely of constant domains of heavy chains. This Fc domain prolongs the serum half-life of antibodies due to pH-dependent binding to the neonatal Fc receptor (FcRn), which salvages the protein from being degraded in endosomes.

Given the long serum half-life of antibodies, construction of Fc-fusion proteins has been implemented to prolong the half-life of therapeutic proteins, as most biologically active proteins and peptides have very short serum half-lives due to fast renal clearance, which limits their exposure in the target tissue and, consequently, their pharmacological effects. The Fc-fusion strategy also met with considerable success: marketed Fc-fusion proteins include, e.g., etanercept, alefacept, abatacept, rilonacept, romiplostim, belatacept, and aflibercept. As an additional benefit, the Fc portion of Fc-fusion proteins allows easier expression and protein A-affinity purification, which confers practical advantages in the development of antibody and Fc-fusion therapeutics.

Antibody engineering approaches have been used to further advance the clinical success of therapeutic antibodies, e.g., by altering their binding properties to ligand or Fc receptors, or by further extending their half-life. Typical approaches to achieve this include introducing mutations or altering glycosylation of the antibodies. Introducing mutations in the Fc chain has the inherent drawback of no longer working with natural sequences. Contrary to glycosylation of therapeutic proteins, which is generally accepted to prolong circulating half-life, studies on the effect of glycosylation on the elimination rate of immunoglobulins from circulation have produced conflicting results (Millward et al., 2008), and most studies conclude that glycan structural differences of the Fc moiety do not affect clearance (Chen et al., 2009).

During post-translational modification of the antibody chains, enzymes in the endoplasmic reticulum and Golgi apparatus can attach carbohydrate chains to the polypeptide backbone of the antibody. A single N-linked glycan is present in the Fc portion of all IgG subclasses, at an asparagine at position 297 (Kabat numbering). About 20% of IgG antibodies contain glycans elsewhere on the molecule (Jefferis, 2005). Most recombinant antibody drugs have been engineered or selected to contain only the single Fc glycosylation site.

When the antibody chains are correctly folded and associated, the oligosaccharide at position 297 is sequestered within an internal space enclosed by the CH2 domains, and there are extensive non-covalent interactions between the oligosaccharide and the amino acids of antibody, resulting in reciprocal influences on conformation.

The oligosaccharides found at the conserved Asn-297 site are typically of a fucosylated biantennary complex type. However, among antibody molecules, there may be considerable heterogeneity in the carbohydrate structures (glycoforms) due to altered branching, chain length and/or altered number of carbohydrate moieties. Indeed, the structure of the attached N-linked oligosaccharides varies considerably, depending on the degree of processing, and can include high-mannose, as well as complex biantennary oligosaccharides with or without bisecting GlcNAc and core Fucose residues (Wright and Morrison, 1997). Typically, there is heterogeneous processing of the core oligosaccharide structures attached at a given glycosylation site, with the result that even monoclonal antibodies exist as multiple glycoforms. Moreover, major differences in antibody glycosylation occur between antibody-producing cell lines, and even minor differences are seen for a given cell line grown under different culture conditions.

Indeed, each step in mammalian N-glycan biosynthesis (FIG. 1A, top) is <100% efficient, and some enzymes compete for substrates, resulting in many different glycoforms. Heterogeneous glycosylation presents problems in the production of therapeutic proteins. For example, glycans can affect pharmacokinetics and biological activities (Ferrara et al., 2006; Elliott et al., 2004); however, N-glycans are often crucial for protein folding, so these difficulties cannot be overcome by completely removing N-glycosylation sites or interfering with glycosylation before or in the endoplasmic reticulum.

The differences in glycoforms may result in different or inconsistent effector functions, which can render the antibodies difficult to use therapeutically or define from a regulatory point of view. Also, glycoforms that are not commonly biosynthesized in humans may be allergenic, immunogenic and accelerate the plasmatic clearance of the linked antibody. Deglycosylating the Fc moiety at position 297 can result in decreased or eliminated effector functions of the Fc-containing molecules, or in reduced stability (Krapp et al., 2003; Yamaguchi et al., 2006; Barb et al., 2011; Buck et al., 2013).

It would be advantageous to obtain Fc-containing molecules that have improved properties, such as longer circulating half-life, but without drawbacks such as heterogeneous glycosylation or reduced antigen binding.

BRIEF SUMMARY

Provided are ways of producing antibodies and Fc-fusion proteins that have a prolonged half-life in circulation. Also provided are antibodies and Fc-fusion proteins with a much less heterogeneous glycosylation profile than obtained in normal mammalian cells.

Upon establishing an animal cell line that was glyco-engineered to yield glycoproteins with very specific simple glycans, it was surprisingly found that Fc-containing molecules produced in this cell line have a much longer circulation time in vivo. As the antibodies were otherwise identical to that produced in non-glyco-engineered cells, the difference is solely attributable to the specific glycosylation pattern.

Accordingly, in a first aspect, cells are provided that contain:
  a first exogenous nucleic acid sequence encoding an endoglucosaminidase enzyme;
  a second exogenous nucleic acid sequence encoding an Fc-containing molecule.

It is particularly envisaged that the cells are higher eukaryotic cells. According to further specific embodiments, the higher eukaryotic cells are vertebrate cells, in particular, mammalian cells. Examples include, but are not limited to, CHO cells or HEK293 cells (e.g., HEK293S cells). According to particular embodiments, the Fc part of the Fc-containing molecule is an Fc of an IgG-type molecule.

According to particular embodiments, the glycosyltransferase GnTI, encoded by the gene MGAT1, is inactivated in the cells.

According to specific embodiments, the expression of the endoglucosaminidase enzyme is targeted to the Golgi apparatus. This can be achieved, e.g., by operably linking the endoglucosaminidase to a Golgi localization signal.

According to particular embodiments, the endoglucosaminidase enzyme is a mannosyl-glycoprotein endo-beta-N-acetylglucosaminidase (E.C. 3.2.1.96). Different such enzymes exist, e.g., Endo T, Endo H, Endo S, ENGase. A particularly envisaged enzyme is Endo T.

According to a further aspect, Fc-containing molecules are provided that are obtainable by producing them in these cells, i.e., Fc-containing molecules produced in higher eukaryotic cells characterized by the presence of:
  a first exogenous nucleic acid sequence encoding an endoglucosaminidase enzyme;
  a second exogenous nucleic acid sequence encoding the Fc-containing molecule.

Producing Fc-containing molecules in these cells will lead to molecules with a specific glycosylation pattern. Accordingly, Fc-containing molecules are provided, characterized in that the glycosylation on the Fc part consists of a glycan selected from the following: a trisaccharide structure Neu5Ac-Hex-HexNAc, a disaccharide structure Hex-HexNAc, and a monosaccharide structure HexNAc. According to very specific embodiments, the glycan is selected from the trisaccharide structure and the disaccharide structure (i.e., is not a structure existing of a single HexNAc, such as a single GlcNAc).

Most particularly, the glycosylation on the Fc part is glycosylation on residue N297 of the Fc part. This is a conserved residue in the Fc moiety of IgG-like molecules.

As Fc molecules with a single glycosylation site typically have one glycan chain only, also provided is a plurality of identical Fc-containing molecules, characterized in that the glycosylation (e.g., the glycosylation on N297) of the Fc part consists of one or more glycans selected from the following: a trisaccharide structure Neu5Ac-Hex-HexNAc, a disaccharide structure Hex-HexNAc, and a monosaccharide structure HexNAc. According to particular embodiments, at least one of the plurality of Fc-containing molecules has a glycan selected from the trisaccharide structure and the disaccharide structure; i.e., at least one of the plurality of Fc-containing molecules has a glycan that is not a monosaccharide structure HexNAc.

According to further particular embodiments, the glycans on the Fc-containing molecule or of the plurality of Fc-containing molecules are selected from the trisaccharide structure Neu5Ac-α-2,3-Gal-β-1,4-GlcNAc, the disaccharide structure Gal-β-1,4-GlcNAc, and the monosaccharide structure GlcNAc.

According to particular embodiments, the Fc-containing molecule with the specific glycosylation is an antibody, in particular an IgG.

According to a further aspect, the Fc-containing molecules described herein are provided for use as a medicament. For instance, the Fc-containing molecules may be provided for use in intravenous immunoglobulin therapy. This is equivalent as saying that methods of treating a subject with intravenous immunoglobulin therapy are provided, comprising administering to the subject an Fc-containing molecule produced by the cells described herein. Or alternatively, methods of treating a subject with intravenous immunoglobulin therapy are provided, comprising administering to the subject an Fc-containing molecule (or a plurality of Fc-containing molecules), characterized in that the glycosylation on the Fc part consists of a glycan selected from the following: a trisaccharide structure Neu5Ac-Hex-HexNAc, a disaccharide structure Hex-HexNAc, and a monosaccharide structure HexNAc.

According to yet further aspects, methods for producing Fc-containing molecules with a specific glycosylation pattern on residue N297 in a higher eukaryotic cell are provided, comprising the steps of:
  providing a higher eukaryotic cell comprising a first exogenous nucleic acid sequence encoding an endoglucosaminidase enzyme, wherein the endoglucosaminidase is operably linked to a Golgi localization signal, and a second exogenous nucleic acid sequence encoding the Fc-containing molecule, in conditions suitable for expressing the endoglucosaminidase enzyme and the Fc-containing molecule; and
  recovering the Fc-containing molecule after it has been intracellularly contacted with the endoglucosaminidase.

According to specific embodiments, the Fc-containing molecules that are produced are secreted.

It is a particular advantage that the Fc-containing molecules with specific glycosylation patterns have a longer circulating half-life; i.e., they remain longer in circulation, are cleared less efficiently, or maintain a certain threshold concentration for a longer period of time than Fc-containing molecules that don't have an altered glycosylation pattern. This is in fact surprising, since it is generally assumed that complex glycosylation is beneficial in prolonging circulating half-life. Moreover, the Fc-containing molecules (e.g., antibodies) do not only remain longer in circulation, but the affinity of these antibodies for their ligands is not affected by the altered glycosylation pattern.

Thus, Fc-containing molecules with altered glycosylation patterns as described herein are provided, which retain antigen binding activity and have increased circulation time in vivo compared to non-modified glycoforms. In these embodiments, the Fc-containing molecules are Fc-containing molecules that bind antigen. For instance, the Fc-containing molecule can be an antibody, but can also be a chimeric Fc-fusion protein, wherein the Fc moiety is fused to a binding moiety (e.g., a nanobody, a Fab, a F(ab')$_2$).

Accordingly, methods are provided to increase circulation time of an Fc-containing molecule to be administered to a subject in need thereof, without altering antigen binding, comprising:
providing an Fc-containing molecule as described herein;
administering the Fc-containing molecule to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: In mammalian cells with intact glycosylation machinery (top), oligomannose glycans entering the Golgi are further trimmed by class I mannosidases (ManI) to Man$_5$GlcNAc$_2$ forms. They are committed to hybrid or complex type N-glycans, upon modification by N-acetylglucosaminyltransferase 1 (GnTI) with a β-1,2-N-acetylglucosamine on the α-1,3-mannose. Multiple glycosylhydrolases and glycosyltransferases further model complex type N-glycans through many biosynthetic steps (WT glycosylation, black arrows in top), leading to substantial heterogeneity. In the 293SGnTI–/– line, glycans are committed to the oligomannose type. These N-glycans are hydrolyzed by Golgi-targeted endoT in GlycoDelete cells, resulting in single N-acetylglucosamine residues (GlycoDelete glycoengineering, bottom). The single GlcNAc stumps can be elongated by galactosyl- and sialyl-transferases (GalT and SiaT) in the Golgi. pHopt, pH optimum. FIG. 1B: The concanavalin A selection strategy directly selects for the desired glycan phenotype, as full deglycosylation of cell surface glycoproteins by endoT would result in the absence of ConA ligands, rendering cells resistant against conA. The parental GnTI–/– cells die when treated with conA. FIG. 1C: Growth curve for 293SGnTI–/– and 293 SGlycoDelete cells counted every 24 hours. Error bars represent SDs for each triplicate (Table 4). Both lines show comparable growth kinetics. FIG. 1D: Scatterplot of average (n=3) gene expression values of 7,344 genes for 293 SGlycoDelete versus 293 SGnTI(–) cells. The correlation coefficient is 0.9865. Significantly differentially expressed genes (moderated t-test in which the standard errors have been moderated across genes according to a simple Bayesian model; $P<0.01$) are labeled with their names. Microarray signal intensities <8 on the represented scale were too low for reliable detection.

FIGS. 3A and 3B represent samples from cells transfected with 1=empty plasmid, 2=s-endoT plasmid, 3=GM$_2$S-endoT plasmid, 4=ST-endoT plasmid. Letters a and b in FIG. 3A represent sample/supernatant 48 and 72 hours after transfection/induction. The + sign indicates purified Flt3ECD as a positive control. It is evident from these blots that both Flt3ECD and 5HT1D samples show a reduction in molecular weight upon transfection of any of the endoT constructs (2, 3, 4), but not with the empty plasmid (1), indicating de-N-glycosylation by the endoT fusion constructs. Clearly, endoT can deglycosylate co-expressed glycoproteins whether it is retained intracellularly (ST-endoT) or not (s-endoT and GM$_2$S-endoT).

Figure 2:
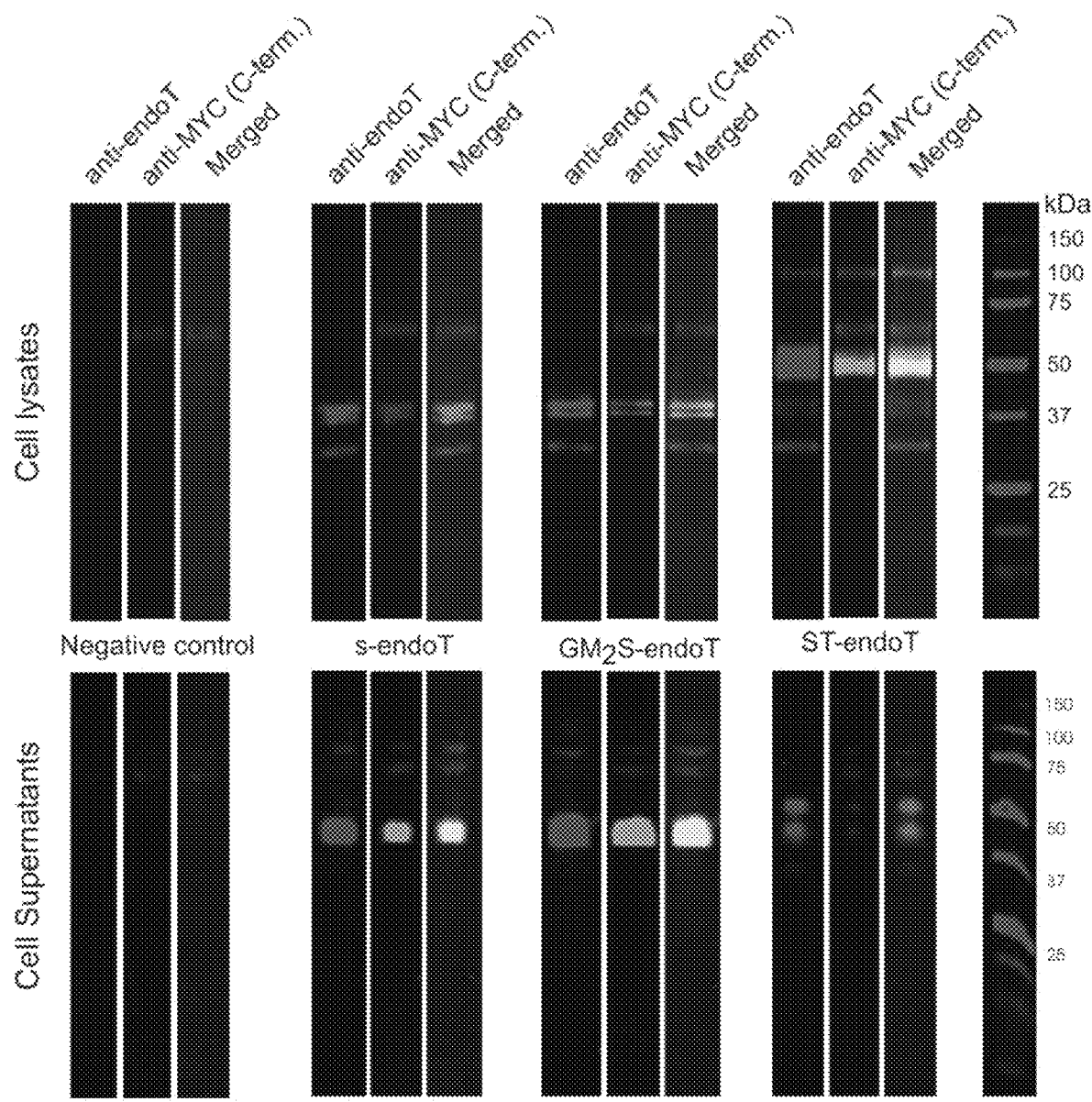
FIG. 2: Evaluation of the two different trans Golgi targeting domains (GM$_2$S-endoT and ST-endoT) compared to secreted endoT (s-endoT). In this experiment, two trans Golgi targeting sequences were evaluated as to which is most effective at retaining a fusion of these sequences with the endoT catalytic domain inside 293 SGnTI–/– cells. For comparison, a secreted version of endoT (i.e., with a secretion signal but no Golgi targeting sequences) was analyzed. The Western blots of SDS-PAGE separated cell lysate proteins and of proteins present in the cell cultivation medium were developed with a polyclonal anti-endoT antiserum or with a monoclonal anti-c-Myc epitope antibody. The c-Myc epitope is C-terminally fused to the different protein constructs and its presence or absence thus came to the conclusion on C-terminal processing of the proteins. From these results, it is clear that the GM$_2$S-derived sequence is ineffective at retaining endoT intracellularly, as this construct yields the same distribution of intra- and extracellular endoT forms as the secreted version of the protein. It appears that the GM$_2$ sequence is efficiently cleaved off. To the contrary, the ST-derived sequence effectively retains endoT intracellularly and the major band at 50 kDa matches the expected molecular mass of the ST-endoT fusion protein. Some minor secretion of two C-terminally proteolyzed forms still occurs. The weak intracellular band that can be observed at 100 kDa probably represents ST-endoT dimers, since the ST6GalI domain is known to oligomerize.[1]

FIGS. 5A and 5B: Validation of endoT by PCR and Western blot. FIG. 5A: PCR validation of the presence of the ST-endoT coding sequence in 293 SGlycoDelete cells genomic DNA (gDNA). Analysis of the PCR products by capillary electrophoresis illustrates the presence of a specific PCR product of the expected length (346 bp) with 293 SGlycoDelete gDNA as the template (arrow). This amplicon is not generated with 293SGnTI−/− gDNA as the template for the PCR reaction. FIG. 5B: Samples from 293SGnTI−/− and 293SGlycoDelete cells were analyzed by immunoblotting to detect the presence of endoT catalytic domain (polyclonal rabbit anti-endoT). The main band in the 293 SGlycoDelete cell lysate runs at the expected MW of monomeric ST-endoT (49.8 kDa). Bands at approximately 100 and 200 kDa in the 293SGlycoDelete cell lysate are probably oligomers, while bands at lower MW likely represent degradation products. The oligomers are also observed in transient transfection experiments with the ST-endoT construct (FIG. 2). No signals for these bands can be detected in the 293 SGnTI−/− lysate.

FIGS. 6A and 6B: Comparative expression scatterplots of the S-lineage cell lines. Values represent the mean log 2 signal intensities of expressed genes as determined after background correction and removal of noise. FIG. 6A: 293 SGnTI−/− versus 293 S. The correlation coefficient is 0.947. From the 7526 expressed genes, 68 were found to be significantly differentially expressed (p<0.01) with at least a two-fold change in expression in the 293SGnTI−/− line compared with 293S. FIG. 6B: 293 SGlycoDelete vs 293S. The correlation coefficient is 0.938. From the 7473 expressed genes, 70 were found to be significantly differentially expressed (p<0.01) with at least a two-fold change in expression in the 293 SGlycoDelete line compared with 293 S. Of these genes, 45 (−/+65%) are the same for both the derived cell lines versus the parental 293S cells.

Figure 7A:
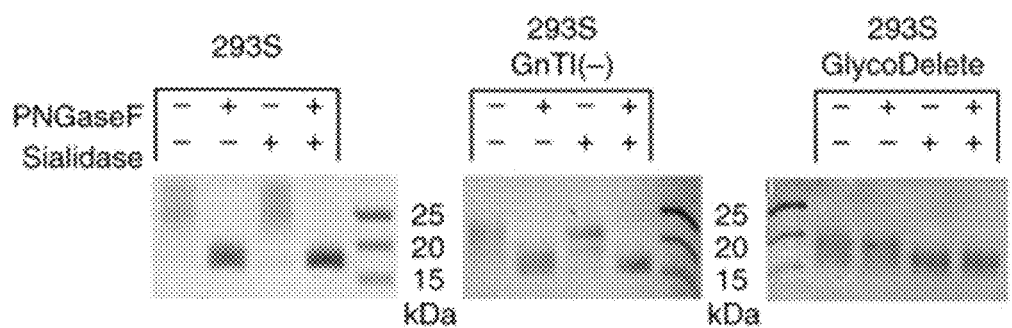
Figure 7B:
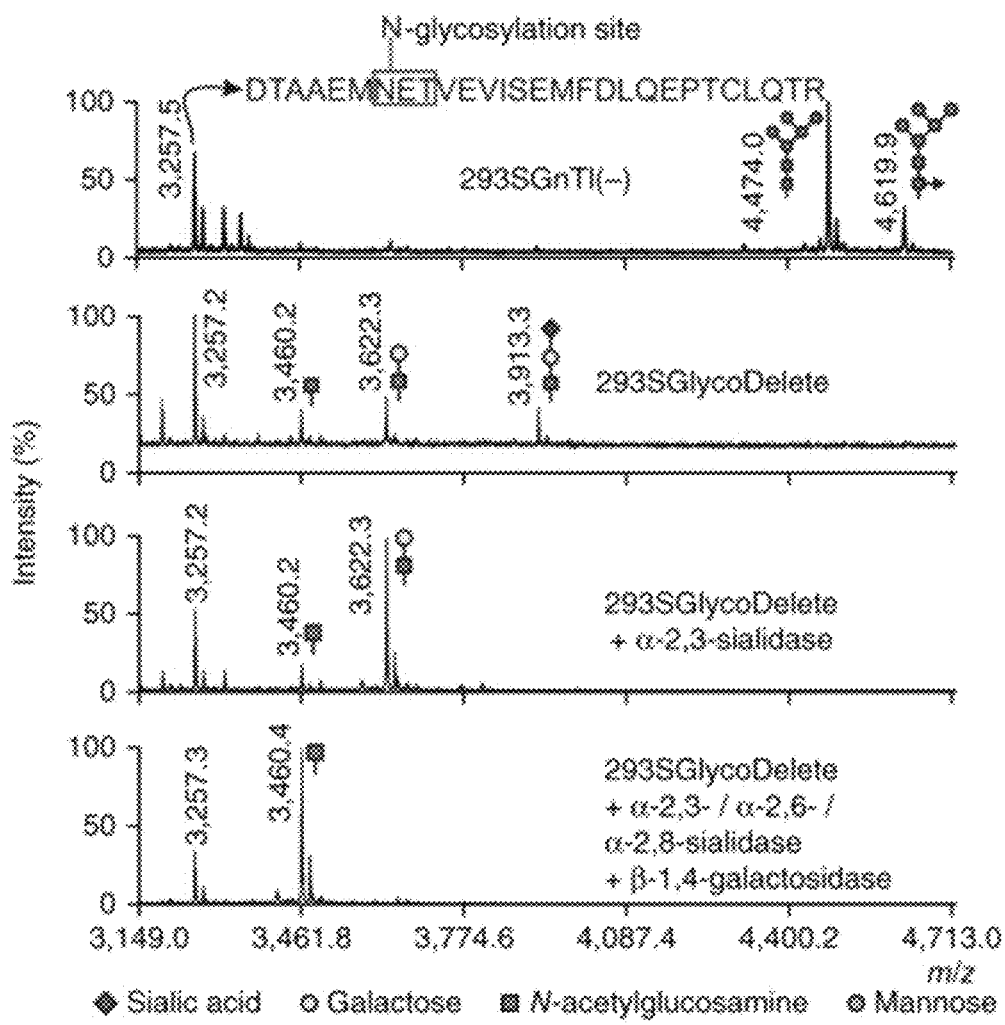
Figure 7C:
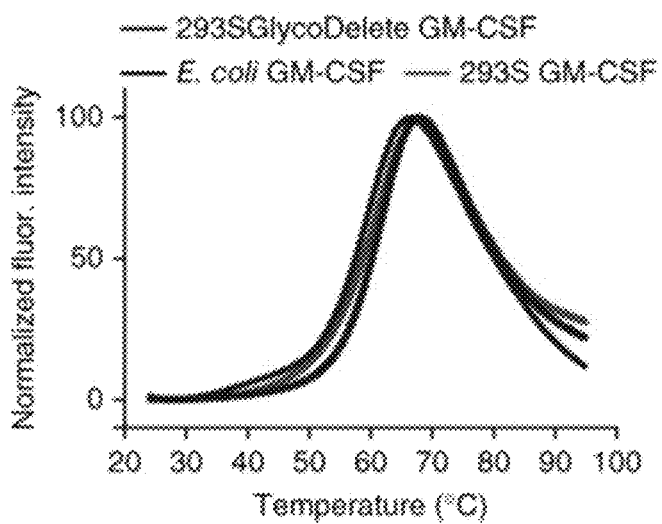
Figure 7D:
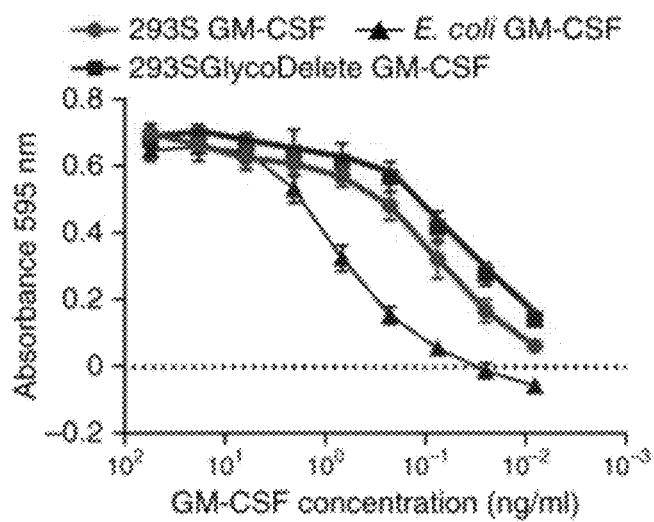
Figure 7E:
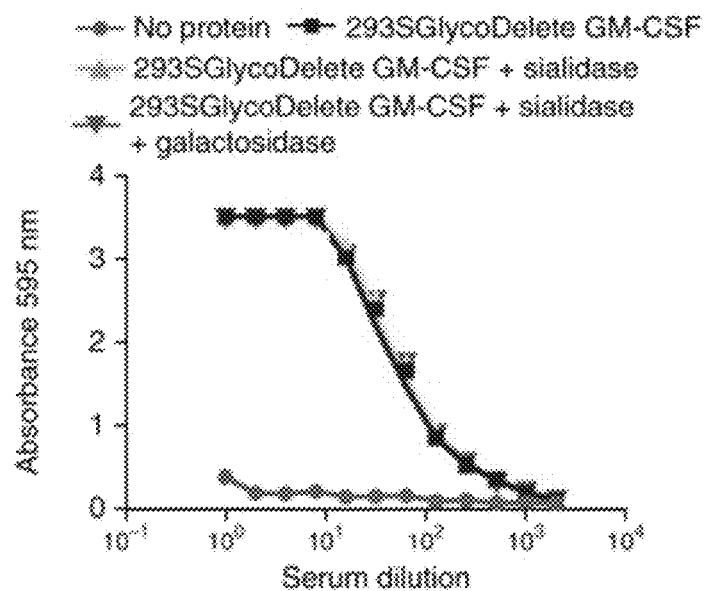
Figure 7F:
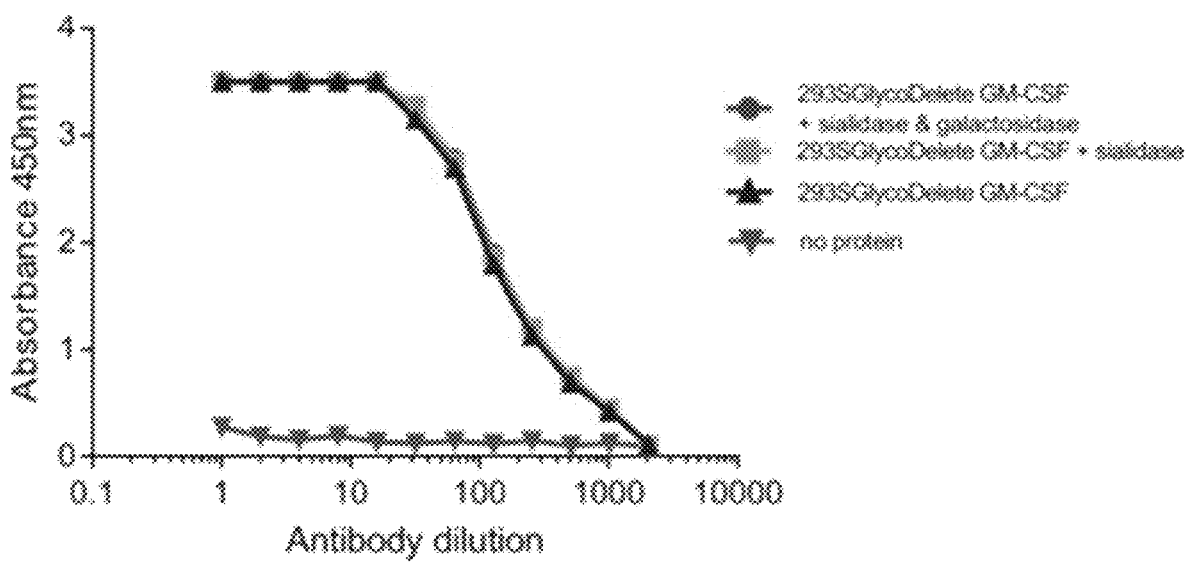

FIGS. 7A-7F: GlycoDelete glycan characterization. FIG. 7A: SDS-PAGE of GM-CSF samples from 293S, 293 SGnTI(−) and 293 SGlycoDelete cells. Each sample was treated with PNGaseF, sialidase or both, analyzed on an SDS-PAGE gel and stained with Coomassie Brilliant Blue. kDa, kilodalton. FIG. 7B: MALDI-time-of-flight-MS spectra of GM-CSF samples (SEQ ID NO:25). Peaks are labeled with their mass/charge ratio (m/z) values. The spectrum of the 293 SGnTI(−) GM-CSF reveals the presence of Man5GlcNAc2 (left) and fucosylated Man5GlcNAc2 (right) on the glycopeptide containing N37. These glycoforms are absent in GlycoDelete GM-CSF. New peaks at m/z values corresponding to HexNAc, Hex-HexNAc and Neu5Ac-Hex-HexNAc-modified glycopeptides are detected. Spectra of exoglycosidase-digested GlycoDelete GM-CSF N-glycans with α-2,3-sialidase or both a broad spectrum sialidase and β-1,4-galactosidase are shown. These spectra show that N-glycans on GlycoDelete GM-CSF N37 are Neu5Ac-α-2,3-Gal-β-1,4-GlcNAc and Gal-β-1,4-GlcNAc. FIG. 7C: ThermoFluor assay of GM-CSF produced by 293S, 293 SGlycoDelete and E. coli cells. Similar average (n=3) melting curves were observed for all GM-CSF glycoforms (Tm is ~60° C.). FIG. 7D: Bioactivity of 293 S- and 293 SGlycoDelete-produced GM-CSF as measured in a TF1 erythroleukemia cell-proliferation assay (n=3). E. coli-produced GM-CSF serves as a nonglycosylated control sample. Error bars, s.d. (Table 5). FIG. 7E: ELISA analysis of anti-glycan antibody titers in GlycoDelete GM-CSF immunized rabbit serum. Removal of sialic acid and galactose monosaccharides from the GlycoDelete glycan does not reduce serum antibody recognition (Table 6). FIG. 7F: duplicate experiment as described in FIG. 7E.

Figure 8:
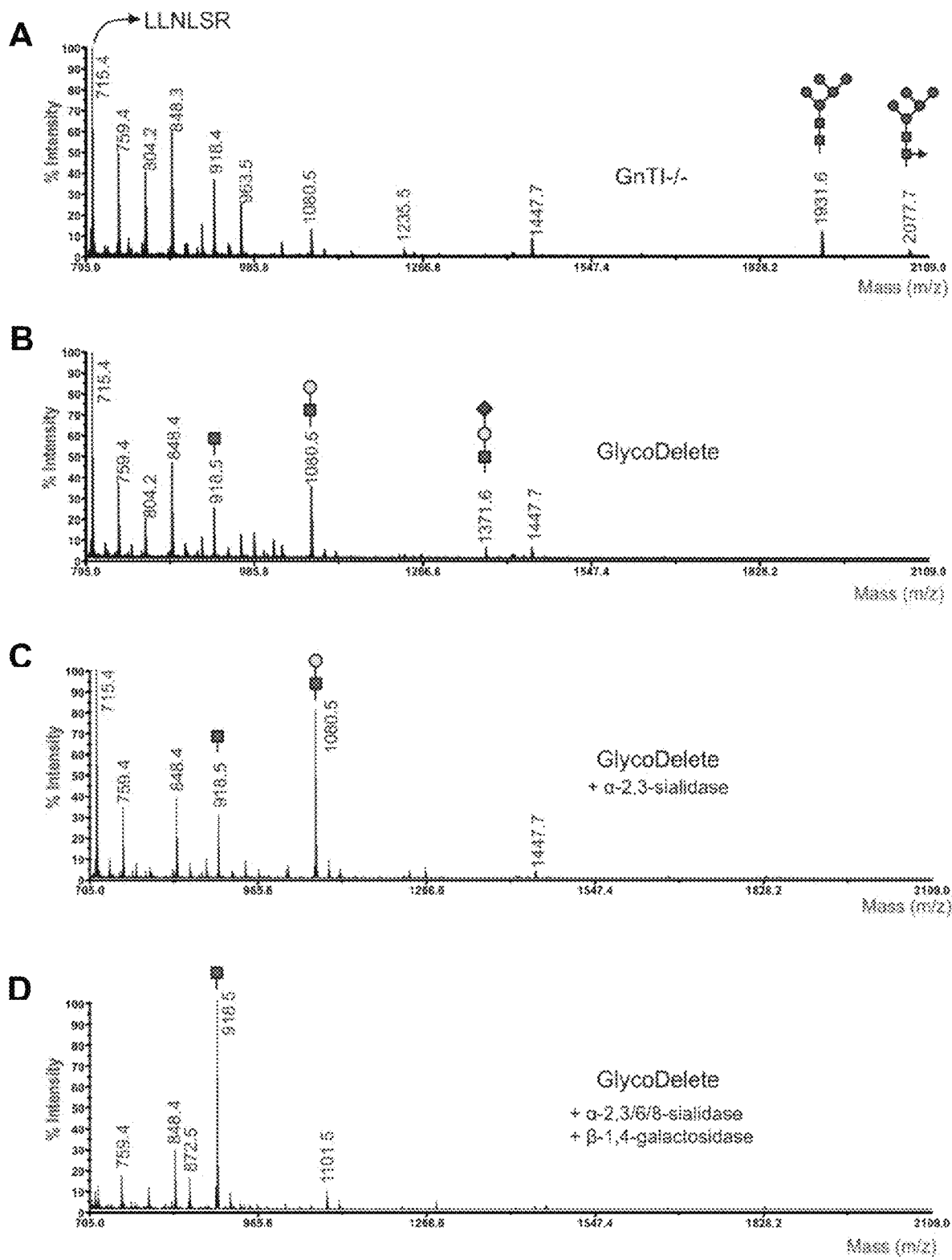

FIG. 8: MALDI-TOF-MS of GM-CSF glycopeptides. Glycopeptides encompassing Asn 27 in both lines, showing the presence of Man5GlcNAc2-Asn (m/z=1931.6) and fucosylated Man5GlcNAc2-Asn (m/z=2077.7) in GnTI−/− GM-CSF (Row A). These glycoforms are absent in GlycoDelete GM-CSF (Row B). Peaks at m/z=918.5, 1080.5 and 1371.6 are detected in GlycoDelete GM-CSF, representing Hex-NAc-Asn, Hex-HexNAc-Asn and Sia-Hex-HexNAc-Asn, respectively. Analysis of exoglycosidase-digested GlycoDelete GMCSF N-glycans with α-2,3-sialidase (Row C) or both a broad spectrum A. ureafaciens sialidase and S. pneumoniae β-1,4-galactosidase (Row D) are shown. The spectra illustrate that the N-glycans on GlycoDelete GM-CSF are Neu5Ac-α-2,3-Gal-β-1,4-GlcNAc-Asn and Gal-β-1,4-GlcNAc-Asn.

Figure 9:
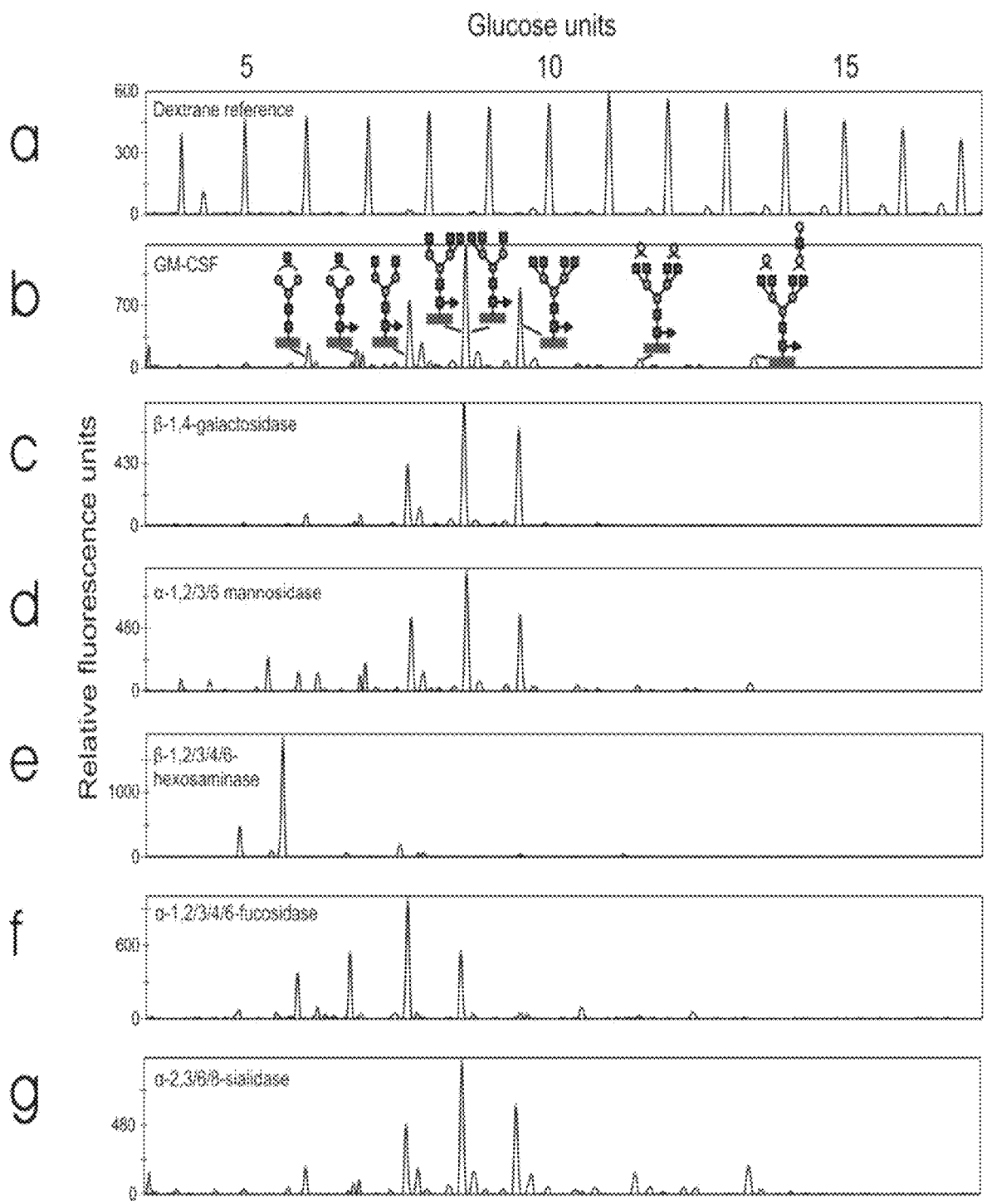

FIG. 9: DSA-FACE analysis of GM-CSF produced in 293S cells. Row a: dextran ladder reference. Row b: DSA-FACE profile of untreated GM-CSF produced in 293S cells with annotated structures. Glycosylation of GM-CSF produced in 293S cells results in a heterogeneous mix of mainly di-, tri-, and tetra-antennary fucosylated complex type N-glycans without galactosylation. At lower electrophoretic mobility, some galactosylated structures are observed. Row c: Galactosylated structures disappear from the spectrum upon galactosidase digestion. Row d: Two minor annotated peaks at the highest electrophoretic mobility collapse to a single peak with even higher electrophoretic mobility after mannosidase digestion. No further major changes occur after mannosidase digestion, indicating little terminal mannose residues are exposed. Row e: Most annotated peaks shift to two peaks at high electrophoretic mobility upon hexosaminidase treatment. The minor peak represents the non-fucosylated core N-glycan; the major peak represents the fucosylated trimannosyl core N-glycan. Row f: Core fucosylation for the majority of the N-glycans was observed. This is illustrated by a shift toward higher electrophoretic mobility of many of the observed peaks after fucosidase treatment of the glycans. Row g: No major changes were observed in the glycan profile upon treatment with a broad-spectrum sialidase, suggesting the absence of sialylation in the glycans of GM-CSF produced in 293S cells.

Figure 10:
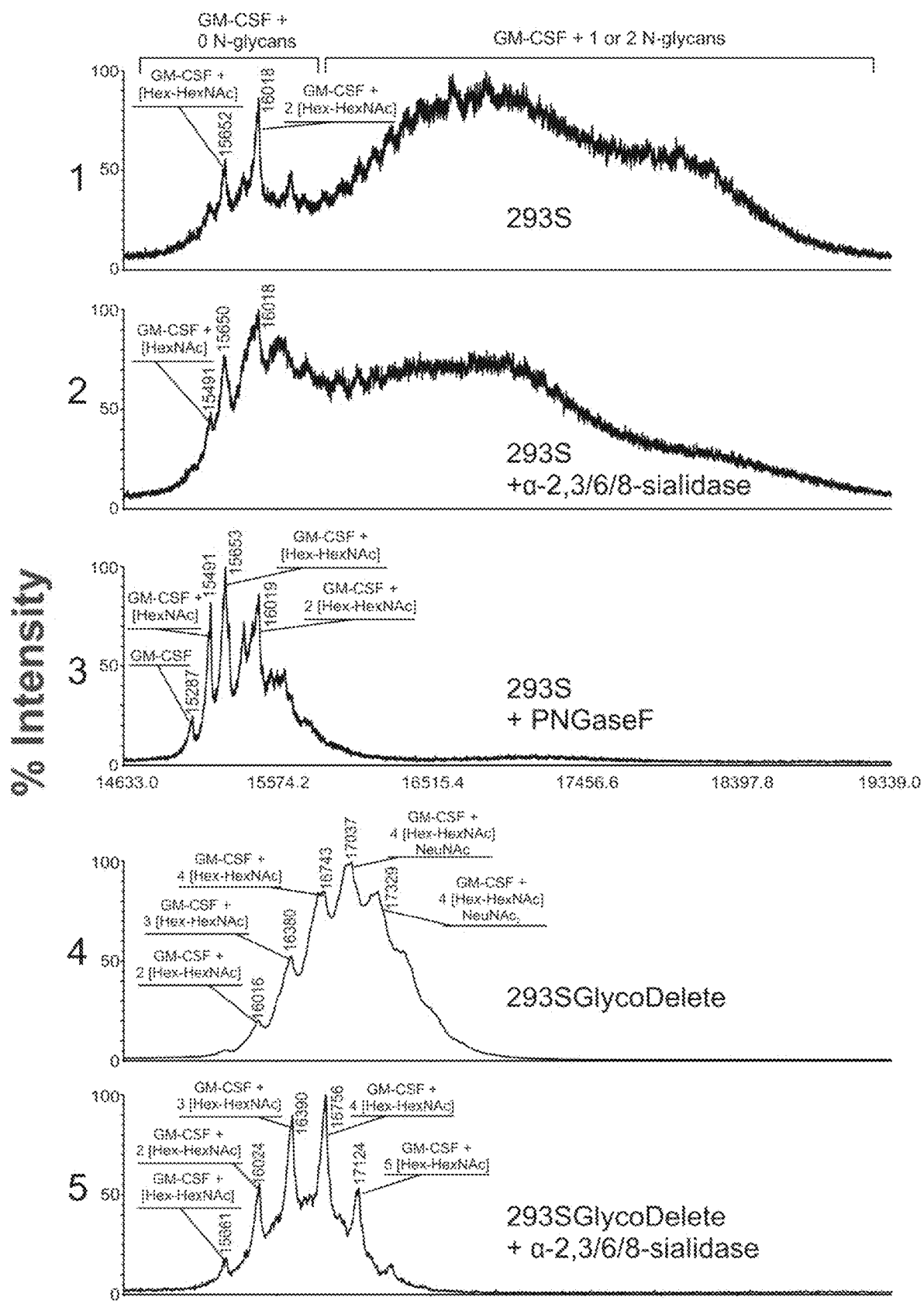

FIG. 10: MALDI-TOF-MS analysis of hGM-CSF produced in 293 GlycoDelete and 293S cells. Row 1: 293 S-produced hGM-CSF. The enormous observed heterogeneity is largely due to the variability of 293S N-glycosylation. Row 2: hGM-CSF sialidase digest results in some heterogeneity reduction. Row 3: hGM-CSF digested with PNGaseF has a strongly reduced heterogeneity, demonstrating that N-glycosylation is the main source of molecular weight heterogeneity. Row 4: 293 SGlycoDelete produced hGM-CSF has a strongly reduced heterogeneity. Row 5: Sialidase digest on 293 SGlycoDelete produced hGM-CSF reveals a pattern of similarly low complexity as the completely de-N-glycosylated 293 S-produced protein.

Figure 11:
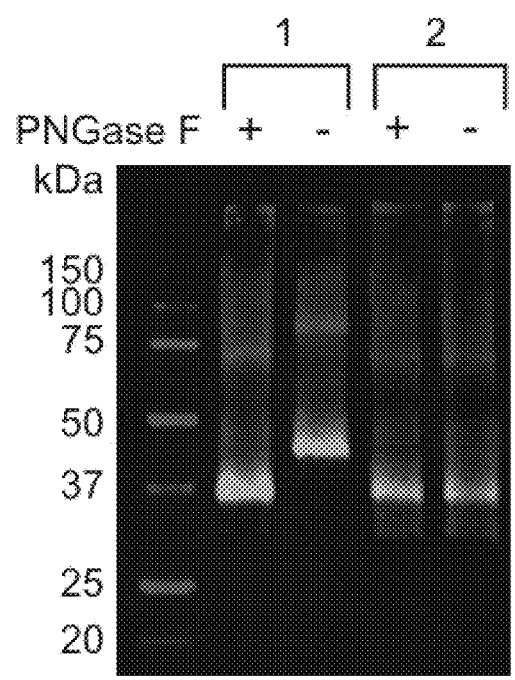

FIG. 11: Immunoblotting of 5HT1DR produced in 293SGnTI−/− and 293S GlycoDelete cells. Treatment of membrane protein extracts with PNGaseF revealed a large shift in the molecular weight (MW) of the 5HT1DR stably produced n 293 SGnTI−/− cells (1), as expected. Contrary to this, receptor produced in 293 SGlycoDelete cells (2) did not shift in MW upon PNGaseF treatment and ran at approximately the same MW as deglycosylated (PNGaseF-treated)

receptor from 293 SGnTI−/− cells. This is consistent with a complete removal of the 5HT1DR N-glycans in the 293S GlycoDelete cells.

Figure 12:
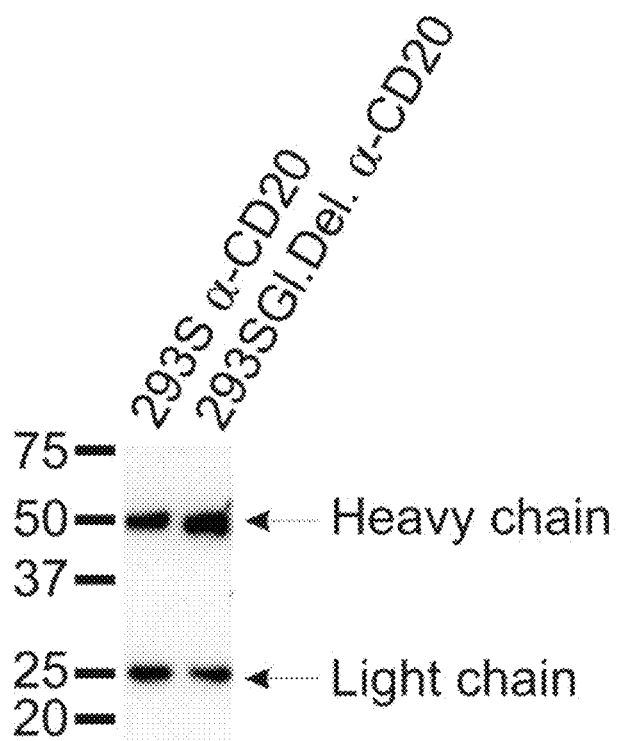

FIG. 12: Immunoblot analysis of anti-CD20 produced in 293S or 293S GlycoDelete cells. Equal volumes of culture medium of 293S wild-type cells and 293 SGlycoDelete cells upon transient transfection using identical methods were analyzed by immunoblotting. Consequently, the blot shows the level of protein expression of the anti-CD20 monoclonal antibody in the culture medium. The yield of the recombinant protein is similar for both cell lines, indicating that the genetic manipulations used to derive GlycoDelete 293 cells from the WT 293S precursors do not substantially affect the cell's capacity of protein secretion.

Figure 13:
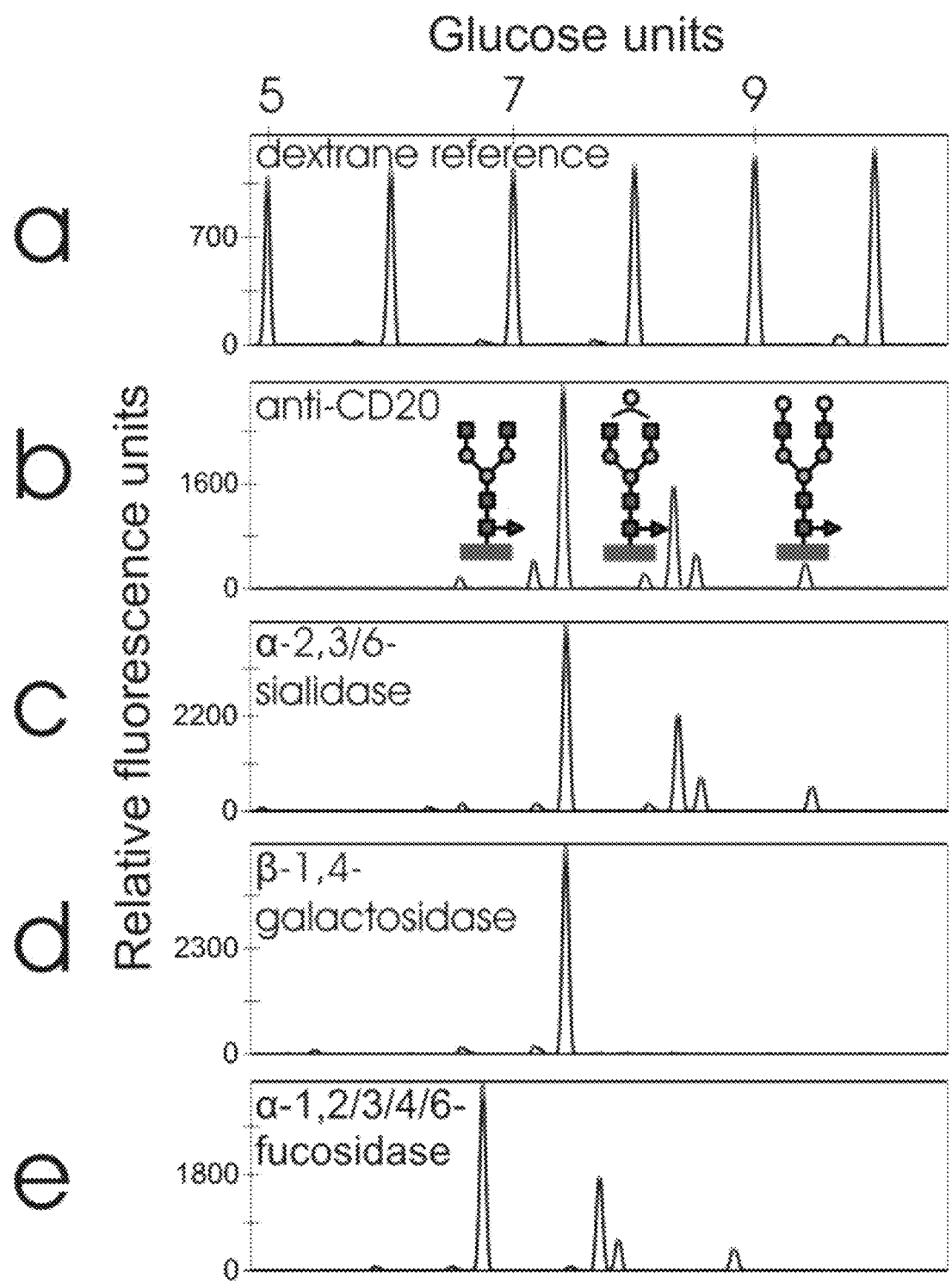

FIG. 13: DSA-FACE analysis of anti-CD20 produced in 293S cells. Row a: dextran ladder reference. Row b: DSA-FACE profile of untreated anti-CD20 produced in 293S cells with annotated structures. Glycosylation of anti-CD20 produced in 293S cells results in core-fucosylated diantennary N-glycans with or without galactosylation. Row c: No major changes were observed in the glycan profile upon treatment with a broad-spectrum sialidase, suggesting the absence of sialylation in the glycans of anti-CD20 produced in 293S cells. Row d: Galactosylated structures disappear from the spectrum upon galactosidase digestion. A single peak remains, representing the non-galactosylated core-fucosylated diantennary N-glycan. Row e: Core fucosylation for all detected N-glycans was observed. This is illustrated by a shift toward higher electrophoretic mobility of the observed peaks after fucosidase treatment of the glycans.

Figure 14A:
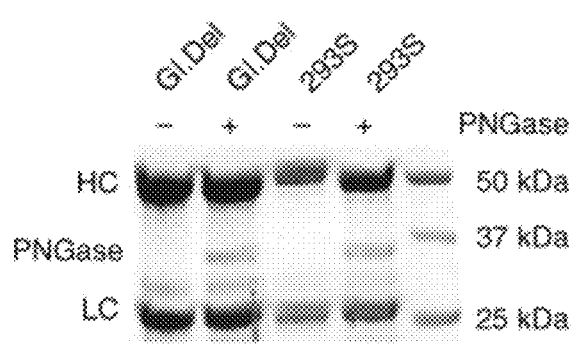
Figure 14C:
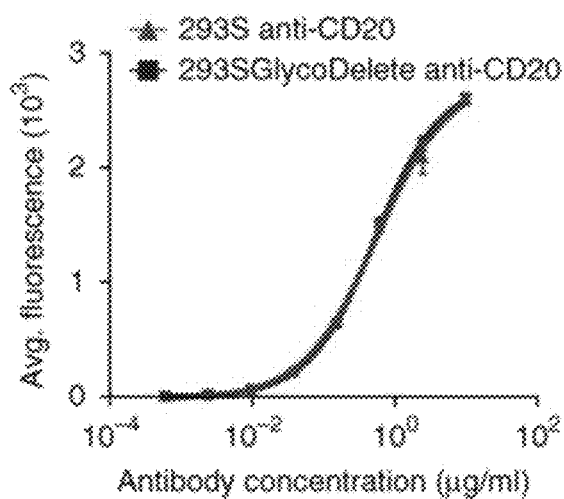
Figure 14B:
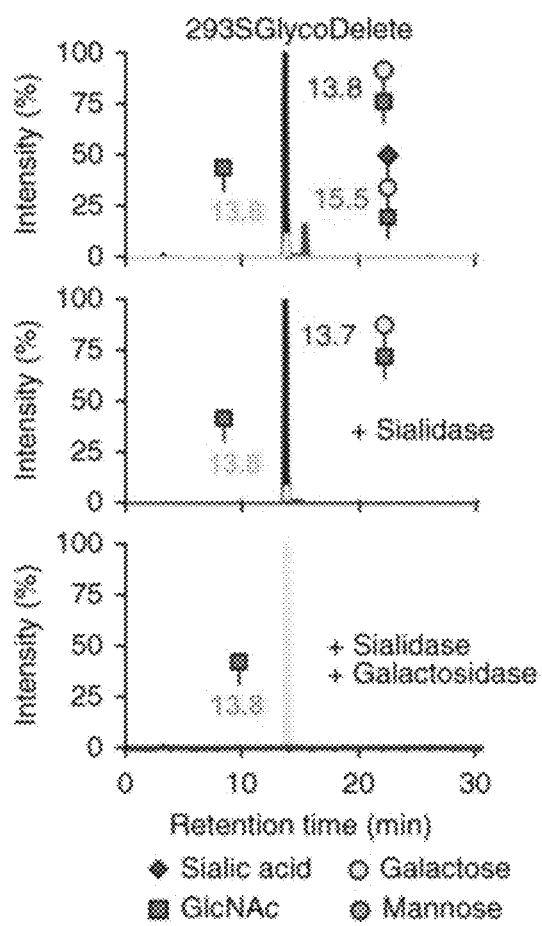
Figure 14D:
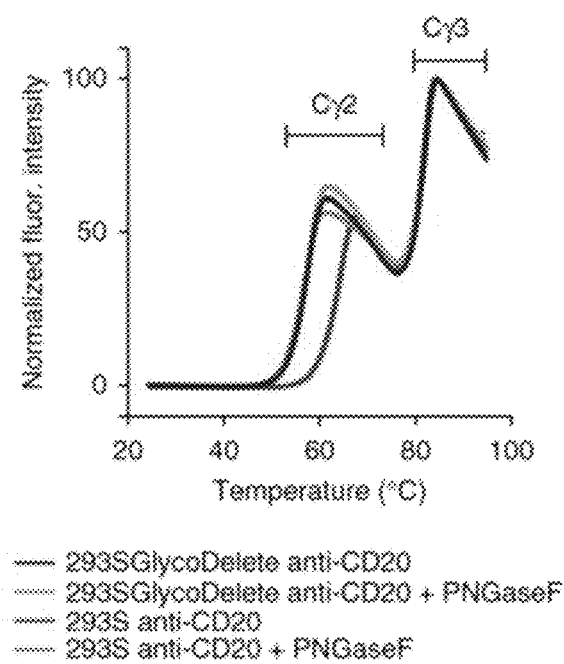
Figure 14E:
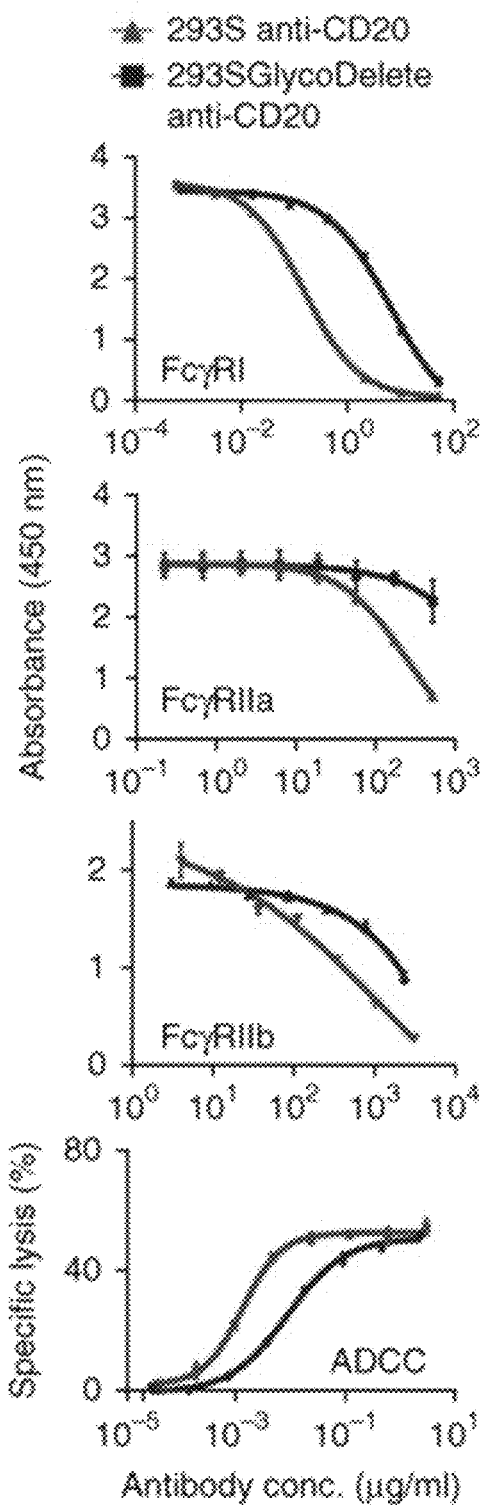
Figure 14F:
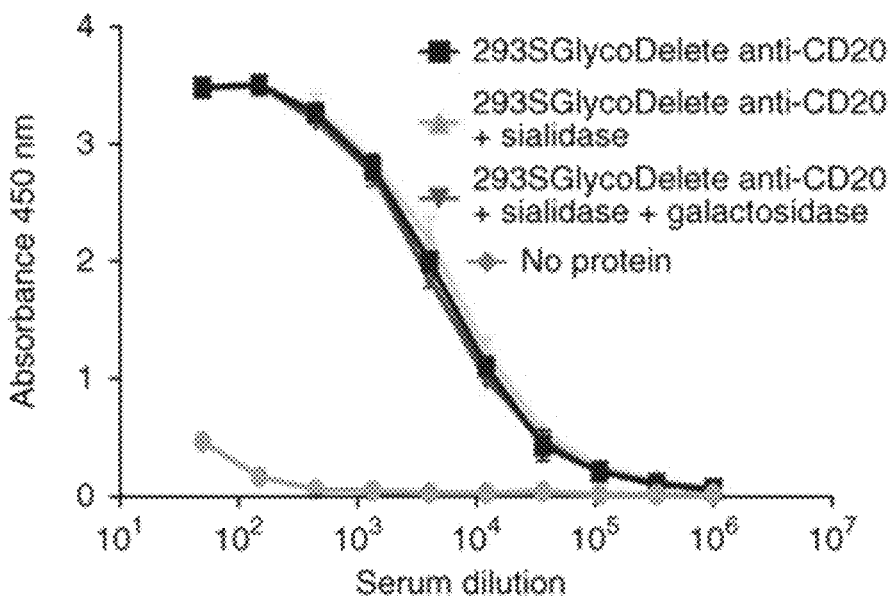
Figure 14G:
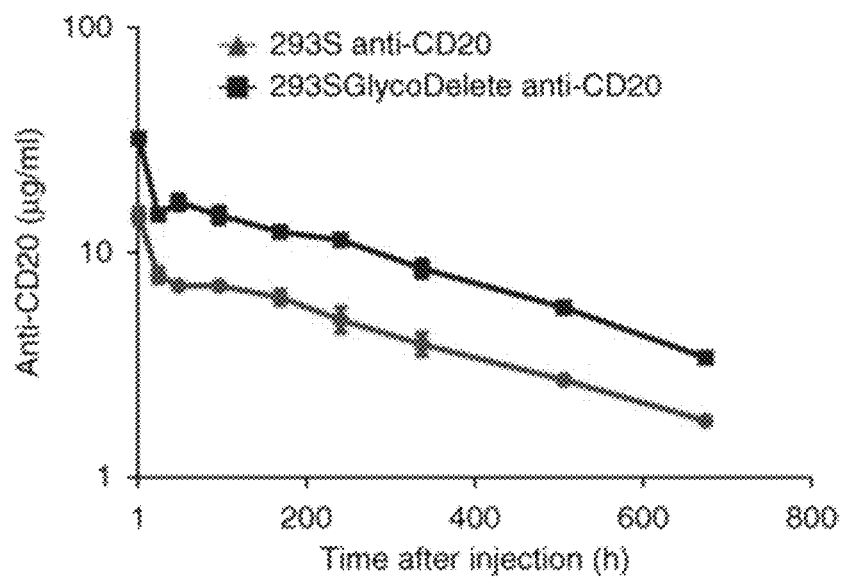

FIGS. 14A-14G: Functional and immunological characterization of GlycoDelete anti-CD20. FIG. 14A: SDS-PAGE of anti-CD20 from 293 SGlycoDelete (Gl.Del) and 293S cells. On the left, "PNGase" indicates the PNGase enzyme band. HC, antibody heavy chain; LC, antibody light chain; kDa, kilodalton. FIG. 14B: LC-MS/MS in SRM mode of GlycoDelete anti-CD20 glycopeptides. Peak labels state LC elution times (minutes). Trisaccharide-, disaccharide- and monosaccharide-modified glycopeptides are shown in red, blue and yellow, respectively. Exoglycosidase digests with sialidase and β-1,4-galactosidase illustrate identical glycans as observed for GM-CSF. FIG. 14C: CD20-binding by anti-CD20 as assessed by flow cytometry (Table 7). FIG. 14D: Average melting curves (n=3) as determined in a ThermoFluor assay for untreated or PNGaseF-digested 293S and 293 SGlycoDelete anti-CD20. FIG. 14E: Competition ELISA (top three) and ADCC assay (bottom) to assess effector function of the anti-CD20 Fc. Concentration series of 293S and 293 SGlycoDelete anti-CD20 comparing competition with a coated anti-Fc antibody. Error bars (ELISA), s.e.m. (n=3). Error bars (ADCC), s.d., n=3 (Table 8). FIG. 14F: Anti-glycan antibody ELISA analysis of 293 SGlycoDelete anti-CD20 immunized rabbit serum. Analysis of anti-CD20 recognition by antibodies in the serum of rabbits immunized with GlycoDelete GM-CSF. Anti-CD20 samples were treated with sialidase, sialidase and galactosidase or no enzyme. Error bars, s.d., n=3 (Table 9). FIG. 14G: Blood concentrations of anti-CD20 measured over time after intravenous injection of 293S or 293 SGlycoDelete anti-CD20. Error bars, s.e.m., n=4. Numerical data for this graph are in Table 10.

Figure 15A:
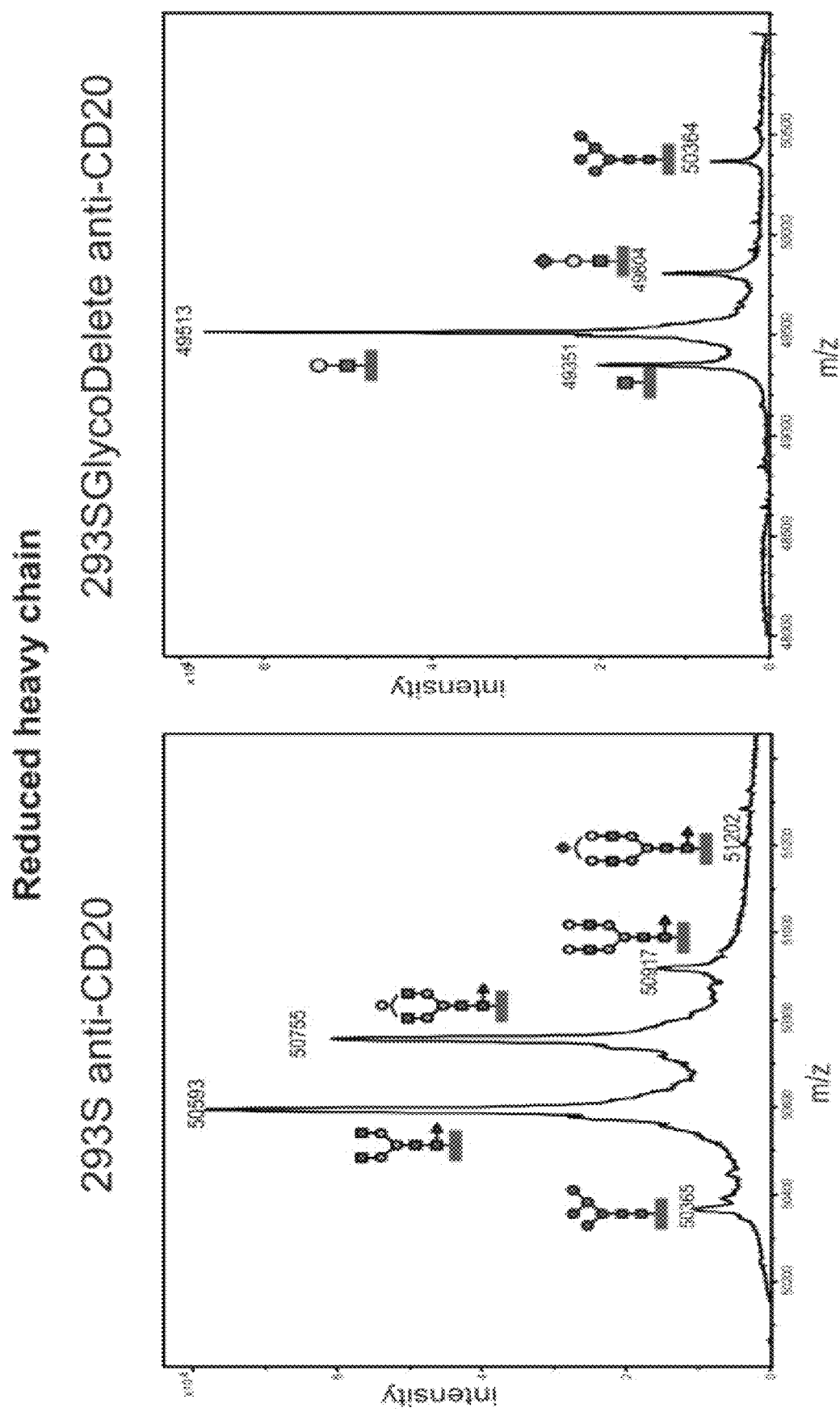
Figure 15B:
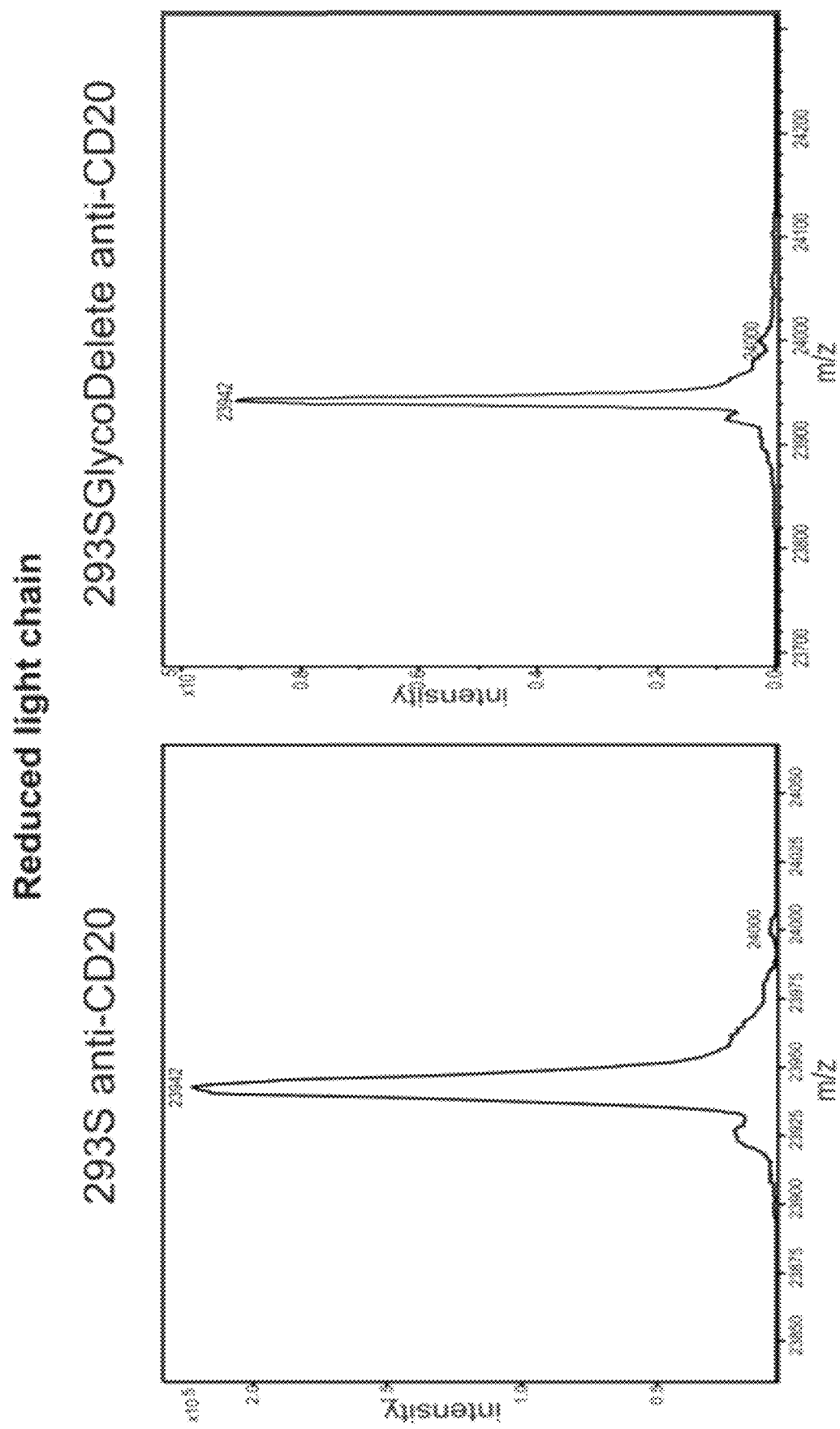
Figure 15C:
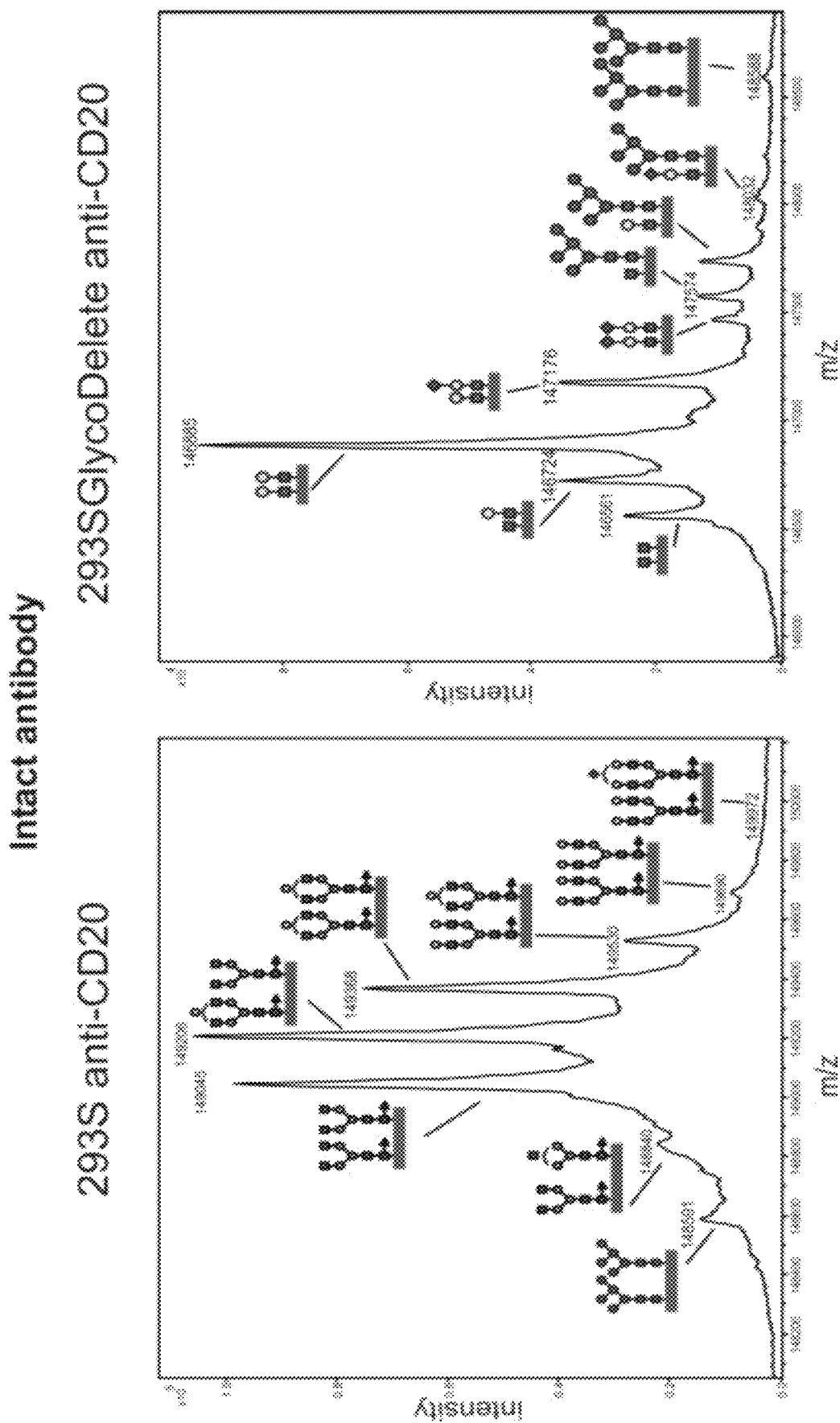

FIGS. 15A-15C: LC-MS analysis of anti-CD20 hIgG1 produced in 293S (left) and 293 SGlycoDelete (right) cells. FIG. 15A: deconvoluted ESI spectrum for the reduced heavy chain, which carries the single N-glycosylation site. For 293 S-produced anti-CD20, the typical core-fucosylated agalacto-, mono-, and bi-galactosylated biantennary glycans are the dominant species, while a low amount of Man5Gn2 N-glycan is also detected. Sialylation is almost undetectable. For the 293 SGlycoDelete anti-CD20, HexNAc-Asn, Hex-HexNAc-Asn and NeuNAc-Hex-HexNAc-Asn dominate the spectrum, while a minor fraction of Man5Gn2 is also formed herein. Importantly, no non-N-glycosylation-related heterogeneity is detectable, supporting the notion that GlycoDelete manipulation of HEK293 cells does not lead to the unexpected induction of other post-translational modification pathways. FIG. 15B: The light chain was unaffected by the GlycoDelete engineering as it carries no N-glycosylation sites. FIG. 15C: Deconvoluted mass spectra for the intact, nonreduced antibody. All species can be interpreted as a combinatorial series of the glycoforms on both heavy chains. In both antibodies, the number of S-S bridges is calculated as 12-13, based on the difference in mass between the reduced chains and the assembled antibody.

Figure 16:
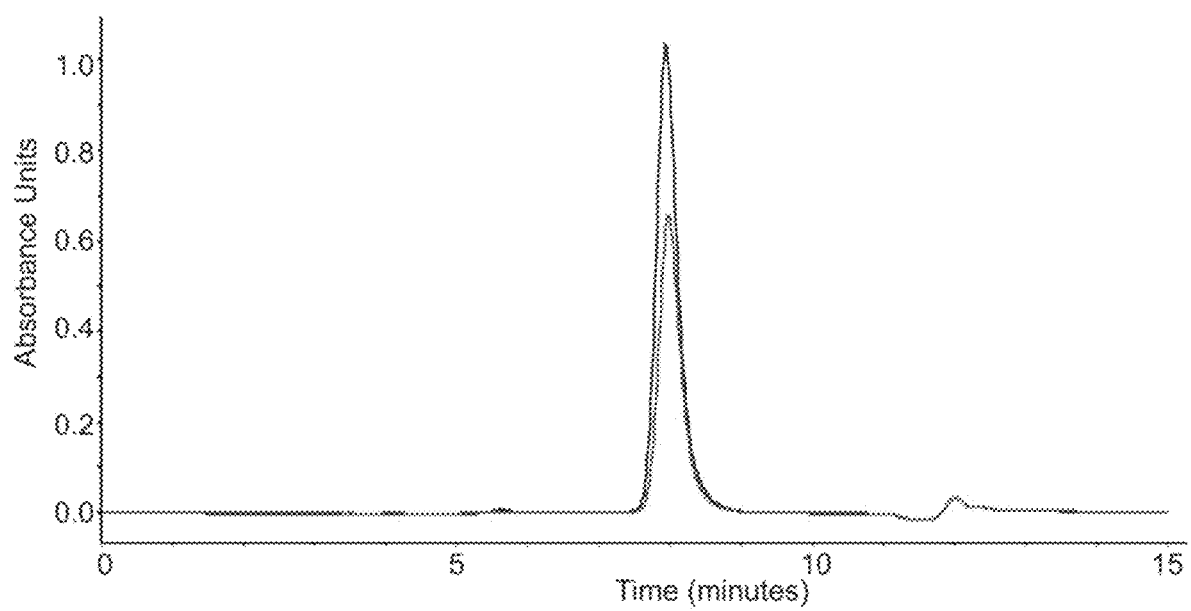

FIG. 16: Size exclusion chromatography of anti-CD20. Size exclusion chromatography of 293S anti-CD20 (blue line) and 293 SGlycoDelete anti-CD20 (red line). Only the monomeric peak is detected indicating that there is no aggregation in both glycoforms.

Figure 17:
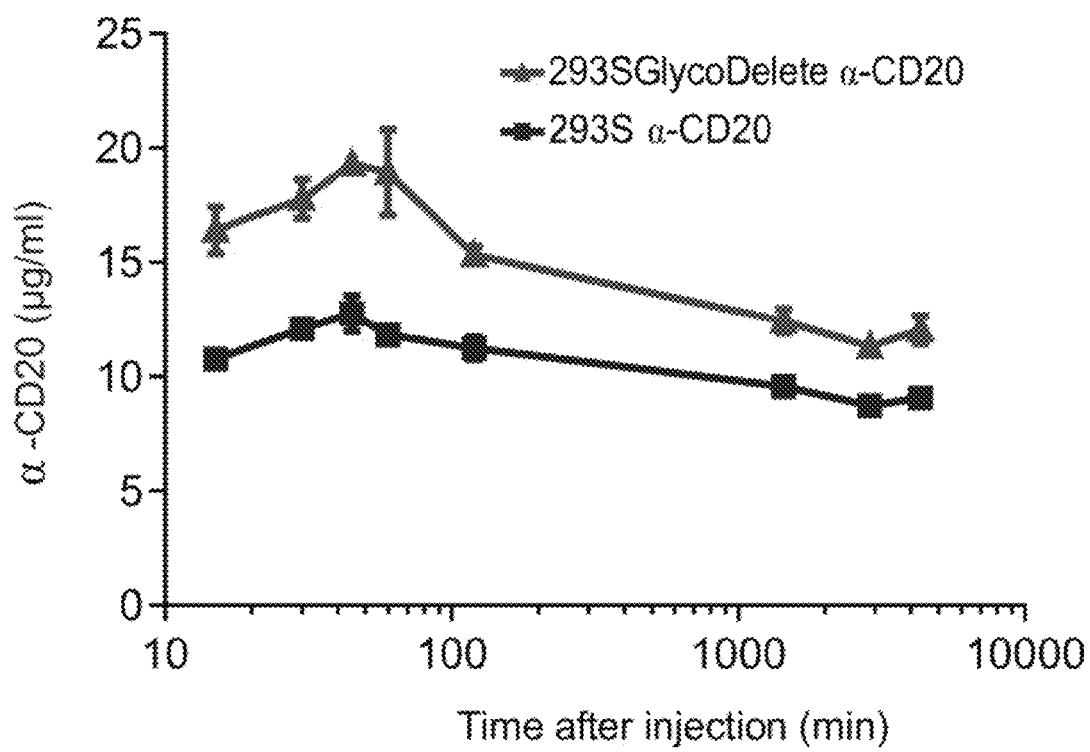

FIG. 17: Anti-CD20 pharmacokinetics in mice. Repeat experiment in an independent laboratory from the experiment shown in FIGS. 14A-14G of the main text, also including earlier time points post-injection. Before reaching the peak concentration in the blood, less of the anti-CD20 is removed, resulting in increased circulating levels. The subsequent slow clearance (beyond 1 hour post-injection) is comparable for both glycoforms, as also observed in the experiment reported in FIGS. 14A-14G.

FIG. 18: GlycoDelete produced Etanercept Fc-chain glycan analysis. Data shown for one run are representative of three runs.

DETAILED DESCRIPTION

Definitions

This disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual*, 2$^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

A "higher eukaryotic cell" as used herein refers to eukaryotic cells that are not cells from unicellular organisms. In other words, a higher eukaryotic cell is a cell from (or derived from, in case of cell cultures) a multicellular eukaryote. Typically, the higher eukaryotic cells will not be fungal cells. Even more typically, the higher eukaryotic cells will not be plant cells or fungal cells. Particularly, the term refers to animal cells (or, typically, cell lines, such as insect cell lines or mammalian cell lines). More particularly, the term refers to vertebrate cells, even more particularly to mammalian cells. The higher eukaryotic cells as described herein will typically be part of a cell culture (e.g., a cell line, such as an HEK or CHO cell line), although this is not always strictly required (e.g., in case of plant cells, the plant itself can be used to produce protein).

An "endoglucosaminidase" or "endoglucosaminidase enzyme" as used herein refers to enzymes that hydrolyze the bond between the anomeric carbon of a non-terminal beta-linked N-acetylglucosamine residue in an oligosaccharide of a glycoprotein or a glycolipid, and its aglycon, thereby releasing mono- or oligosaccharides from glycoproteins or glycolipids or sugar polymers. Endoglucosaminidases are a subset of the glycosidases, and may or may not have other enzymatic activities (such as, e.g., glycosyltransferase activity). A particular class of endoglucosaminidases is formed by the endo-β-N-acetylglucosaminidases or mannosyl-glycoprotein endo-β-N-acetylglucosaminidases, indicated as EC 3.2.1.96 in the International Union of Biochemistry and Molecular Biology (IUBMB) nomenclature. This particular class of enzymes are capable of catalyzing the endohydrolysis of the N,N'-diacetylchitobiosyl unit in high-mannose glycopeptides and glycoproteins containing the -[Man(GlcNAc)2]Asn- structure. One N-acetyl-D-glucosamine (GlcNAc) residue remains attached to the protein; the rest of the oligosaccharide is released intact. Thus, the result is a single GlcNAc-modified glycoprotein. Of note, the remaining GlcNAc residue may be either unmodified or still be modified with other sugar residues in positions other than that of the hydrolyzed bond, for instance, the GlcNAc residue may carry a fucose on position 3 or 6. Nevertheless, glycoproteins with a modified GlcNAc residue will still be referred to as single GlcNAc-modified proteins, as there is no second sugar residue on position 4 of the GlcNAc residue (i.e., there is no typical sugar chain). A particular advantage of endoglucosaminidases as compared to exoglycosidases is that they allow discrimination between N-linked and O-linked glycans and between classes of glycans. A non-limiting list of endoglucosaminidases is provided in the application.

An "Fc-containing molecule" as used in the application refers to proteins or fusion proteins that contain an Fc region. An Fc region (fragment-crystallizable region) is the tail region of an immunoglobulin that interacts with cell surface receptors called Fc receptors and some proteins of the complement system. According to particularly envisaged embodiments, the Fc region in the Fc-containing molecule is an Fc region from an immunoglobulin G (IgG) isotype. This can be any of the IgG subclasses (IgG1, 2, 3, 4 in humans). For IgG, like IgA and IgD isotypes, the Fc region is composed of two identical protein fragments, derived from the second and third constant domains of the antibody's two heavy chains. The Fc regions of IgGs bear a highly conserved N-glycosylation site, indicated as N297 (Asn-297 or Asparagine 297). "Fc-containing molecules" as used herein encompass both proteins that naturally have an Fc region (such as immunoglobulins), or fusion proteins or molecules, wherein an Fc region is fused to a protein, peptide or other molecule (particularly a binding moiety). Examples of Fc-fusion proteins include, but are not limited to, those described in Huang, 2009. Of note, an Fc molecule as such is also an Fc-containing molecule. A particular class of Fc-containing molecules are Fc-containing molecules that can bind antigen. Examples are antibodies, or fusion proteins wherein an Fc region is linked to a binding moiety (e.g., a nanobody, a Fab region, a F(ab')2 region).

Typically, the Fc part in the Fc-containing molecules will be a human or humanized sequence, meaning that the amino acid sequence of the Fc region is at least 95% identical to a human Fc sequence, particularly at least 99% identical to a human Fc sequence, or most particularly is 100% identical to a human Fc sequence. However, the disclosure is not limited to human sequences. For instance, it is possible that the Fc region is that of a mouse, or of a camelid, a rhesus monkey, a dog, a cow, a guinea pig, a sheep, a goat, a horse, a rat, a rabbit, a cat, or any other mammal. It is even possible that the Fc region is from non-mammalian animals (e.g., a chicken). In such cases, the skilled person will understand that, while the N-glycosylation site is conserved across species, the exact position may differ and is not always N297. Using a simple sequence alignment, the right residue can be identified, if necessary.

A "Golgi localization signal" is a molecule, typically a peptide, that directs localization of the polypeptide or protein to which it is conjugated to the Golgi apparatus. Localization thus also implies retention in the Golgi apparatus. Typically, these localization (or retention) sequences are peptide sequences derived from (pre)proteins that are situated in the Golgi when functionally active as a mature protein.

The glycans and monosaccharides mentioned herein are sometimes indicated with their recognized abbreviations: e.g., Glc for β-D-Glucose, Man for β-D-Mannose, Gal for β-D-Galactose, GlcNAc for β-D-N-Acetylglucosamine, GalNAc for β-D-N-Acetylgalactosamine, NeuNAc for α-N-Acetylneuraminic acid, also known as sialic acid (Sia), Fuc for α-L-Fucose, Hex for hexose.

This disclosure aims to provide higher eukaryotic cells producing Fc-containing molecules with an altered glycosylation pattern, in particular, a more homogeneous glycosylation pattern, that makes them more amenable for further use, e.g., therapeutic use, or easier biomanufacturing.

This is achieved, according to a first aspect, by providing higher eukaryotic cells, particularly animal cells, with a first exogenous nucleic acid sequence encoding an endoglucosaminidase enzyme and a second exogenous nucleic acid sequence encoding an Fc-containing molecule.

According to particular embodiments, the higher eukaryotic cell is glyco-engineered to be deficient in synthesizing complex type sugars (and may or may not be engineered to be deficient in synthesizing hybrid type glycans). More particularly, the higher eukaryotic cell is a higher eukaryotic cell only capable of producing high mannose N-glycans. This can be achieved, e.g., by making the cell deficient in N-acetylglucosaminyltransferase 1 activity. According to particular embodiments, the glycosyltransferase GnTI, encoded by the gene MGAT1 (Gene ID: 4245 in humans), is inactivated in the cells.

Accordingly, higher eukaryotic cells incapable of synthesizing complex type or hybrid type N-glycans are provided, additionally characterized by having a first exogenous nucleic acid sequence encoding an endoglucosaminidase enzyme and a second exogenous nucleic acid sequence encoding an Fc-containing molecule. For example, higher eukaryotic cells deficient in N-acetylglucosaminyltransferase 1 activity are provided, additionally characterized by having a first exogenous nucleic acid sequence encoding an endoglucosaminidase enzyme and a second exogenous nucleic acid sequence encoding an Fc-containing molecule.

Higher eukaryotic cells can be of any higher eukaryotic organism, but in particular embodiments, mammalian cells are envisaged. The nature of the cells used will typically depend on the desired glycosylation properties and/or the ease and cost of producing the glycoprotein. Mammalian cells may, for instance, be used to avoid problems with immunogenicity. Higher eukaryotic cell lines for protein production are well known in the art, including cell lines with modified glycosylation pathways. Non-limiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, *Som. Cell Molec. Genet.*, 12:555-556; and Kolkekar et al., 1997, *Biochemistry* 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, *Proc. Natl. Acad. Sci. U.S.A.* 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, *Gen. Virol.* 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals N.Y. Acad. Sci.* 383:44-68); MCR 5 cells; FS4 cells. According to particular embodiments, the cells are mammalian cells selected from CHO cells, Hek293 cells or COS cells. According to further particular embodiments, the mammalian cells are selected from CHO cells and Hek293 cells.

It is particularly envisaged that the endoglucosaminidase enzyme produced by the higher eukaryotic cell will act on the Fc-containing molecule produced in the cell, and removes the N-glycosylation. According to particular embodiments, the endoglucosaminidase enzyme encoded by the first exogenous nucleic acid sequence is a mannosyl-glycoprotein endo-beta-N-acetylglucosaminidase, i.e., it has the activity of E.C. 3.2.1.96 in the IUBMB nomenclature, implying that it can remove sugar chains while leaving one GlcNAc residue on the protein (importantly, it also acts on the common core pentasaccharide $Man_3GlcNAc_2$). According to alternative embodiments, the endoglucosaminidase encoded by the first exogenous nucleic acid sequence has different affinities toward different types of glycosylation structures. Typical examples of the latter are endoglucosaminidases that are able to hydrolyze hybrid type sugars and/or high-mannose sugars, but are not capable of cleaving complex type glycans. According to further particular embodiments, the endoglucosaminidase is a mannosyl-glycoprotein endo-beta-N-acetylglucosaminidase that has different affinities toward different types of glycosylation structures. According to yet further particular embodiments, the endo-beta-N-acetylglucosaminidase is able to cleave hybrid-type sugars and/or high-mannose sugars, but not complex-type glycans. According to even more particular embodiments, the endoglucosaminidase is EndoH or EndoT. According to most particular embodiments, the endoglucosaminidase is Endo T.

To ensure that the endoglucosaminidase effectively removes the sugar chains of the Fc-containing protein, it is envisaged that the endoglucosaminidase not only remains in the cell, but is also fully active. Its activity should be regulated spatiotemporally in order to ensure that the desired hydrolysis takes place. Thus, according to particular embodiments, the expression of the endoglucosaminidase enzyme is targeted to the Golgi apparatus. This can be achieved by operably linking the endoglucosaminidase to a Golgi localization signal. Such signal directs the endoglucosaminidase to the Golgi, where it is retained. As the Golgi apparatus is, next to the ER, the intracellular location where glycosylation of proteins takes place, targeting to this organelle ensures that the endoglucosaminidase is in the correct intracellular position to modify the glycosylation of the glycoprotein.

This is particularly beneficial for controlling the further glycosylation, as the higher eukaryotic cells possess further enzymes needed for complex glycosylation that are also present in the Golgi secretory pathway. Indeed, the endoglucosaminidase can be targeted in such a way that these enzymes act cooperatively on the Fc-containing molecule. In higher eukaryotic cells, the luminal surface of the ER and Golgi apparatus provides catalytic surfaces that allow the sequential processing of glycoproteins as they proceed from the ER through the Golgi network into the medium. As a glycoprotein (such as the Fc-containing molecule) proceeds from the ER through the secretory pathway, it is sequentially exposed to different mannosidases and glycosyltransferases. Several processing steps rely on previous reactions because some N-glycosylation enzymes depend on a particular substrate that is created by the previous enzyme. N-glycosylation enzymes, in particular, exogenous enzymes such as the endoglucosaminidase, must, therefore, be arranged in a predetermined sequence to allow for the synthesis of specific N-glycan structures.

However, while the cells described herein are particularly useful to produce the desired Fc-containing molecules with the right glycosylation pattern, one should keep in mind that it is also possible to produce and add all or part of the desired sugar profile synthetically, in vitro (e.g., by enzymatic coupling on the produced (optionally deglycosylated) protein).

Establishing the sequential processing environments of the secretory pathway requires the proper localization of N-glycosylation enzymes. The mechanisms by which secreted proteins can be transported through the secretory pathway (from the ER to the cis-, medial- and trans-Golgi compartments and into the medium), while each compartment maintains a specific set of resident (for example, N-glycosylation) enzymes, has been the subject of extensive study. Two well-established mechanisms that localize proteins to the various compartments of the secretory pathway are retrieval and retention (van Vliet et al., *PBMB* 1 2003; Teasdale et al., 27 1996).

Retrieval is a process by which proteins are localized to certain organelles through interaction with other proteins. Several ER-residing proteins contain a carboxy-terminal tetrapeptide with the consensus sequence KDEL (SEQ ID NO:23) (or HDEL (SEQ ID NO:24) in yeast), which has been shown to be required for efficient localization to the ER.

Several ER- and Golgi-residing enzymes are type II membrane proteins. These proteins have a common domain structure comprising a short cytoplasmic tail at the amino terminus, a hydrophobic transmembrane domain, a luminal stem and a C-terminal catalytic domain. Deletion studies as well as fusions to non-Golgi-residing proteins have identified the N-terminus, and, in particular, the transmembrane region, as containing the targeting information of many type II membrane proteins. Although it is clear that N-terminal domains are involved in targeting, the extent to which their targeting ability is transferable between different species is not yet totally clear. Nevertheless, considerable advances have been made, such as the design of genetic libraries of known type II membrane protein domains that encode peptides that are associated with proteins that naturally localize to the ER and Golgi of *S. cerevisiae* or *P. pastoris* (Choi et al., 5022 (2003); Hamilton et al., *Science* 1244) confirming the suitability of, e.g., the leader sequence from *S. cerevisiae* Sec12 (ER localization), MNN2 (Golgi localization), and MNN9 (Golgi localization). Sequences listed in Table 5 of WO02/000879 include HDEL and the leader sequences from Mns1 for ER localization, and leader sequences from Och1 and Mnt1 (Golgi-cis localization), from Mnn2 (Golgi medial localization), from Mnn1 (Golgi trans localization), from alpha-2,6-sialyltransferase (trans-Golgi network) and from beta-1,4-galactosyltransferase I (Golgi localization).

Localization signals thus are well known in the art and may be derived from proteins that are normally localized in the ER or Golgi for their function. Moreover, localization sequences from one organism may function in other organisms. For example, the membrane spanning region of α-2, 6-sialyltransferase from rats, an enzyme known to localize in the rat trans Golgi, was shown to also localize a reporter gene (invertase) in the yeast Golgi (Schwientek, et al., 1995). Schwientek and co-workers have also shown that fusing 28 amino acids of a yeast mannosyltransferase (Mnt1), a region containing an N-terminal cytoplasmic tail, a transmembrane region and eight amino acids of the stem region, to the catalytic domain of human GalT are sufficient for Golgi localization of an active GalT (Schwientek et al. (1995), *J. Biol. Chem.* 270 (10): 5483-5489). Other well-documented motifs are the KDEL and HDEL motif for retention in the ER. According to particular embodiments, the ER or Golgi localization signal is from a protein that is itself localized in the ER or Golgi when functionally active. Examples of such proteins include, but are not limited to, *S. cerevisiae* dipeptidyl aminopeptidase A (Ste13p), human β-galactoside-α-2, 6-sialyltransferase (ST6GalI) and the human gangliosi de-GM2-synthase. According to further embodiments, the localization sequence is derived from one of the following proteins: Ste13p, GL2-synthase, ganglioside-GM2-synthase, and α-2,6-glycosyltransferase, in particular, α-2,6-sialyltransferase, most particularly β-galactoside-α-2,6-sialyltransferase.

Importantly, the Golgi apparatus is not just one homogeneous region, but has five functional regions: the cis-Golgi network, cis-Golgi, medial-Golgi, trans-Golgi, and trans-Golgi network. Vesicles from the endoplasmic reticulum (via the vesicular-tubular cluster) fuse with the cis-Golgi network and subsequently progress through the stack of cisternae that make up the Golgi apparatus to the trans-Golgi network, where they are packaged and sent to the required destination. Each region contains different enzymes that selectively modify the contents, e.g., depending on where they are destined to reside. Thus, depending on the exact targeting of the endoglucosaminidase within cells, glycosylation pathways may be modified in different ways.

While the endoglucosaminidase may be targeted late in the Golgi, to provide an "in vivo clean-up" of aberrantly glycosylated proteins, a particularly envisaged modification is targeting the endoglucosaminidase to an earlier stage in the Golgi glycosylation pathway, while one or more glycosyltransferases (typically endogenous glycosyltransferases in the case of higher eukaryotic cells, although exogenous glycosyltransferases are envisaged as well) are active further downstream. This way, a uniform glycopopulation (e.g., of single GlcNAc-modified Fc-containing molecules) is presented as substrate to the glycosyltransferases. This results in a uniform population of glycosylated Fc-containing molecules. Note that this uniform glycopopulation may particularly be a uniform population of non-naturally occurring glycoforms, as typical endoglucosaminidases will also remove the inner Man3GlcNAc2 core structure typical of natural glycostructures. However, such structures are often less immunogenic in mammals than particular glycans produced in plant, yeast or insect cells. As shown in the Examples section, a particularly envisaged targeting is targeting in the Golgi so that endogenous galactosyltransferase and sialyltransferase act sequentially on the protein, e.g., by targeting the endoglucosaminidase to the trans-Golgi. The sequential action of these enzymes yields trisaccharide structures on the produced Fc-containing molecules: a GlcNAc closest to the glycosylated asparagine residue, coupled to a Gal moiety and ending in a NeuNAc (sialic acid) moiety.

The Fc-containing molecules produced by the cells described herein typically should be easily recovered. This will particularly be achieved by secretion of the Fc-containing molecules. This may happen spontaneously, or by addition of a secretion signal. The nature of the secretion signal will typically not depend on the protein to be secreted, but on the type of higher eukaryotic cells used. As long as the secretion signal is functional in the cell type in which it is used (i.e., it results in secretion to the extracellular environment of the protein or peptide to which it is fused), this feature is not critical to the disclosure. Thus, secretion signals from other organisms may be used, as long as these signals lead to secretion in the higher eukaryotic cells used. Secretion signals are well known in the art and may be derived from—typically the N-terminus of—proteins that are secreted, or may be made synthetically (e.g., Tan et al., *Protein Engineering* 2002, vol. 15, no. 4, pp. 337-345). Alternatively, they can be derived from genomic sequences using computational methods (Klee et al., *BMC Bioinformatics* 2005, 6:256). Also, bacterial secretion signals can be used. Further examples of signal peptides that can be used are described in WO2002/048187 (eukaryotic cells), Schaaf et al. (*BMC Biotechnol.* 2005; 5: 30) (moss cells), EP549062.

The glycosylation status of the produced Fc-containing molecule will depend both on the cellular system used (e.g., which enzymes are present therein) and the specificity of the endoglucosaminidase. Moreover, the time and place where these enzymes act is also important (e.g., which enzyme acts first in the ER→Golgi pathway). The Fc-containing molecules produced in these cells can be further modified after production, e.g., by treatment with glycosyltransferases, resulting in proteins with the desired glycan moieties. However, it is particularly envisaged to use cells capable of producing Fc-containing molecules with specific glycan moieties, namely those with a GlcNAc-Gal-NeuNAc trisaccharide structure (with GlcNAc bound to the Asparagine residue of the Fc-containing molecule, in particular, the N297 residue of IgG Fc-containing molecules). Typically, this is achieved by eliminating the capacity for synthesizing complex sugars on the exogenous Fc-containing molecule (e.g., by eliminating N-acetylglucosaminyltransferase 1 activity), and targeting the exogenous endoglucosaminidase to the Golgi network, where it acts before the galactosyltransferase and the sialyltransferase. This eliminates the need for further glycosyltransferase treatment after production, as Fc-containing molecules with this specific sugar profile have beneficial properties. It is shown herein that molecules with this specific sugar structure are non-immunogenic, retain antigen binding, and have long-circulating half-life in vivo, while the simple glycosylation path results in a pool of proteins with much reduced heterogeneity in glycan profiles.

Thus, the higher eukaryotic cells described herein are particularly well suited for production of Fc-containing molecules. It is envisaged that Fc-containing molecules produced in these cells fall within the present scope.

Thus, according to particular embodiments, Fc-containing molecules are provided that are obtainable by producing them in higher eukaryotic cells, wherein the cells have:

A first exogenous nucleic acid sequence encoding an endoglucosaminidase enzyme;

A second exogenous nucleic acid sequence encoding the Fc-containing molecule.

According to further particular embodiments, the endoglucosaminidase enzyme is targeted to the Golgi apparatus (e.g., by operably linking it to a Golgi localization signal). According to alternative, non-exclusive embodiments, the higher eukaryotic cells are glyco-engineered to be incapable of complex-type glycosylation, while retaining expression of galactosyltransferase and sialyltransferase. According to specific embodiments, the glyco-engineering to be incapable of complex type glycosylation entails the inhibition or knock-down of N-acetylglucosaminyltransferase 1.

The Fc-containing molecules obtainable by producing them in these cells are Fc-containing molecules with a more homogeneous glycan profile compared to those produced in higher eukaryotic cells without the endoglucosaminidase (and with the capacity for complex glycosylation). However, most often, not all molecules will have the exact same trisaccharide sugar chain, as Fc-containing molecules that are incompletely glycosylated will also be produced. These forms carry either a single GlcNAc moiety, or a disaccharide Gal-GlcNAc (with GlcNAc linked to an asparagine of the Fc region). However, such population of identical Fc-containing molecules with trisaccharide, disaccharide or monosaccharaide structure described herein, also shows the beneficial effects. Thus, a plurality of Fc-containing molecules obtainable by producing them in these cells is also envisaged.

The beneficial properties of these molecules are not limited to those molecules produced in the cells described herein. As shown in the Examples section, the properties (in particular, the longer half-life in circulation) arise purely out of the specific glycosylation pattern. In other words, Fc-containing molecules that have the same glycosylation structure that is partly or wholly synthesized on the Fc-containing molecule in vitro (e.g., by treatment of endoglucosaminidase and/or glycosyltransferase(s)) will have the same properties as those produced completely in the cells described herein.

Thus, Fc-containing molecules are provided, characterized in that the glycosylation on asparagines in the Fc part consists of a glycan selected from the following: a trisaccharide structure Neu5Ac-Hex-HexNAc, a disaccharide structure Hex-HexNAc, and a monosaccharide structure HexNAc (each with HexNAc linked to the asparagine). More particularly, the glycosylation will be selected from the trisaccharide structure and the disaccharide structure. Most particularly, the glycosylation will be a trisaccharide structure Neu5Ac-Hex-HexNAc.

As a pool of these Fc-containing molecules with the three different glycosylation patterns also shows beneficial properties in vitro, a plurality of identical Fc-containing molecules are provided, characterized in that the glycosylation on asparagines in the Fc part consists of a glycan selected from the following: a trisaccharide structure Neu5Ac-Hex-HexNAc, a disaccharide structure Hex-HexNAc, and a monosaccharide structure HexNAc (each with HexNAc linked to the asparagine). Particularly, at least part of the plurality of Fc-containing molecules will have a glycosylation pattern selected from the trisaccharide structure and the disaccharide structure. Most particularly, at least part of the plurality of Fc-containing molecules will have a glycosylation that is a trisaccharide structure Neu5Ac-Hex-HexNAc.

Particularly envisaged HexNAc moieties are GlcNAc moieties. Particularly envisaged Hex moieties are Gal moieties. Thus, the Hex-HexNAc moiety in the above di- and trisaccharides particularly is a Gal-GlcNAc moiety. Most particularly envisaged is the trisaccharide Neu5Ac-α-2,3-Gal-β-1,4-GlcNAc, and the corresponding disaccharide Gal-β-1,4-GlcNAc.

Particularly envisaged Fc-containing molecules are molecules that contain an Fc from an immunoglobulin G (IgG). IgG Fc-containing molecules all have one conserved asparagine glycosylation site, indicated as N297 in human IgGs. Thus, IgG Fc-containing molecules described herein are characterized by the specific glycosylation pattern on that N297 residue.

Most (therapeutic) antibodies have no glycosylation sites in the Fab region. Likewise, most Fc-fusion proteins also have no further glycosylation sites. It is particularly envisaged that the glycosylation of the Fc region is the only glycosylation present in the Fc-containing molecule. Most particularly, it is envisaged that the glycosylation on N297 of IgG Fc-containing molecules is the only glycosylation present on the Fc-containing molecule. This will ensure that the modification of the glycosylation (of the Fc part) does not interfere with the interactions of the non-Fc part (e.g., the antigen binding of the Fab region).

According to particular embodiments, the Fc-containing molecule is an antibody or an Fc-fusion protein that binds an antigen. According to further particular embodiments, the Fc-containing molecule is an antibody, most particularly an IgG. It may be any one of an IgG1, 2, 3, or 4; but IgG1 and IgG2 antibodies are most prevalent.

When discussing the specific glycosylation of the present Fc-containing molecules, it is important to realize that these three sugar molecules are the only sugar molecules present on the Fc-containing molecule. In other words, these Fc-containing molecules do not have a core Man3GlcNAc2 moiety. This is an important difference with the prior art.

Indeed, stability of Gal-Sial structures have also been studied, but only when attached to the core Man3GlcNAc2 moiety, and as a bifurcated glycan (i.e., with 2 Gal-Sial antennae present). Moreover, these structures fixed to the core Man3GlcNAc2 have not been reported to prolong half-life; on the contrary, they are more sensitive to proteases (Raju et al., *Biotechnol. Prog.* 2007; 23(4):964-71)). This further highlights the surprising effect observed for the present, non-bifurcated trisaccharide structure.

Given that Fc-containing molecules are most often used as therapeutics, and that the Fc-containing molecules with the specific glycosylation presented herein have a longer half-life, without having altered antigen specificity (i.e., for those Fc-containing molecules that bind an antigen, such as all antibodies, and most Fc-fusion proteins), the present molecules are well suited for use in medicine.

Accordingly, Fc-containing molecules obtainable by producing them in higher eukaryotic cells as described herein are provided for use as a medicament. Also, Fc-containing molecules characterized by having a glycosylation on asparagines in the Fc part consists of a glycan selected from the following: a trisaccharide structure Neu5Ac-Hex-HexNAc, a disaccharide structure Hex-HexNAc, and a monosaccharide structure HexNAc (each with HexNAc linked to the asparagine), as described herein, are provided for use as a medicament.

These molecules can be used for any disorder wherein you normally would use Fc-containing molecules, particularly Fc-containing molecules that bind an antigen. Since they have the same binding affinity for the antigen as their non-glycosylation modified counterparts, they have the same applicability. Of note, as binding to Fcγ receptors is reduced by the specific glycosylation pattern, they may be less suitable for treating those diseases where binding of Fcγ receptors is important (e.g., Antibody-Dependent Cell-Mediated Cytotoxicity (ADCC) is thought to be mediated by Fcγ receptors, so the present molecules are likely less suited to elicit this response). On the other hand, they may be more suitable to treat those diseases where Fcγ receptor binding is not important or even not desired. Indeed, for antibodies that target cell-surface molecules, especially those on immune cells, abrogating effector functions is required. Abrogating Fcγ receptor binding proved useful in, e.g., treatment of fetomaternal alloimmunization to the human platelet alloantigen-1a (Armour et al., *Eur. J. Immunol.* 1999; 29(8):2613-24; Ghevaert et al., *J. Clin. Invest.* 2008; 118(8):2929-38), in treatment of autoimmune diseases or transplant rejection (Reddy et al., *J. Immunol.* 2000; 164(4):1925-33), in making a long-acting erythropoietin Fc-fusion protein (Yang et al., *Arch. Pharm. Res.* 2012; 35(5):757-9), and it is envisaged that the present molecules are particularly well suited for treating those disorders; i.e., methods of treating these diseases in subjects in need thereof are provided, comprising administering an Fc-containing molecule as described herein to the subjects.

The Fc-containing molecules are also particularly suited for those disorders wherein a longer circulating half-life of Fc-containing molecules is desirable, i.e., any disorder in which repeated administration of Fc-containing molecules is used as a therapy. One particular example of such therapy is IVIG: intravenous immunoglobulin, a plasma protein replacement therapy (IgG) for immune-deficient patients who have decreased or abolished antibody production capabilities. It is used in immune deficiencies, acquired compromised immunity conditions, autoimmune diseases, inflammatory diseases and acute infections.

Thus, the Fc-containing molecules described herein (particularly IgG molecules as described herein) are provided for use in intravenous immunoglobulin therapy. This is equivalent as saying that methods for treating subjects in need of intravenous immunoglobulin therapy are provided, comprising administering an Fc-containing molecule (IgG molecule) as described herein to the subjects.

Of note, a standard way of prolonging half-life of Fc-containing molecules is by increasing the affinity of the Fc-containing molecule for the FcRn receptor (e.g., the Xtend technology by XENCOR®). As the present way of prolonging half-life of Fc-containing molecules is independent of FcRn binding, the technologies are likely compatible to even further enhance half-life.

The eukaryotic cells described herein are particularly well suited for glycoprotein production. According to particular embodiments, the glycoproteins are enriched for a specific glycoform, particularly trisaccharide Neu5Ac-Hex-HexNAc-modified glycoproteins. Thus, methods are provided for producing Fc-containing molecules with a specific glycosylation pattern on asparagine residues in the Fc-containing molecule in a higher eukaryotic cell, comprising the steps of:

providing a higher eukaryotic cell comprising a first exogenous nucleic acid sequence encoding an endoglucosaminidase enzyme, wherein the endoglucosaminidase is operably linked to a Golgi localization signal, and a second exogenous nucleic acid sequence encoding the Fc-containing molecule, in conditions suitable for expressing the endoglucosaminidase enzyme and the Fc-containing molecule; and recovering the Fc-containing molecule after it has been intracellularly contacted with the endoglucosaminidase.

The same considerations for the cells and Fc-containing molecules apply as described above. According to a particular aspect, the protein modified with the single GlcNAc residue, obtained after the contacting with the endoglucosaminidase, is only an intermediary product. Methods according to this aspect will include at least one additional transglycosylation step. Although this transglycosylation can be done extracellularly (via an added enzyme or via an enzyme also produced by the cells), it is particularly envisaged that transglycosylation occurs intracellularly, by glycosyltransferases expressed by the higher eukaryotic cells. According to these embodiments, before the final recovery of the glycoprotein, the methods further involve a step of contacting the enzyme with one or more glycosyltransferases after it has been intracellularly contacted with the endoglucosaminidase. It will be understood by the skilled person that, when both the endoglucosaminidase enzyme and the one or more glycosyltransferase enzyme(s) are targeted to the (ER or) Golgi, it is ensured that the glycosyltransferase activity occurs after the endoglucosaminidase activity. Typically, this may be ensured by targeting both enzymes to different compartments of the ER or Golgi, as there is a fixed order in which proteins follow the ER→Golgi route. In the event both enzymes are targeted to the same compartment, or that both activities are performed by the same enzyme, it typically will be ensured that the protein after the transglycosylation step is no longer recognized as substrate for the endoglucosaminidase enzyme. Thus, separation of the enzymatic activities in time may also involve spatial separation and/or a different substrate specificity and/or inactivation of the enzyme.

The glycosyltransferase may be encoded by an exogenous sequence, or may be an enzyme that is endogenous in the cells having a first exogenous nucleic acid sequence encoding an endoglucosaminidase enzyme and a second exogenous nucleic acid sequence encoding an Fc-containing molecule.

It is particularly envisaged that the Fc-containing molecule is secreted to allow easy recovery.

A particular class of Fc-containing molecules described herein are Fc-containing molecules that bind to an antigen (typically antibodies, or Fc-fusion proteins that wherein the Fc region is fused to a binding moiety). These molecules retain antigen binding activity and have increased circulation time in vivo compared to non-modified glycoforms.

Accordingly, in a further aspect, methods are provided for increasing circulation time of an Fc-containing molecule that binds to an antigen, to be administered to a subject in need thereof, without altering antigen binding, comprising:
  providing an Fc-containing molecule with a specific trisaccharide Neu5Ac-Hex-HexNAc-modified glycosylation pattern;
  administering the Fc-containing molecule to the subject.

It is to be understood that although particular embodiments, specific configurations as well as materials and/or molecules, have been discussed herein for cells and methods according to this disclosure, various changes or modifications in form and detail may be made without departing from the scope and spirit of this disclosure. The following examples are provided to better illustrate particular embodiments, and they should not be considered limiting the application. The application is limited only by the claims.

EXAMPLES

Example 1

Generation of a Stable Cell Line with Altered Glycosylation

Figure 1A:
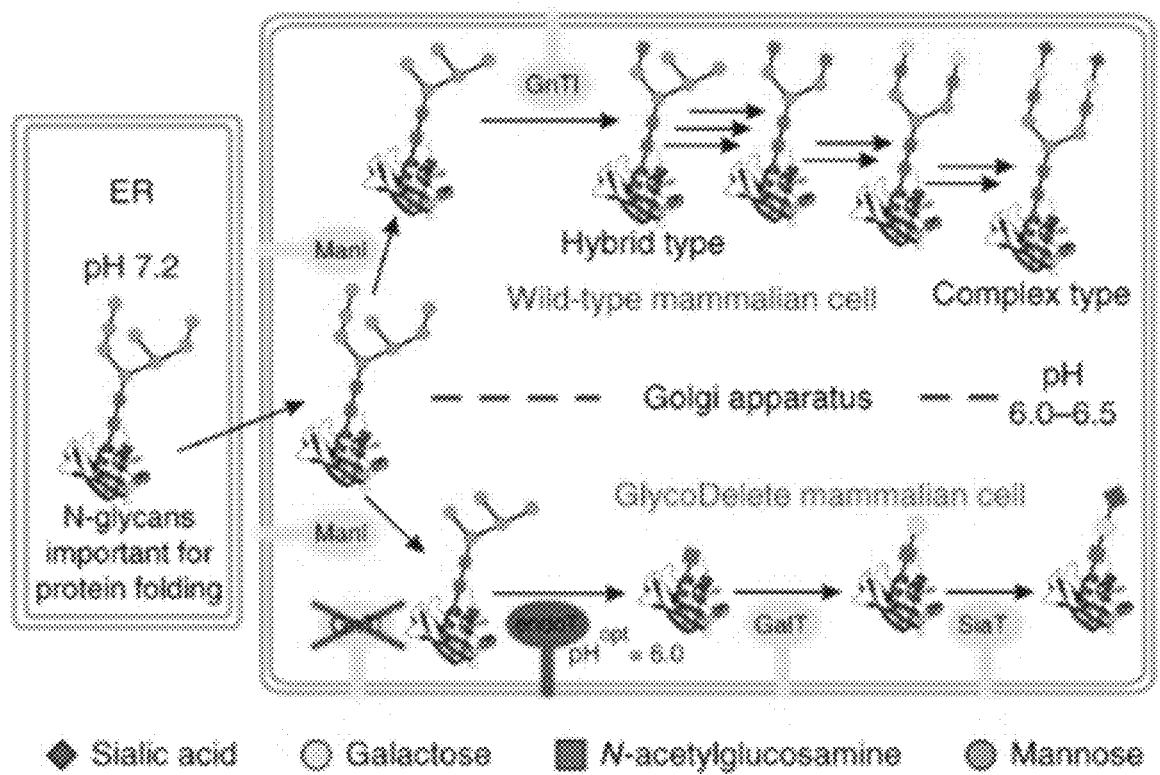
FIGS. 1A-1D: The GlycoDelete strategy and cell line characterization. Sugar residues: blue square, N-acetylglucosamine; green circle, mannose; yellow circle, galactose; purple diamond, sialic acid.

Glycoproteins produced in mammalian cells are often heterogeneous as a consequence of the many biosynthetic steps of complex-type N-glycan synthesis (FIG. 1A). Each step is less than 100% efficient and some enzymes compete for substrates, resulting in many different glycoforms. Therapeutic glycoprotein heterogeneity negatively impacts downstream processing and process reproducibility and can lead to variable efficacy since glycans affect clearance and biological activities.[1, 2] For instance, the sialic acid content of the glycans often determines pharmacokinetics.[3] In tackling the glycan heterogeneity problem, it has to be considered that N-glycans are often critical for protein folding and cannot be simply removed through N-glycosylation site mutagenesis. Here, we introduce a mammalian cell glycoengineering technology that shortcuts the Golgi N-glycosylation pathway to produce proteins with minimal-sized sialylated trisaccharide N-glycans (FIG. 1A).

293SGnTI-/- cells[4] produce glycoproteins modified with $Man_5GlcNAc_2$ N-glycans. Several endo-β-N-acetylglucosaminidases[5] are known that hydrolyze such glycans, upon which a single asparagine-linked N-acetylglucosamine (GlcNAc) residue is left. EndoT[6] was chosen as a eukaryotic-origin representative of this Glycoside Hydrolase family 18 for expression in the mammalian cell secretory system as it has the advantage that the pH optimum of endoT is 6.0. This is close to the pH in the mammalian trans-Golgi apparatus,[7] but sufficiently different from the pH in the ER (pH 7.2), so as not to interfere substantially with the ER-function of N-glycans in protein folding and quality control. Earlier, it was shown that transient Golgi-targeted expression of endoT in 293SGnTI-/- cells results in in vivo de-N-glycosylation of glycoproteins (e.g., Examples 6 and 7 of EP2331701).

EndoT hydrolysis in the Golgi would produce single GlcNAc N-glycan "stumps" on the glycoproteins, post folding. It was speculated that such Golgi-generated single GlcNAc residues would be recognized by the cell's galactosyltransferases and sialyltransferases, prior to secretion. This would then result in the synthesis of the most simple sialylated type II termini, a common element in N- and O-glycans. This three-step pathway is much shorter than the many-step native N-glycosylation pathway and should result in strongly reduced heterogeneity and easier N-glycan characterization. The glycoengineering strategy described above, "GlycoDelete," is illustrated in FIG. 1A.

Figure 3A:
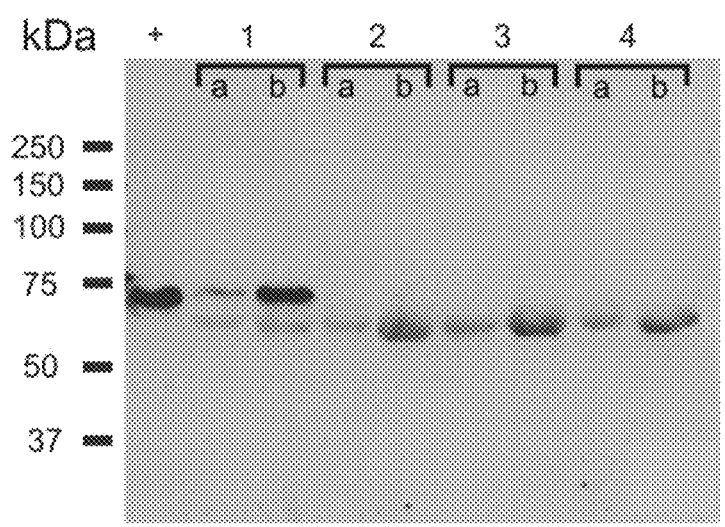
FIGS. 3A and 3B: In vivo de-N-glycosylation by transient transfection of the endoT fusion constructs. To evaluate the de-N-glycosylation by the endoT fusion proteins, the fusion constructs were transiently transfected to 293 SGnTI–/– cells that stably and inducibly expressed the Flt3 receptor extracellular domain (Flt3ECD, FIG. 3A) or to 293 SGnTI–/– cells stably and inducibly expressing the 5-hydroxy-tryptamin receptor 1D (5HT1D, FIG. 3B). Samples were analyzed by immunoblotting to detect the C-terminal HIS-tag (FIG. 3A) or the C-terminal Rho1D4 tag (FIG. 3B). The numbers in both
Figure 3B:
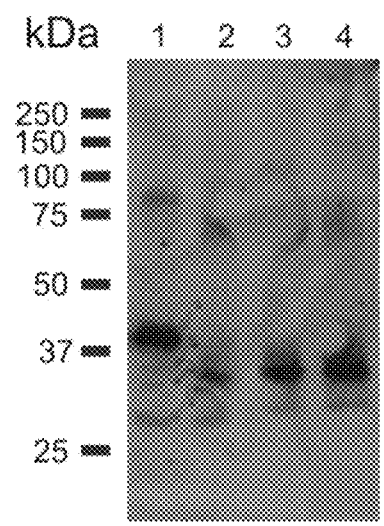

In order to target endoT to the trans Golgi of 293SGnTI-/- cells, the endoT-encoding sequence was fused without its predicted signal sequence to Golgi targeting domains from two human enzymes normally present in the Golgi (FIG. 2). When the endoT catalytic domain was fused to the targeting domain of the human β-galactoside-α-2,6-sialyltransferase 1 (ST6GAL1)[8] (referred to herein as the ST-endoT fusion protein), it was retained intact in the cells. Transient expression of ST-endoT in 293 SGnTI(-) cells resulted in in vivo deglycosylation of a stably expressed and secreted Flt3 receptor extracellular domain[9] and the human 5-hydroxytryptamin 1D (5HT1D) receptor (FIGS. 3A and 3B).

Figure 1B:
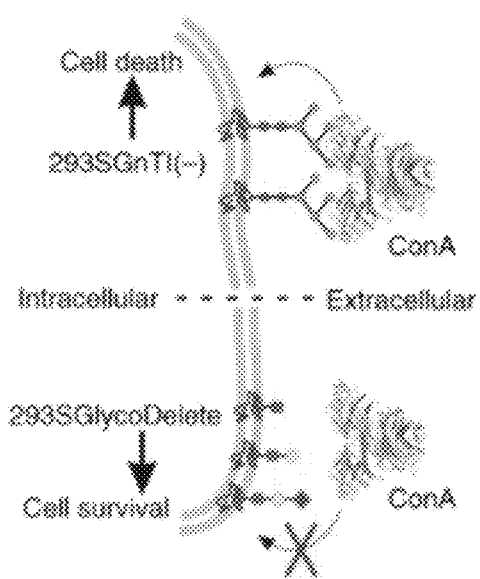
Figure 1C:
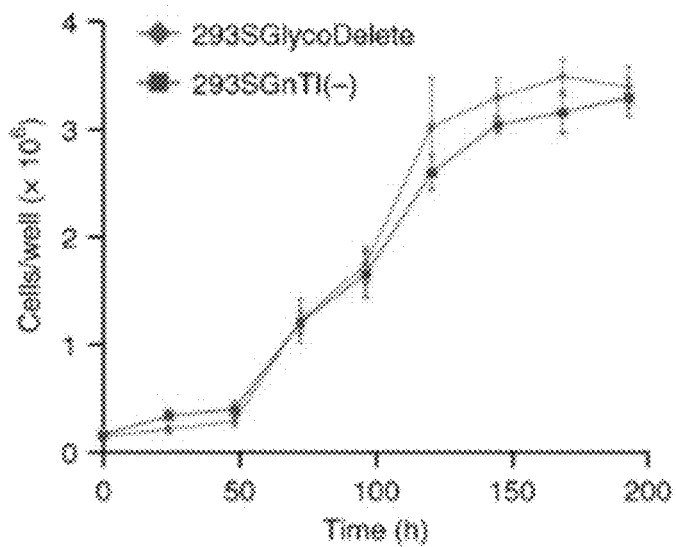
Figure 4:
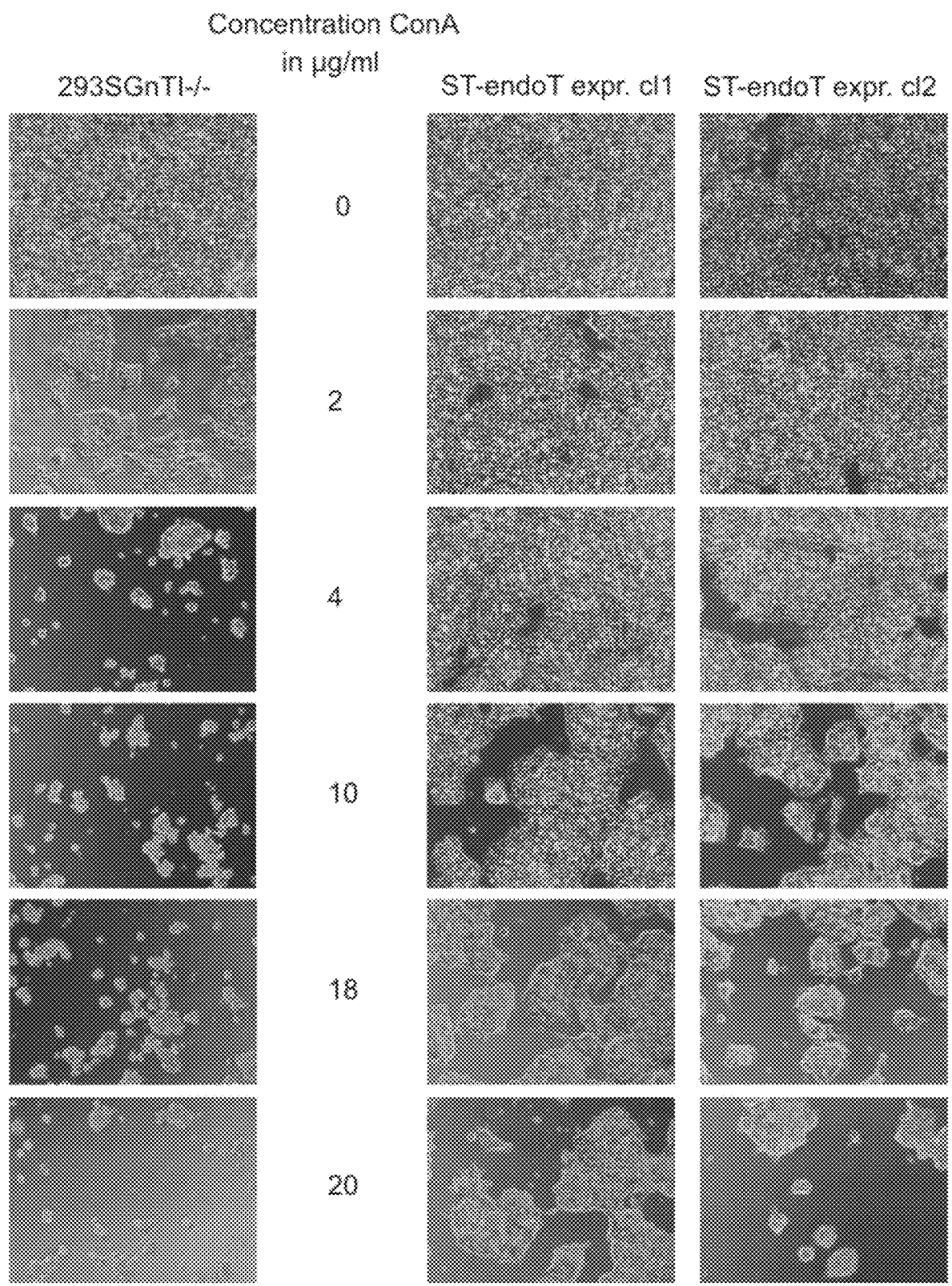
FIG. 4: ConA sensitivity assay[2] for two ST-endoT overexpressing clones and the parental 293 SGnTI–/– line. A lectin sensitivity assay was performed to determine the ConA sensitivity of 293SGnTI–/– cells and two endoT overexpressing clones. Both clones were much more resistant to ConA than the parental line (293 SGnTI–/–: 2 µg/ml). However, the first clone was more resistant to ConA (>22 µg/ml) than the second clone (18 µg/ml), and was thus selected for further work. It was designated 293 SGlycoDelete. The stability of 293 SGlycoDelete line resistance to ConA was tested over 20 splits (#+8 vs. #+28). Resistance/ sensitivity was found to be stable and >20 μg/ml (data not shown). Higher concentrations than about 20 μg/ml could not be tested, because aggregates started to form.

To establish a 293SGnTI(-)-derived cell line stably expressing ST-endoT fusion protein, cells were selected with the desired glycan phenotype using concanavalin A (ConA). ConA is a tetrameric cytotoxic lectin that binds to oligomannose and hybrid-type N-glycans. Full deglycosylation of cell surface glycoproteins by endoT would result in the absence of ConA ligands, thus rendering the cells resistant to this lectin (FIG. 1B). Four weeks after transfection, clones resistant to ConA (at the lowest concentration that killed all of the parental 293SGnTI(-) cells) were obtained. Two clones were selected for robust growth and subjected to a ConA lectin sensitivity assay,[10] and that with the highest ConA resistance was named 293SGlycoDelete (FIG. 4). Genomic integration and expression of ST-endoT were validated by PCR and immunoblotting, respectively (FIGS. 5A and 5B). 293SGlycoDelete and 293SGnTI(-) cells have similar morphologies, and their growth rates are indistinguishable (FIG. 1C). However, it was noticed that 293SGlycoDelete cells are less adherent than 293SGnTI(-) cells; this is a desirable feature for suspension cultivation, as used in biopharmaceutical production.

Figure 1D:
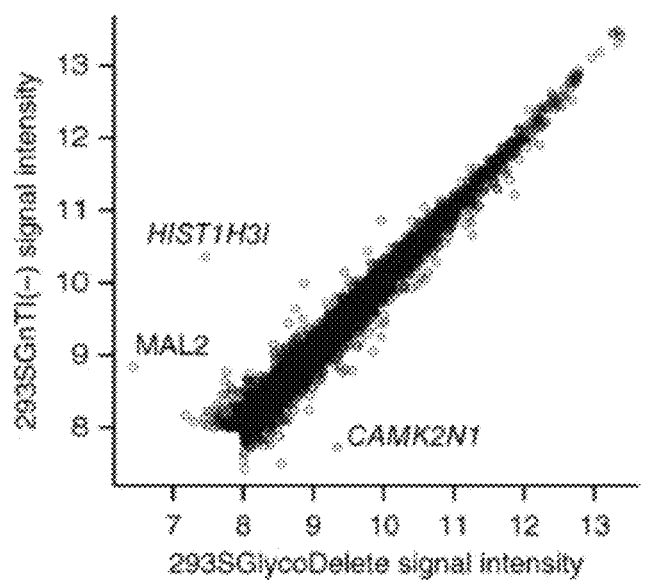

The transcriptomes of 293SGnTI(-) and 293SGlycoDelete cells were profiled using exon microarrays and it was found that only three of the 7,344 genes that had detectable expression were more than two-fold differentially expressed (P<0.01) between the two cell lines (FIG. 1D). Comparison of the 293SGnTI(-) line and the 293S parent showed differential transcription of about 70 genes (FIGS. 6A and 6B), without clear enrichment for particular pathways. Substantial genomic rearrangement was observed in the 293SGnTI(—) line (unpublished observations), which may account for these differences. Therefore, GlycoDelete engineering does not substantially alter the transcriptional profile of the cells. The absence of a transcriptional signature of the unfolded protein response[11] in the 293SGlycoDelete cells demonstrates that the GlycoDelete strategy does not noticeably interfere with the role of N-glycans in quality control in the endoplasmic reticulum.

Example 2

The GlycoDelete Cell Line is Suitable for Expression of Glycoproteins with Reduced Heterogeneity and Length of N-Glycans, without Affecting Protein Function The effect of stable GlycoDelete engineering was assessed on a transiently overexpressed, secreted cytokine (the human granulocyte/macrophage colony stimulating factor, hGM-CSF[13]), on a stably overexpressed GPCR, the 5HT1DR[12] (Example 3), on a transiently overexpressed monoclonal antibody (anti-CD20, obinutuzumab)[14] (Example 4) and on a transiently overexpressed Fc-containing fusion protein (anti-TNF, etanercept) (Example 5).

Furthermore, GM-CSF was transiently expressed in 293S, 293 SGnTI–/– and 293 SGlycoDelete cells and purified from the culture medium. GM-CSF produced in 293S or 293 SGnTI–/– cells consists of three main glycoforms (corresponding to occupancy of zero, one or two N-glycosylation sites),[15] which are converted to a form of the protein with a lower molecular weight (MW) by treatment with peptide-N-glycosidase F (PNGaseF), which cleaves the N-glycosidic bond between the asparagine side chain and N-glycans that contain at least the chitobiose core (FIG. 7A). The remaining heterogeneity is due to O-glycosylation,[15] as indicated by its partial disappearance upon sialidase digestion. In contrast, a lower MW range was observed for the GM-CSF purified from 293SGlycoDelete cells (FIG. 7A). PNGaseF treatment of the GlycoDelete GM-CSF did not cause any change in the observed pattern, demonstrating the absence of chitobiose-core containing N-glycans. Treatment with sialidase caused a shift in the MW of the GlycoDelete GM-CSF, more so than in the case of GM-CSF from 293S or 293SGnTI–/– cells, indicating the presence of more sialic acid residues on GlycoDelete GM-CSF than on the other forms (FIG. 7A). This conclusion was also supported by glycan analytics, described below (FIGS. 7B, 8 and 9). After digestion with PNGaseF and sialidase, GM-CSF from all three cell lines ran as single bands with indistinguishable mobility (it should be noted that these gels do not resolve nonglycosylated proteins from those modified with the small GlycoDelete N-glycan stumps), supporting the conclusion that the differences between GM-CSF from 293S, 293SGnTI(–) and 293 SGlycoDelete cells were due to glycosylation differences; this was confirmed by mass spectrometric analysis of the intact proteins (FIG. 10).

To further characterize the N-glycans on GM-CSF from 293SGlycoDelete and 293SGnTI(–) cells, the samples were analyzed by matrix-assisted laser desorption ionization (MALDI)—mass spectrometry (FIGS. 7B and 8). Analysis of 293S GM-CSF glycans by capillary electrophoresis (FIG. 9) revealed a typical heterogeneous mixture of multi-branched complex-type glycans. The level of sialylation was low, probably owing to the rapid transfer of the cells to serum-free medium during protein production. The glycopeptide containing N37 of 293SGnTI(–) GM-CSF was detected as a Man5GlcNAc2(Fuc) N-glycosylated peptide (FIG. 7B, top), in agreement with previous findings.[4, 16] These ions are absent from the spectrum of GM-CSF produced in 293SGlycoDelete cells, in which three new glycopeptide masses were detected. These masses are consistent with N-acetylhexosamine (HexNAc) glycopeptide, Hex-HexNAc glycopeptide and N-acetylneuraminic acid (Neu5Ac)-Hex-HexNAc glycopeptide (FIG. 7B). Similar observations were made for the glycopeptide containing N27 (FIG. 8).

To confirm the identity and linkage of the hexose and Neu5Ac units on GlycoDelete GM-CSF glycopeptides, exoglycosidase digests were performed with an α-2,3-/α-2,6-/α-2,8-sialidase and β-1,4-galactosidase (FIG. 7B). This allowed establishment that the di- and trisaccharide modified peptides are Gal-β-1,4-GlcNAc and Neu5Ac-α-2,3-Gal-β-1,4-GlcNAc, respectively. The presence of these glycans—not just the single GlcNAc endoT digestion product—on proteins produced in the GlycoDelete cells shows that galactosyltransferases and sialyltransferases in the Golgi act on the GlcNAc stumps generated by endoT. This confirms that endoT deglycosylation of GM-CSF must have occurred intracellularly and not after secretion. Quantification of the relative peak intensities of the protein spectra before and after sialidase treatment indicated that ~75% of glycans on GM-CSF from GlycoDelete cells were sialylated.

The influence of the GlycoDelete glycan alteration on properties of GM-CSF was then investigated. A Thermo-Fluor assay[17] showed that the melting temperatures of GM-CSF from *Escherichia coli* (nonglycosylated, Tm=58.9±0.6° C.), 293S cells (complex type N-glycosylation, Tm=61.2±3.2° C.) and 293SGlycoDelete cells (Tm=61.5±0.2° C.) were not significantly different (Kruskal-Wallis test, n=4, P>0.05; mean±s.d.) (FIG. 7C). Furthermore, in a TF1 human erythroleukemia cell—proliferation assay[18] (FIG. 7D), the bioactivity of GM-CSF from 293S and 293SGlycoDelete cells was highly similar.

To assess whether GlycoDelete glycans contribute to the antigenicity of GM-CSF, rabbits were immunized with GM-CSF from 293SGlycoDelete cells. Binding of serum antibodies to undigested, sialidase-treated or sialidase- and galactosidase-treated 293SGlycoDelete GM-CSF was determined by ELISA. GM-CSF from which the GlycoDelete glycan structures had been removed and GM-CSF with the GlycoDelete glycans present were recognized equally well, indicating that the GlycoDelete glycans did not form new immunogenic epitopes on GM-CSF in rabbits (FIGS. 7E and 7F).

Example 3

The GlycoDelete Cell Line is Suitable for Stable Expression of Glycoproteins with Reduced Heterogeneity and Length of N-Glycans To confirm that GlycoDelete is compatible with stable transfection-based protein production and that it can process membrane proteins, a stable cell line was generated in which, next to the stable GlycoDelete engineering, a GPCR, the 5HT1DR,[12] was stably overexpressed. Treatment of membrane protein extracts with PNGaseF revealed a large shift in the molecular weight (MW) of the 5HT1DR stably overproduced in 293SGnTI–/– cells. Contrary to this, whether or not treated with PNGaseF, the receptor produced in 293SGlycoDelete cells ran at approximately the same MW as PNGaseF-treated receptor from 293SGnTI–/– cells. It was concluded that, in 293SGlycoDelete cells, ST-endoT completely hydrolyzed the 5HT1DR N-glycans (FIG. 11).

Example 4

Antibodies Produced by the GlycoDelete Cell Line have the Same Affinity for their Ligand, but Longer Circulation Times In Vivo To further explore the scope of GlycoDelete technology, the monoclonal anti-CD20 antibody obinutuzumab (GA101)

14 was transiently expressed in 293S and 293SGlycoDelete cells and purified from the cell culture medium. The cell lines produced similar amounts of the antibody (FIG. 12). 293S-produced anti-CD20 carries core-fucosylated biantennary N-glycans typical of IgGs[19] on its only Fc-linked N-glycosylation site (N297 in the heavy chain Cγ2-domain) (FIG. 13). As expected, treatment with PNGaseF reduced the MW (FIG. 14A). In contrast, the heavy chain of the antibody produced in 293SGlycoDelete cells ran at approximately the same MW as the heavy chain of the PNGaseF-treated antibody from 293S cells, and the MW was not further reduced by PNGaseF treatment (FIG. 14A). This result is consistent with the N-glycans on this IgG having been cleaved by endoT. Thus, the GlycoDelete cells also process hIgG Fc-linked N-glycans.

To further characterize the glycans on 293SGlycoDelete anti-CD20, the different glycoforms of the tryptic IgG peptide containing the N-glycosylation site were quantified using liquid chromatography—electrospray ionization mass spectrometry (LC-MS/MS) in selected reaction monitoring (SRM) mode (FIG. 14B). Furthermore, LC-MS analysis of the intact antibody was performed with and without dissociation of the chains through reduction (FIGS. 15A-15C). The LC-MS/MS analysis revealed that the GlycoDelete protein was modified with HexNAc, Gal-HexNAc and Neu5Ac-Gal-HexNAc N-glycans, as also observed for GM-CSF. Quantification of the relative glycopeptide peak areas of samples before and after sialidase treatment allowed establishment that 19% of the anti-CD20 carries the sialylated trisaccharide and 72% carries the Gal-GlcNAc disaccharide, the remainder being the GlcNAc-modified peptide. In SRM-mode LC-MS/MS peptide analysis, the Hex5-HexNAc2 glycopeptide that is dominant in 293 SGnTI(-) IgG was below the detection limit for 293SGlycoDelete IgG. Intact protein LC-MS analysis revealed a very small remaining fraction of the Hex5-HexNAc2 glycoform, both in 293S- and 293SGlycoDelete-produced antibodies. The amount of Hex5HexNAc2 in both preparations was quantified at 2.5% of the total glycan pool by DNA-sequencer carbohydrate electrophoresis of a 1:1 mixture of both antibodies (data not shown).

In addition, flow cytometric analysis of binding to CD20+ cells showed that GlycoDelete anti-CD20 antigen binding was identical to that of 293S anti-CD20 (FIG. 14C), demonstrating that the antigen-binding fold was unaffected.

As N-glycans make up part of the fold packing contacts in the Cγ2 domain, size reduction of these glycans is expected to lead to a drop in Tm. Accordingly, the Tm for Cγ2 is ~64° C. for complex-type N-glycosylated 293S anti-CD20 and 57° C. for 293SGlycoDelete anti-CD20, similar to the Tm for PNGaseF-digested 293S anti-CD20 (FIG. 14D). No evidence was found of aggregation of anti-CD20 expressed by 293S or 293SGlycoDelete cells by gel filtration chromatography (FIG. 16).

Glycosylation on heavy chain N297 has a major influence on the affinity of binding of antibodies to Fc-γ receptors (FcγRs)[20], so the binding of 293S and 293SGlycoDelete anti-CD20 to different human FcγRs was assessed. Surface plasmon resonance experiments (Table 1) showed that the human and mouse neonatal FcRs (FcRns) have similar affinities for both anti-CD20 glycoforms. This is expected because the FcRn binding site is not located near the Cγ2 N-glycan site (Roopenian et al., 2007). A competition ELISA was set up for FcγRI, FcγRIIa and FcγRIIb in which the anti-CD20 antibodies compete in solution for FcγR binding with a precoated IgG. In all three cases, a >10-fold reduction in binding competition by 293SGlycoDelete anti-CD20 compared to the 293S anti-CD20 was detected (FIG. 14E). FcRIIIa binding affinity, as assessed by biolayer interferometry (Table 1), was 5.8 times lower for 293SGlycoDelete anti-CD20 than for 293S anti-CD20. Similarly, in an antibody-dependent cell-cytotoxicity (ADCC) assay using natural killer (NK) cells as effectors (FIG. 14E), it was found that the half-maximal effective concentration (EC50) of the specific lysis with 293SGlycoDelete anti-CD20 is 6.6 times higher than with 293S anti-CD20. Overall, the GlycoDelete glycosylation of human IgG1 Fc leads to reduced binding to FcγRs; in the context of producing neutralizing antibodies, this might be desirable to improve safety (Lux et al., 2013).

TABLE 1

Dissociation constants ($K_D$) of the Fc binding with hFcRn, mFcRn and FcγRIIIaV

|  | GlycoDelete | 293S | $K_D$ fold reduction |
| --- | --- | --- | --- |
| hFcRn | 6.72E−09 | 5.60E−09 | 0.83 |
| mFcRn | 2.24E−10 | 2.58E−10 | 1.15 |
| FcγRIIIaV | 2.90E−06 | 5.00E−07 | 5.8 |

Both hFcRn and mFcRn binding was determined with SPR and a $K_D$ for both glycoforms were found within the same range. IgG binding to FcγRIIIaV was determined using BLI. KD of 293SGlycoDelete cells is reduced with a factor 5.8 compared to the WT glycoform.

To assess whether GlycoDelete glycans on the IgG are immunogenic, a similar immunization experiment as for GM-CSF was performed (FIG. 14F) and concluded that GlycoDelete glycans do not substantially contribute to antigenicity of the anti-CD20 molecule.

Remarkably, pharmacokinetics analysis in mice showed that the initial rapid clearing phase (1 hour post-injection) removed substantially less of the GlycoDelete anti-CD20 from circulation, leading to doubled long-term circulation levels. Both glycoforms were subsequently cleared at an equivalent (slow) rate (FIGS. 14G and 17), as was anticipated from their similar FcRn affinity. Owing to the initially higher level, it, therefore, would take 10-12 days longer for the concentration of the GlycoDelete antibody to drop below a required therapeutic threshold concentration. This means that considerably higher levels of the GlycoDelete anti-CD20 remained in vivo for a much more prolonged time period. A possible mechanism is that higher sialylation leads to lower clearance through reduced binding to liver and macrophage lectin receptors. Potentially, the sialylation levels of GlycoDelete IgG could be further enhanced, and this observation suggests that GlycoDelete IgGs might allow a reduced frequency of dosing for neutralizing therapeutic IgGs that often require long circulation periods in the blood.

Example 5

Chimeric Fc-Containing Molecules Produced by the GlycoDelete Cell Line Also have More Homogenous Glycosylation Patterns Next, etanercept, a recombinant fusion protein consisting of the human type 2 TNF receptor fused to the constant end of the IgG1 antibody, was transiently expressed and purified in GlycoDelete cells. Similar to the proteins tested in Examples 2 and 4, LC-MS analysis revealed that the Fc part of the GlycoDelete protein was modified with HexNAc, Gal-HexNAc and Neu5Ac-Gal-HexNAc N-glycans (FIG. 18). (This was evaluated with the EQQYNSTYR peptide (SEQ ID NO:1) from the Fc chain.)

Subsequent sialidase and galactosidase digest further confirmed the identity of these sugar groups (FIG. 18). Quantification of the relative glycopeptide peak areas of samples before and after sialidase and galactosidase treatment allowed establishment that 25% of etanercept produced in these cells has an Fc chain carrying the sialylated trisaccharide and 68% carries the Gal-GlcNAc disaccharide, the remainder being the GlcNAc-modified peptide (Table 2). These percentages are in good agreement with those observed for the anti-CD20 antibody, indicating that the glycosylation of Fc chains in the cells is quite uniform.

TABLE 2

LC-MS area under the curve of the Fc-glycopeptide on etanercept in three replicated measurements (one of which is shown in FIG. 18):

| | Area under the curve | | | | |
|---|---|---|---|---|---|
| | Pep | Pep-GlcNAc | Pep-GlcNAc-Gal | Pep-GlcNAc-Gal-Sial | Pep-Man5 |
| peptide | 2044 | 22361 | 267000 | 19712 | 36 |
| | 2127 | 18806 | 243015 | 20823 | 10 |
| | 1865 | 16690 | 228098 | 18072 | 15 |
| avg | 2012 | 19286 | 246038 | 19536 | 20 |
| Peptide + sialidase | 1640 | 13989 | 257195 | 15 | 15 |
| | 1051 | 13234 | 233126 | 46 | 20 |
| | 4608 | 14247 | 236880 | 76 | 10 |
| avg | 2433 | 13823 | 242400 | 46 | 15 |
| Peptide + sialidase + galactosidase | 6752 | 373558 | 22399 | 18 | 36 |
| | 7191 | 368247 | 21963 | 20 | 10 |
| | 6640 | 355005 | 20120 | 10 | 15 |
| avg | 6861 | 365603 | 21494 | 16 | 20 |

In the Table, it can be seen that only trace amounts of the original mannose-5 glycan are found back in the etanercept sample. 25% of the Fc chain carries the GlcNAc-galactose-sialic acid trisaccharide, 68% carries the GlcNAC-galactose disaccharide and the remainder is single GlcNAc glycosylated.

Conclusion

In conclusion, this study introduces the GlycoDelete glycoengineering strategy as an approach to solving the issue of N-glycosylation heterogeneity in mammalian cell-based glycoprotein production. GlycoDelete involves the optional, but particularly envisaged, inactivation of a single glycosyltransferase (GnTI, encoded by the gene MGAT1) and overexpression of a deglycosylating enzyme, followed by lectin selection. GlycoDelete cells produce proteins with the Gal-GlcNAc disaccharide or its α-2,3-sialylated trisaccharide derivative and some of the monosaccharide intermediate. This is in contrast to the dozens of glycan structures produced by wild-type mammalian cells. The GlycoDelete strategy strikes a balance between retaining the folding-enhancing functions of N-glycans and avoiding the extensive heterogeneity introduced through mammalian Golgi N-glycan processing. In addition to the advantages of reduced N-glycan complexity in biopharmaceutical manufacturing, examples of the therapeutic benefit of similar short, simple N-glycans generated in vitro have been reported.[21-23] Furthermore, it has been shown that GlycoDelete engineering favorably alters the characteristics of antibodies when the therapeutic goal is antigen neutralization without the need for additional effector function. Therefore, GlycoDelete could lead to "biobetters," an area of interest in the biopharmaceutical industry.[28] The strategy appears to be particularly well suited for expression of Fc-containing molecules, since it prolongs circulating half-life just by altering the glycosylation of the conserved N297 residue. This has important therapeutic advantages for, e.g., therapeutic IgG injections, which can be done much less frequently (e.g., half as frequently) while retaining the same efficacy because of the same affinity for the ligand.

Material and Methods

General Cell Culture and Transfection.

293SGnTI(−) cells were maintained in a humidified incubator at 37° C. and 5% CO2 in DMEM/F12 (Gibco) with 10% FBS, 292 µg/mL L-glutamine, 100 units/mL penicillin and 100 µg/mL streptomycin (all Sigma-Aldrich).

For small-scale transfections, the cells were plated in a six-well plate 48 hours before transfection at ~150,000 cells per well. They were transfected using the TransIT-293 Transfection Reagent (Mirus Bio LLC) according to the manufacturer's instructions. For transient or large-scale transfections, cells were transfected with the calcium phosphate transfection method. Raji cells were cultured in RPMI 1640+10% FBS+2 mM L-Glutamine.

All cell lines were routinely tested for mycoplasma contamination with the Plasmotest kit (InvivoGen).

Transient EndoT Expression.

The endoT fusion constructs (pCAGGS-GM2S-endoT and pCAGGS-ST-endoT) and the secreted endoT construct (pCAGGS-s-endoT) were transiently transfected to 293SGnTI(−) cells as described above. Supernatant and cell lysate samples were analyzed to assess targeting domain performance (FIG. 2).

In Vivo De-N-Glycosylation by Transient Transfection of EndoT-Fusions

De-N-glycosylation by endoT was evaluated by transfecting all endoT constructs to 293SGnTI(−) cells stably and inducibly expressing the Flt3 receptor extracellular domain (FIGS. 3A and 3B).

Construction of the Plasmid for Stable ST-EndoT Expression (pcDNA3.1(−)Zeo-ST-endoT).

The ST-endoT PCR fragment was cloned into a pCR®II-TOPO® plasmid (Life Technologies). The resulting Topo-ST-endoT plasmid (reverse complement insertion) was digested with XhoI and KpnI and the insert was purified. The pcDNA3.1/zeo(−) plasmid was digested once with XhoI and PvuI, and once with PvuI and KpnI and then a 1.5 kb and a 3.6 kb fragment were purified, respectively. A subsequent three-point ligation with the vector fragments and the ST-endoT fragment resulted in the pcDNA3.1/zeo-ST-endoT plasmid.

TABLE 3

Primer sequences for ST-endoT cloning

| Oligo | Sequence |
|---|---|
| PR1 | 5'-AACAAGGACGTACCCGTTAAAGAACTGCA-3' (SEQ ID NO: 2) |
| PR2 | 5'-CGCGAGCACCGTACCCGTTAAAGAACTGCA-3' (SEQ ID NO: 3) |

TABLE 3-continued

Primer sequences for ST-endoT cloning

| Oligo | Sequence |
|---|---|
| PR3 | 5'-CTCGAGATGGTACCCGTTAAAGAACTCXAGTTGAGAGC-3' (SEQ ID NO: 4) |
| PR4 | 5'-GCACCTGAGGTTACAGATCTTCTTCAGAAATAAGCTTTTGTTCAGCGTTA ACCATAGCGTAGTAGTTGATGG-3' (SEQ ID NO: 5) |
| PR5 | 5'-GCACTCGAGATGATTCACACCAACCTGAAGA-3' (SEQ ID NO: 6) |
| PR6 | 5'-TTAACGGGTACGTCCTTGTTCCACACCTG-3' (SEQ ID NO: 7) |
| PR7 | 5'-GCACTCGAGATGTGGCTGGGCCGCCGGG-3' (SEQ ID NO: 8) |
| PR8 | 5'-TTAACGGGTACGGTGCTCGCGTACAGGAGCC-3' (SEQ ID NO: 9) |
| PR9 | 5'-TCGAGATGAAGACTATCATTGCTTTGAGCTACATTTTCTGTCTGGTTTGG GCCCAAGACGTAC-3' (SEQ ID NO: 10) |
| PR10 | 5'-GTCTTGGGCCCAAACCAGACAGAAAATGTAGCTCAAAGCAATGATAGTC TTCATC-3' (SEQ ID NO: 11) |
| PR11 | 5'-GTGCTGCTCCTGGTTCTTTC-3' (SEQ ID NO: 12) |
| PR12 | 5'-TCAGCCATAGAACCGAAACC-3' (SEQ ID NO: 13) |
| PR13 | 5'-CTAGAATTCGCGATATCCCGGGCCCAGCGCTGCGGCCGCTCGAGCTAGC GTTTAAACT-3' (SEQ ID NO: 14) |
| PR14 | 5'-GATCAGTTTAAACGCTAGCTCGAGCGGCCGCAGCGCTGGGCCCGGGATA TCGCGAATT-3' (SEQ ID NO: 15) |
| PR15 | 5'-GCAGTCGACCATGTCCCCACTGAACCAGTCAGC-3' (SEQ ID NO: 16) |
| PR16 | 5'-GCAGCGGCCGCGGAGGCCTTCCGGAAAGGGAC-3' (SEQ ID NO: 17) |
| PR17 | 5'-AAACTTAGGCGGGAGCCACCTGGCTGGTCTCAGTACTGGCCTTCCGGAA AGGGAC-3' (SEQ ID NO: 18) |
| PR18 | 5'-CTCCCGCCTAAGTTTAAACGTTTAACCCGGGTAAATTCCGC-3' (SEQ ID NO: 19) |
| PR19 | 5'-GATTATGATCAGTTTAAACACTAGTAAATTCTAGAGTCGCGGC-3' (SEQ ID NO: 20) |
| PR20 | 5'-CTCAAGGGCCCCTTGACC-3' (SEQ ID NO: 21) |
| PR21 | 5'-CGAGCAGAATTCAATGGTGATGATGGTGATGCTCCTGGACTGGCTCCCA G-3' (SEQ ID NO: 22) |

Stable Cell-Line Generation

293SGnTI(−) cells were transfected in a small-scale transfection with pcDNA3.1(−)Zeo-ST-endoT. Selection was initiated with 15 µg/mL ConA 48 hours after transfection. After 14 days, the cells were trypsinized and replated in conditioned medium (medium of 2-day-old 293SGnTI(−) cultures, sterile filtered and mixed with 50% (v/v) fresh DMEM/F12) containing 10 µg/mL ConA. After 14 days, five large and nicely separated colonies were picked and expanded in the presence of 10 µg/mL ConA. The two fastest growing clones were further analyzed.

293SGnTI(−) and 293SGlycoDelete Growth Curve

Cells from a 70-80% confluent culture were first diluted to ~60,000 cells per milliliter, counted again (time point 0 hour) and transferred to a six-well plate (180,000 cells per well). At each time point, three wells were detached by pipetting up and down the medium, and the viable cells were counted for each well using trypan blue exclusion and a hemocytometer. The result shown in FIG. 1C represents one of two replicate experiments.

Gene-Expression Analysis.

RNA isolation and sample preparation for analysis on GeneChip Human Exon 1.0 ST Arrays (Affymetrix) were as follows.

Total RNA was extracted from three replicates cultures of both lines with the RNEASY® Midi kit (Qiagen), according to the manufacturer's instructions. RNA quality was assessed on a 2100 BIOANALYZER® using RNA 6000 Pico chips (Agilent Technologies, Santa Clara, Calif., USA). All samples had an RNA Integrity Number (RIN) of 9.5 or better. After spiking the total RNA samples (RNA sample preparation, see Online Methods) with bacterial poly-A RNA positive controls (Affymetrix, Santa Clara, Calif., USA), every sample was reverse transcribed, converted to double-stranded cDNA, in vitro transcribed and amplified using the AMBION® WT Expression Kit. The obtained single-stranded cDNA was biotinylated after fragmentation with the WT Terminal Labeling kit (Affymetrix), according to the manufacturer's instructions. The resulting samples were mixed with hybridization controls (Affymetrix) and hybridized on GENECHIP® Human Exon 1.0 ST Arrays (Affymetrix). The arrays were stained and washed in a GENECHIP® Fluidics Station 450 (Affymetrix), and scanned for raw probe signal intensities with the GENECHIP® Scanner 3000 (Affymetrix). Exon array data are MIAME compliant and available from the ArrayExpress database (on the World Wide Web at ebi.ac.uk/arrayexpress) under accession number E-MEXP-3516.

A combination of the R Statistical Software Package (on the World Wide Web at r-project.org) and Affymetrix Power Tools (APT; Affymetrix) were used for the quality control and differential expression analysis of the exon array data, partly as described earlier.[7] Briefly, exon- and gene-level intensity estimates were generated by background correction, normalization and probe summarization using the Robust Multi-array Average (RMA) algorithm with APT. Quality control of the data before and after normalization was performed in R through the generation of various plots such as box and density plots. Genes of which the expression was undetected in both lines were excluded from further analysis. A gene was considered to be detected when more than half of its exons were detected above the background (p<0.05) in at least two of the three biological replicates of that cell line. Genes of which the expression was below the estimated noise level in both lines were also removed from further analysis. The noise level threshold was set at the signal intensity level (the APT output intensity, averaged over the three replicates), which eliminated "detection" of expression of more than 95% of the genes on the Y-chromosome, which is absent from the 293 lineage (which was derived from a female embryo) and thus serves as an appropriate internal negative control.

Differential gene expression analysis was performed using a linear model fit implemented in the R Bioconductor package Limma,[8] considering only core probesets. The Benjamini-Hochberg (BH) method was applied to correct for multiple testing.

GM-CSF Production and Purification.

The plasmid for transient GM-CSF expression (pORF-hGM-CSF-6× His) was transiently transfected to both 293SGnTI(-) and 293SGlycoDelete cell lines. The secreted GM-CSF was purified from the medium.

Construction of the pORF-hGM-CSF-6× His plasmid. A partial CDS of the human GM-CSF C-terminally tagged with six His residues was amplified with primers PR18 and PR19 from the pORF-hGM-CSF plasmid (Invivogen, CA, USA). The PCR fragment and the pORF-hGM-CSF plasmid were digested with ApaI and EcoRI and ligated both fragments to result in the pORF-hGM-CSF-6× His plasmid.

Human GM-CSF purification. 293SGnTI-/- and 293SGlycoDelete cells were transiently transfected with the pORF-hGM-CSF-6× His plasmid (transient transfection, see online methods). Four days post-transfection, 50 ml of medium containing the expressed protein was harvested and dialyzed against buffer A (20 mM $NaH_2PO_4$, 0.5 M NaCl and 20 mM imidazole pH 7.5) using 3 kDa MWCO membranes. The dialysate was loaded onto a 1 ml His-Trap HP column charged with $Ni^{2+}$ ions (GE Healthcare UK Ltd, Buckinghamshire, UK). Then, the column was washed with buffer A until the A280 had dropped back to the baseline. After washing the column with ten-column volumes 6% buffer B (20 mM $NaH_2PO_4$ pH 7.50+20 mM NaCl+0.5 M imidazole), bound proteins were eluted with 100% buffer B and collected in 1 ml fractions. The presence of GM-CSF in the collected fractions was verified by tricine SDS-PAGE gel electrophoresis.[9] The protein concentration was measured based on the $A_{280}$ absorbance of the GM-CSF-containing fractions versus buffer B as a blank. Concentrations were calculated using the theoretical absorption coefficient with all cysteine residues in disulfide linkages (13980 $M^{-1}$ $cm^{-1}$), as calculated by the protparam tool (on the World Wide Web at web.expasy.org/protparam).[10]

Anti-CD20 Production and Purification.

Anti-CD20 was transiently expressed in both 293S and 293SGlycoDelete cell lines as described above and purified as follows: 4 days post-transient transfection of 293S and 293SGlycoDelete cells with the vector containing anti-CD20 (transient transfection, see online methods), the medium containing the expressed protein was harvested and loaded onto an affinity column 5 ml HITRAP® Mab Select SuRe (GE Healthcare UK Ltd, Buckinghamshire, UK). The column was then washed with PBS until $A_{280}$ had dropped back to baseline. Bound proteins were eluted with 50 mM glycine pH 3.5 and collected in 1 ml fractions. The presence of anti-CD20 in the collected fractions was verified by tricine SDS-PAGE gel electrophoresis. A buffer exchange was performed on the pooled fractions that contained anti-CD20 to a 25 mM histidine 125 mM NaCl buffer at pH 6.0. Antibody concentration in the purified samples was measured with a Synergy MX spectrophotometer (Biotek, VT, USA). The protein concentration was measured based on the $A_{280}$ absorbance of the purified antibody. Concentrations were calculated using the theoretical extinction coefficient.

5HT1D receptor expression and sample preparation. Detailed methods for stable 5HT1DR-expressing cell line generation, 5HT1D sample preparation and analysis are as follows.

Construction of the pT-REx-5HT1DRho and pT-REx-5HT1DRho-IRESdsRed2 plasmid. The pT-REx-DEST30 plasmid (Invitrogen) was amplified in a dam/dcm methylation-deficient *E. coli* strain and digested with BclI and XbaI. A dsDNA insert was created by annealing oligos PR11 and PR12. Subsequent ligation of the dsDNA insert into the XbaI/BclI-digested pT-REx-DEST30 fragment generated the pT-REx-MCS plasmid.

The CDS for the 5-hydroxy tryptamine 1D receptor (NM_00864) from a human fetal brain cDNA library was amplified using primers PR13 and PR14 and cloned into a pCR®II-TOPO® plasmid (Invitrogen), generating the Topo-5HT1D plasmid. A Rho1D4-tagged 5HT1DR fragment was amplified from the Topo-5HT1D plasmid with primers PR13 and PR15. The PCR fragment was digested with SalI and the pT-REx-MCS plasmid with PmeI and SalI, followed by dephosphorylation. These fragments were ligated to result in the pT-REx-5HT1DRho plasmid.

The IRESdsRed2 fragment from the pLV-tTR/KRAB-Red plasmid (a kind gift of Prof. Peter Vandenabeele, VIB-UGhent) was amplified with primers PR16 and PR17. The pT-REx-5HT1DRho plasmid was digested with PmeI and used with the IRESdsRed2 fragment in a cloneEZ (GenScript USA Inc., NJ, USA) reaction. This resulted in the pT-REx-5HT1DRho-IRESdsRed2 plasmid.

5HT1DR expressing 293SGnTI-/- and 293SGlycoDelete clones. Cell lines were generated, stably and inducibly expressing the 5HT1D receptor by transfecting 293SGnTI-/- with the pT-RExL-5HT1DRho-IRESdsRed2 plasmid and 293SGlycoDelete cells with pTRExL-5HT1DRho or pT-RExL-5HT1DRho-IRESdsRed2. Selection was performed with G418 (Sigma-Aldrich) at 600 µg/ml (293SGnTI-/- cells) and at 150 µg/ml G418 (293SGlycoDelete cells). The G418-resistant cells were then subjected to limiting dilution cloning in conditioned medium. Expression of the 5HT1D receptor was induced with 2 µg/ml tetracycline and 1 mM valproate (Sigma- Aldrich). The 293SGnTI−/− 5HT1DR clone expressing the highest intensity of red fluorescence was selected after 2-3 days of induction by fluorescence microscopy.

ELISA analysis for 5HT1DR expression in 293SGlycoDelete clones. For ELISA analysis of the 5HT1DR-expressing 293SGlycoDelete clones, cells were collected from 24-well plates after 2-3 days induction with 2 μg/ml tetracycline and 1 mM valproate (Sigma-Aldrich). The cells were spun down and the supernatant discarded. Cells were lysed with RIPA buffer+protease inhibitors by incubating for 20 minutes on ice. The debris was removed by spinning down the samples at 12,000 rpm for 10 minutes. Protein was determined in a bicinchoninic acid (BCA) assay (Pierce Biotechnology Inc., Rockford, Ill., USA) according to the manufacturer's instructions. 15 μg of each sample, of a positive control sample of 5HT1DR produced in *P. pastoris* and of a 293SGlycoDelete-negative control sample were coated overnight at 4° C. on a maxisorb plate. The plate was washed three times with water and one time with wash buffer (PBS+0.1% TWEEN®-80). Blocking buffer (PBS+1% milk powder) was added to each well and incubated for 2 hours at room temperature. After washing, the anti-rho1D4 antibody (University of British Columbia, Vancouver, Canada), diluted 1/100 in sample buffer (PBS+0.05% TWEEN®+0.5% milk powder) was added and the samples were incubated for 1 hour at room temperature. The plate was again washed and then an anti-mouse IgG coupled to HRP secondary antibody (GE Healthcare Biosciences, Pittsburgh, Pa., USA) and diluted 1/5000 in sample buffer was added to the samples. Finally, the plate was again washed and samples were analyzed with the BD OptEIA™ TMB substrate reagent set (BD, Franklin Lakes, N.J., USA), according to the manufacturer's instructions.

5HT1D receptor expression and sample preparation. 293SGnTI−/− and 293SGlycoDelete cell lines were generated, stably and inducibly expressing the 5HT1D receptor. Detailed methods for the generation of 5HT1DR expression constructs and subsequent generation of stable 5HT1DR-expressing clones are described in Supplementary Note 1. The selected 5HT1DR-expressing clone of each line was induced with 2 μg/ml tetracycline and 1 mM valproate. Three days post-induction, cells were collected. Cell pellets were resuspended in 5 ml of 20 mM Tris-HCl pH 8.0+1 mM EDTA+Complete EDTA-free protease inhibitors (Roche, Mannheim, Germany). 1.25 ml of each sample was sonicated on ice (15 cycles, each cycle: 1 second on and 5 seconds off, at 20% amplitude) with a VCX500 sonicator (Sonics & Materials Inc., Newtown, Conn., USA). The lysates were immediately centrifuged for 10 minutes at 13,000 rpm and 4° C. and solubilized the pellets in the buffer described above+0.35 mM NaCl and 0.5% n-dodecyl-β-D-maltoside. Debris was removed by immediately centrifuging samples again for 10 minutes at 13,000 rpm at 4° C.

To assess the presence of PNGaseF-sensitive N-glycans on the 5HT1D receptor, 50 μl aliquots of the samples, supplemented with 1% Igepal CA-630 and 200 U of PNGaseF (in-house production), or no enzyme, were incubated overnight at 37° C. The samples were analyzed by immunoblotting using a mouse anti-rho1D4 primary antibody (University of British Columbia, Vancouver, Canada), diluted 1/250.

Sialidase, Galactosidase and PNGaseF Digests and SDS-PAGE.

The glycoproteins were diluted in 50 mM of phosphate buffer (pH 7.0) containing 40 mM of β-mercaptoethanol and 0.5% SDS. Samples were incubated for 10 minutes at 98° C. After cooling, 1% Igepal CA630 and the appropriate enzymes were added: 100 U of PNGaseF (produced in-house), 200 mU of *Arthrobacter ureafaciens* sialidase (produced in-house), 2 mU of *Streptococcus pneumoniae* β-1,4-galactosidase (Prozyme) or combinations. The samples were incubated overnight at 37° C. and analyzed the following day on a tricine SD S-PAGE gel.

Thermofluor assays. Thermofluor assays were performed as described in Ericsson et al.[17] Briefly, purified protein was diluted to an appropriate assay volume (10-20 μl) in a solution containing buffer (PBS for GM-CSF and His buffer—25 mM histidine, 125 mM NaCl, pH 6.00—for anti-CD20) and 20× concentrated Sypro orange dye (5000× solution in DMSO, Life Technologies, Paisley, UK). Each experiment was run as a technical triplicate, and triplicate blank measurements with no test protein were included. Fluorescence in function of temperature was recorded in a 348-well LIGHTCYCLER® 480 (Roche, Basel, Switzerland) from 25° C. to 95° C. with a temperature ramping rate of 0.01° C./second.

Before any calculations and statistical analyses, datasets with obvious technical problems (abnormally high initial fluorescence, off-scale fluorescence) were omitted entirely. Melting temperatures were calculated as the $V_{50}$ value of a Boltzmann sigmoidal curve fitted to the averaged data points of the three replicates in each experiment. For the curve fitting procedure, data points beyond the maximal fluorescence were omitted. When more than one melting point was calculated from a single experiment, an appropriate subset of data points, including the minimal and maximal fluorescence values at temperatures just below and above that melting point, was used. For graphing, the raw datasets were averaged, blank (averaged) corrected and then normalized (minimal value=0%, maximal value=100%).

For the GM-CSF samples, an average $T_m$ was calculated from a set of independent experiments (*E. coli*: n=4, 293S: n=3, 293SGlycoDelete: n=3). Tests were run to determine whether the average $T_m$s were statistically significantly different by Kruskal-Wallis one-way ANOVA (P=0.05) and Dunn test for multiple comparisons (α=0.05).

MALDI Glycopeptide Analysis.

GM-CSF of the different cell lines (1-4 μg of protein in 20 μL) was supplemented with 10 μL of 3× tricine gel loading buffer (1.5 M Tris-HCl, pH 8.45, 35% glycerol, 10% SDS, 0.01% Coomassie and 30 mM DTT) and incubated for 10 minutes at 98° C. 3 μL of a 500 mM iodoacetamide stock was added, and the samples were incubated for 1 hour in the dark. The samples were separated on a 12% tricine SDS-PAGE gel and cut out the bands.

Detailed methods for in-gel tryptic digestion are as follows. Gel pieces were washed three times with 50% acetonitrile (ACN), dried with 100% ACN and allowed to reswell in 100 mM NH$_4$HCO$_3$. Gel pieces were further dried in a SPEEDVAC®. 750 ng of trypsin (Promega, Madison, Wis., USA) was added and the gel pieces were allowed to reswell for 5 minutes. 100 mM NH$_4$HCO$_3$ was added to cover all gel pieces and the vials were incubated overnight at 37° C. 50 μl 100 mM NH$_4$HCO$_3$ was added to each vial and the samples were incubated on a shaker for 15 minutes. 50 μl 100% ACN was added and vials were incubated on a shaker for 15 minutes. Supernatants were collected in fresh vials. 50 μl 5% formic acid in 50% ACN was added and vials were incubated for 15 minutes on a shaker. The supernatants were collected. The 5% formic acid step was repeated once. Supernatants were pooled per sample and dried in a SPEEDVAC®, then reconstituted with 20 μl 50 mM phosphate buffer, pH 7.0 and 1 mM Pefabloc (Sigma-Aldrich).

The tryptic peptides were treated with either no enzyme, 50 mU of α-2,3-sialidase (Takara Bio Inc.), or 200 mU *A. ureafaciens* sialidase and 2 mU of *Streptococcus pneumoniae* β-1,4-galactosidase (Prozyme). All digests were incubated for 24 hours at 37° C., dried in a SPEEDVAC®, reconstituted with 10 µL of 0.2% trifluoroacetic acid (TFA) (Sigma-Aldrich) and cleaned up with C18 ZIPTIP® pipette tips (Millipore) according to the manufacturer's instructions. Samples were analyzed with 6-aza-2-thiothymine (ATT) matrix saturated in 50% acetonitrile containing 0.1% TFA, on a 4800 MALDI TOF/TOF Analyzer (Applied Biosystems) in the positive ion mode. The reported m/z values were observed in several iterations of technical optimizations and the results of the fully optimized experiments are shown.

LC-MS/MS Glycopeptide Analysis.

9 µg anti-CD20 were diluted in 20 µL of 50 mM phosphate buffer, pH 7.0. Either no enzyme, 100 mU of *Arthrobacter ureafaciens* sialidase (produced in-house) or 2 mU of β-1,4-galactosidase (*Streptococcus pneumoniae*) and 100 mU of sialidase were added, and the mixture was incubated for 4 hours at 37° C. The samples were denatured in a 2 M urea, 10 mM DTT, 50 mM ammonium bicarbonate buffer for 30 minutes at 60° C. Iodoacetamide was added to a concentration of 20 mM and the samples were incubated in the dark for 30 minutes. Next, the samples were digested with 1/50 (w/w) trypsin (Promega) and incubated overnight at 37° C.

The samples were loaded directly on an Acclaim PEPMAP™ 100 analytical column (L×ID 15 cm×75 µm, C18, 3 µm, 100 Å) (Thermo) at a flow rate of 300 nL per minute, on a U3000-RSLC system (Thermo). Mobile phases were 0.1% HCOOH in H2O (solvent A) and 0.1% HCOOH in acetonitrile (ACN) (solvent B). The samples were separated with a 30-minute gradient, ranging from 2% to 40% solvent B, and the eluting peptides were sprayed directly into a 4000 Q TRAP® mass spectrometer (AB Sciex) with the NANOSPRAY® II ESI source (AB Sciex). A selected-reaction-monitoring (SRM) method was used to target the glycosylated peptide EEQYNSTYR, where the triple quadrupole cycled through the following SRM transition list with a dwell time of 250 ms: Pep-GlcNAc: 696.8 (2+)/526.3 (+) and 696.8 (2+)/1189.5 (+) (DP 81.9 V, CE 39.8 eV), Pep-GlcNAc-Gal: 777.8 (2+)/526.3 (+) and 777.8 (2+)/1,189.5 (+) (DP 87.8 V, CE 43.9 eV), Pep-GlcNAc-Gal-Sial: 923.4 (2+)/526.3 (+) and 923.4 (2+)/1,189.5 (+) (DP 98.4 V, CE 51.2 eV). The 526.3-Da fragment ion (y4-ion, STYR) was used as quantifier, and the 1,189.5-Da fragment ion (loss of sugar-modification group) was used as qualifier. The analysis and processing of the data was done with Skyline.[25] This experiment was performed two times. One of the experiments was conducted as a technical duplicate, the other one as a technical triplicate.

Ratio of Sialylated and Galactosylated Glycans.

To calculate the percentage of GlycoDelete glycans that are sialylated, the area under the peak was extracted from the MALDI MS spectra for the Gal-GlcNAc-N (m/z=3622.3) and GlcNAc-N (m/z=3460.2) glycopeptides of both the undigested ($A_{GalGlcNAcUndig}$ and $A_{GlcNAcUndig}$) and α-2,3-sialidase digested ($A_{GalGlcNAcDig}$ and $A_{GlcNAcDig}$) GlycoDelete GM-CSF samples. The percentage of sialylated glycans was calculated as shown in the formula below. Gal-GlcNAc-N peak areas were first normalized to GlcNAc-N peak areas in both spectra. The resulting value for the Gal-GlcNAc-N peak from the undigested sample was subtracted from the value for the Gal-GlcNAc-N peak from the sialidase-digested sample. Then, this difference was divided by the summed normalized peak areas of the GlcNAc and GalGlcNAc peaks in the digested sample (total normalized peak area of N27 or N37 encompassing glycopeptides).

$$\% \text{ sialylated glycans} = \frac{\left[\frac{A_{GalGlcNAcDig}}{A_{GlcNAcDig}}\right] - \left[\frac{A_{GalGlcNAcUnDig}}{A_{GlcNAcUnDig}}\right]}{\left[\frac{A_{GlcNAcDig}}{A_{GlcNAcDig}}\right] + \left[\frac{A_{GalGlcNAcDig}}{A_{GlcNAcDig}}\right]} * 100\%$$

To calculate the percentage of GlycoDelete glycans that are galactosylated (disaccharide), the same datasets were utilized. The percentage of galactosylated glycans was calculated as shown in the formula below. Peak areas for Gal-GlcNAc-N were again first normalized in both the sialidase-digested and undigested samples. The normalized peak area for the undigested Gal-GlcNAc-N peak was then divided by the summed normalized peak areas of the GlcNAc-N and Gal-GlcNAc-N peaks in the digested sample (the total normalized peak area of N27 or N37 encompassing glycopeptides).

$$\% \text{ galactosylated glycans} = \frac{\left[\frac{A_{GalGlcNAcUnDig}}{A_{GlcNAcUnDig}}\right]}{\left[\frac{A_{GlcNAcDig}}{A_{GlcNAcDig}}\right] + \left[\frac{A_{GalGlcNAcDig}}{A_{GlcNAcDig}}\right]} * 100\%$$

GM-CSF Bioactivity Experiments and TF1 Proliferation Assay.

TF1 cells (ATCC No. CRL-2003) were maintained in RPMI 1640, 10% (v/v) FBS, 2 mM of L-Gln and 2 ng/mL of recombinant human GM-CSF at 27° C., 5% CO2. Before starting the assay, cells were washed three times with medium without cytokines. The cells were subsequently put back in medium (200,000 cells per milliliter) without cytokines and left for 2 hours at 37° C.

Upon initiation of the assay, cells were plated in a 96-well plate (20,000 cells per well in 100 µL medium) and serial dilutions (54 ng/mL to 8 pg/mL) of the different glycoforms of GM-CSF were added. Cells were incubated for 48 hours, 72 hours and 96 hours before performing the MTT assay (3-(4,5-dimethylthiazol-2-yl)-2,5-diphenyltetrazolium bromide) as described.[28] Briefly, 20 µl of MTT (5 mg/mL stock) was added per well and incubated. After 4 hours at 37° C., 80 µL of stop solution (10% SDS in 0.01 M HCl) was added, and the plate was further incubated overnight at 37° C. Finally, optical density was measured at 595 nm. The data points plotted in FIG. 2 represent mean values from three technical replicates. The error bars are s.d. The reported differences between the GM-CSF glycoforms were observed in several iterations of technical optimization of these experiments. The results of the fully optimized bioactivity experiment are shown.

Rabbit Immunizations.

New Zealand White male or female rabbits, aged 13-16 weeks (two rabbits for each antigen, results from only one rabbit shown in FIGS. 7A-7F and 14A-14G) were injected with 293S GM-CSF, GlycoDelete GM-CSF, 293S anti-CD20 or GlycoDelete anti-CD20. 50 µg of antigen in 500 µL of antigen solution (50 µg of protein diluted in 0.9% NaCl solution up to 500 µL)+500 µL of complete Freund's adjuvant was injected subcutaneously at days 0, 14, 28 and 56. Rabbits were bled on day 0 (pre-immune bleeding), day 38, day 66 and day 80 (final bleeding). The immunization was performed by CER Groupe and approved by the CER Groupe ethical committee.

Serum ELISAs with GlycoDelete Proteins.

Glycosidase digestions were performed as described above. Wells of Maxisorp microtiter plates were coated (overnight, 4° C.) with 0.25 µg/mL of GM-CSF or 0.15 µg/mL of anti-CD20 in 50 µl of coating buffer (0.05 M Na2CO3, 0.05 M NaHCO3, pH 9.6) washed three times with PBS+0.1% TWEEN®, and blocked with 1% BSA in PBS with 250 mM glycine for 2 hours at room temperature. Blocking buffer was removed and the plates were dried overnight.

Detection antibodies (anti-GM-CSF rabbit serum, final bleeding; anti-(anti-CD20) rabbit serum, final bleeding) were added in PBS+0.1% TWEEN®-20+0.1% goat serum and incubated for 2 hours at room temperature.

Plates were washed four times with wash buffer before adding donkey anti-rabbit HRP (1:2,000) (cat no. NA934, GE Healthcare) in PBS+1% BSA and incubating for 1 hour at room temperature.

The plates were washed again three times with wash buffer, upon which the TMB (3,3',5,5'-tetramethylbenzidine, BD OptEIA) substrate (100 µL per well) was added and the plate was incubated at room temperature for 30 minutes. Finally, 50 µL of stop solution (2 N H2SO4) was added and measured the absorbance at 450 nm.

The ELISA with GM-CSF was performed once with two biological replicates (two rabbits immunized; FIGS. 7E and 7F). The ELISA with anti-CD20 was performed once with two biological replicates (two rabbits immunized) and one of the biological replicates was then repeated with three technical replicates. The result of the latter experiment is shown in FIG. 14F. The data points plotted in this figure represent mean values from the three technical replicates. The error bars are s.d.

CD20 Binding by Anti-CD20.

Fc receptors on the Raji cells were blocked with anti-CD32 antibodies IV.3 (ref. 29) (produced in-house) and AT10 (cat no. MCA1075, AbD Serotec) at 10 µg/mL and incubated with the cells for 1 hour on ice. Next, the cells were plated into a 96-well plate (105 cells per well), and the 293S or 293SGlycoDelete anti-CD20 was added in a dilution series starting from 10 µg/mL. The cells were incubated for 1 hour at 4° C. and then washed twice with PBS+2% BSA. To detect the anti-CD20, an anti-F(Ab)2 secondary antibody conjugated to DYLIGHT® 649 (cat no. 109-496-097, Jackson laboratories) was added at a 1:200 dilution. The cells were again incubated for 30 minutes at 4° C. and washed twice with PBS+2% BSA. To fix the cells, 150 µL of fixative (CellFIX, Becton Dickinson) was added in each well and incubated for 1 hour at 4° C. The secondary antibody was detected through flow cytometry (FACS® Calibur, Becton Dickinson). The data points plotted in FIGS. 3A and 3B represent mean values from three technical replicates. The error bars are s.d. This experiment was conducted twice.

FcγR Surface Plasmon Resonance Experiments.

A BIACORE® 2000 SPR biosensor (GE Healthcare) was used to assay the interaction of FcRn with the different anti-CD20 glycoforms. All experiments were performed at 25° C. A CM5 chip was activated for cross-linking for 7 minutes with a solution of EDC (1-ethyl-3-[3-dimethylaminopropyl]carbodiimide) and NHS (N-hydroxysuccinimide) at a flow rate of 10 µL/minute. Next, 10 µg/mL of STREPTAVIDIN® (Roche) in a 10 mM acetate buffer, pH 5.0, was immobilized at the same flow rate for 7 minutes, resulting in densities ranging from 1,180 to 1,280 resonance units (RU). After immobilization, the chip was blocked by injecting 1 M of ethanolamine for 7 minutes. To finalize the immobilization, the chip was washed three times with 20 µL of a 40 mM NaOH, 1 M NaCl buffer.

To immobilize the hFcRn on the STREPTAVIDIN® sensor surface, the pH was brought to 8.0 by priming with HBS-EP buffer, pH 8.0 (GE Healthcare). Biotinylated hFcRn (produced at NovImmune)30 was diluted in HBS-EP buffer and immobilized on the chip. Then, the system was primed with HBS-EP buffer at pH 6.0.

IgG was injected at different concentrations ranging from 67 nM to 2 nM, and diluted in HBS-EP buffer, pH 6.0. Each injection was performed for 3 minutes at a flow rate of 30 µL/minute and every time in duplicate. The dissociation was monitored for 12 minutes. HBS-EP buffer, pH 8.0, was used for regeneration. Results were double referenced and analyzed using a Langmuir 1:1 fitting model (BIAeval software version 4.1).

Competition ELISAs.

The wells of Maxisorp microtiter plates were coated overnight at 4° C. with coating antibody (8 µg/mL of an anti-idiotype antibody for the FcγRI ELISA; 16 µg/mL and 10 µg/mL of HZ 15C1, a humanized anti-TLR4 IgG1 (NovImmune), for FcγRIIa and FcγRIIb, respectively), in 50 µl of PBS and were then washed five times with washing buffer (PBS+0.05% TWEEN®) and blocked with 250 µL of 3% BSA in PBS per well for 1 hour at 37° C. After blocking, the plates were washed five times with washing buffer.

50 µL of anti-CD20 was added to the wells in a serial dilution in dilution buffer (PBS+1% BSA) together with 50 µL of the His-tagged FcγR (FcγRI, 0.030 µg/mL; FcγRIIaR, 0.056 µg/mL; FcγRIIb, 1 µg/mL (R&D Systems)). The plates were incubated for 1.5 hours at 37° C. and washed five times with washing buffer. HRP-labeled anti-His antibody (cat no. 34660, Qiagen) was added at a 1:2,000 dilution in dilution buffer and the plates were incubated for 1 hour at 37° C. The plates were washed five times with washing buffer before addition of 50 µL of TMB super-slow (Diarect) substrate. The plates were then incubated in the dark for 30 minutes. Finally, 50 µL of stop solution (2 N H2SO4) was added. Absorbance at 450 nm was measured with a SYNERGY® HT plate reader (Biotek).

The data points plotted in FIG. 14E (top three panels), represent mean values from three technical replicates. The error bars are s.e.m. The reported differences between the 293S- and 293SGlycoDelete-produced antibodies were observed in several iterations of technical optimization of these experiments, and the results of the fully optimized ELISAs are shown.

Biolayer Interferometry Assay.

Real-time binding of purified IgG to FcγRIIIa was evaluated using biolayer interferometry (BLI) on an OCTET® RED96 system (Fortebio, Menlo Park, Calif.). Assays were performed at a temperature of 30° C. in kinetics buffer containing 1 mM phosphate, 15 mM NaCl, 0.002% (vol/vol) TWEEN®-20, 0.005% (wt/vol) sodium azide, 0.1 mg/mL (wt/vol) BSA, pH 7.4. FcγRIIIaV (R&D Systems, MN, USA) tagged with a hexahistidine tag was brought to a concentration of 1.5 µg/mL in kinetics buffer. The receptor was captured on an anti-penta-His biosensor (Fortebio, Menlo Park, Calif.) for 10 minutes. The ligand density was 0.5 nm. Baseline signal had stabilized after 2 minutes incubation in kinetics buffer.

A first binding assay was performed with IgG at a single concentration of 50 µg/ml in kinetics buffer. Association and dissociation were monitored for 5 minutes. Regeneration was performed by incubating the sensor with 10 mM glycine pH 3.0 buffer for 20 seconds, followed by 20 seconds incubation in kinetics buffer. These incubations were repeated twice to achieve complete regeneration.

For the kinetics experiment, an $F_c\gamma RIIIaV$-coated biosensor was incubated with IgG at concentrations ranging from 333 nM to 19.3 nM. A two minute baseline situation was followed by a five-minute association phase and a 15-minute dissociation phase in kinetics buffer. Regeneration was performed as described above. The affinity was determined at equilibrium using a steady-state model. All analyses were done using the ForteBio Data Analysis software (Fortebio, Menlo Park, Calif.).

ADCC Assay.

Peripheral blood mononuclear cells (PBMCs) were isolated from fresh blood after centrifugation in a Ficoll tube (Vacutainer tube CPT, Becton Dickinson). Natural killer (NK) cells were isolated from the PBMC pool using a negative NK Cell Isolation Kit (Miltenyi Biotec). These cells were activated overnight in growth medium (RPMI 1640+10% FBS+2 mM glutamine)+10 ng/mL IL-2.

Raji cells were seeded in a 96-well plate at 20,000 cells per well. 25 µL samples of anti-CD20 antibodies were added in a 1:5 dilution series (in ADCC medium: RPMI 1640+1% BSA+2 mM glutamine+25 µg/mL gentamicin), starting with 5 µg/mL. The plates were then incubated for 30 minutes at 37° C. and 5% CO2. NK cells were added to the Raji cells in a ratio of 1:5 (Raji/NK), and the plate was incubated at 37° C. and 5% CO2 for 4 hours. Finally, the specific lysis was determined by measuring the lactate dehydrogenase (LDH) levels for each well (Cytotoxicity Detection Kit PLUS, Roche).

The data points in FIG. 14E (bottom) represent mean values from three technical replicates. The error bars are s.d. The reported profiles were observed in several iterations of technical optimization of these experiments and the results of the fully optimized experiment are shown.

Pharmacokinetics.

Two groups of 36 female, 8-week-old C57BL/6J mice (Charles River) were randomly assigned to be intravenously injected with 18.5 µg (1 mg per kilogram of body weight) of either 293S or 293SGlycoDelete anti-CD20. At each time point (1 hour, 24 hours, 48 hours, 4 days, 7 days, 10 days, 14 days, 21 days and 28 days), four mice per treatment group were sacrificed for a final bleeding, and the concentration of anti-CD20 was determined with the FastELYSA human IgG kit (RD-Biotech) according to the manufacturer's instructions. The data points shown in FIG. 14G are the mean values (four mice) for each time point. The error bars are s.e.m. This experiment was repeated with bleedings at earlier time points after injection (see FIG. 17). For practical reasons, the investigators were not blinded to the treatment group assignment of the mice. This experiment was approved by the ethical committees of Ghent University (Belgium) and of the Cantonal Veterinary Office of Geneva (Switzerland).

Construction of pCAGGS-s-endoT, pCAGGS-GM$_2$S-endoT and pCAGGS-ST-endoT. The endoT coding sequence[3] without the signal sequence was amplified from a pUC19 cloning vector containing the full-size endoT coding sequence, with PCR primers PR1 and PR4 (for ST-endoT), PR2 and PR4 (for GM$_2$S-endoT) or PR3 and PR4 (for "endoT"). All primer sequences are provided in Supplementary Note 2. The coding sequence for the N-terminal parts of ST6GalI[4] (for ST-endoT) and B4GALNTI[5] (for GM$_2$S-endoT) were amplified from a human hepatoma G2 cDNA library with primers PR5, PR6 and PR7, PR8, respectively. Fusion PCR reactions to generate the ST-endoT, the GM$_2$S-endoT and endoT without signal sequence were set up using PR5 and PR4, PR7 and PR4 and PR3 and PR4, respectively. Subsequent digestion of the fusion PCR products ST-endoT, GM$_2$S-endoT and endoT with XhoI and Bsu36I and ligation into an XhoI and Bsu36I digested and dephosphorylated pCAGGS plasmid, resulted in the pCAGGS-ST-endoT and pCAGGS-GM$_2$S-endoT plasmids. The dsDNA signal sequence for the s-endoT construct was produced by annealing oligonucleotides PR9 and PR10. The pCAGGS-endoT plasmid was digested with XhoI and KpnI. Subsequent ligation of the adapter into the plasmid resulted in the pCAGGS-s-endoT plasmid.

Transfection and sample preparation. Cells were transfected as described (see online methods). Three days post-transfection with pCAGGS-s-endoT, pCAGGS-GM$_2$S-endoT or pCAGGS-ST-endoT, cells and supernatants were harvested. For cell lysates, cells were collected by centrifugation at 1000 rpm and washed once with PBS. Cell lysates were prepared by incubating ~1 million cells with 500 µl RIPA buffer (150 mM sodium chloride, 1.0% Igepal CA-630, 0.5% sodium deoxycholate, 0.1% sodium dodecyl sulphate and 50 mM Tris, pH 8.0) at 4° C. on a rotating platform for 30 minutes, followed by centrifugation at 14,000 rpm for 10 minutes and discarding the insoluble material. 20 µl samples were supplemented with 5 µl 5× SDS-PAGE loading buffer (8.3% SDS, 41.7% glycerol, 0.1% bromophenol blue, 208 mM Tris-HCl, pH 6.8 and 65 mM dithiothreitol added fresh) and boiled for 10 minutes.

500 µl samples of cell culture supernatants were cleared by centrifugation for 10 minutes at 14,000 rpm in a microcentrifuge, acetone precipitated by adding 2 volumes of ice cold acetone and incubated on ice for 30 minutes. Precipitated samples were centrifuged for 10 minutes at 14,000 rpm in a microcentrifuge and the supernatants were discarded. Pellets were dissolved by adding 80 µl of ultrapure water and 20 µl 5× SDS-PAGE loading buffer, followed by boiling to redissolve and denature protein pellets.

Immunoblotting. 25 µl aliquots of cell lysates or supernatant samples were analyzed for the presence of endoT fusion proteins by immunoblotting. Indirect detection was performed using a custom generated rabbit polyclonal antibody against the endoT enzyme (CER groupe, Département Santé, Marloie, Belgium). The antigen was endoT produced in *Pichia pastoris* and purified previously in the lab. The final antigen preparation was 1 mg/ml antigen in phosphate-buffered saline. The secondary antibody was an IRDye 680 goat anti-rabbit IgG (LI-COR Biosciences, Lincoln, Nebr., USA). To assess C-terminal processing, the same blots were probed with a mouse primary antibody directed against the myc tag (Life Technologies, Paisley, UK) and an IRDye 800 goat anti-mouse IgG secondary antibody (LI-COR Biosciences, Lincoln, Nebr., USA).

To evaluate the in vivo de-N-glycosylation by the endoT fusion proteins, the fusion constructs were transiently transfected (transfection, see Online Methods) to 293SGnTI−/− cells that stably and inducibly expressed the Flt3 receptor extracellular domain (Flt3ECD), C-terminally tagged with a penta-His tag (cells kindly provided by Prof. Dr. S. Savvides, UGhent) or to 293SGnTI−/− cells stably and inducibly expressing 5-hydroxytryptamin receptor 1D (5HT1D), C-terminally tagged with a Rho1D4 tag (stable 5HT1D cell line isolation, see FIGS. 5A and 5B methods thereof). The producer cell lines were transfected with the endoT fusion constructs or empty plasmid and induced with 2 µg/ml tissue culture grade tetracycline and 5 mM sodium butyrate (both Sigma-Aldrich, St. Louis, Mo., USA). Supernatants (for Flt3ECD production) were harvested 48 hours and 72 hours post-transfection/induction, or cells (for 5HT1D production) were harvested 72 hours post-transfection/induction.

For the Flt3ECD, 20 µl aliquots of cell supernatants were run on SDS-PAGE and the processing of the Flt3 was analyzed by Western blotting. The primary antibody was a mouse anti-penta his tag (Qiagen, Hilden, Germany) and the secondary antibody, an anti-mouse IgG-coupled to HRP (GE Healthcare Biosciences, Pittsburgh, Pa., USA).

For the 5HT1D, cells were collected by centrifugation at 1000 rpm and washed once with PBS. Cell lysates were prepared by incubating ~1 million cells with 500 µl RIPA buffer at 4° C. on a rotating platform for 30 minutes, followed by centrifugation at 14,000 rpm for 10 minutes and discarding the insoluble material. 20 µl samples were supplemented with 5 µl 5× SDS-PAGE loading buffer and boiled for 10 minutes and then loaded on a 10% SDS-PAGE gel. Western blot analysis was performed with a primary mouse anti-Rho1D4 antibody (University of British Columbia) and a secondary anti-mouse IgG-coupled to HRP.

Early splits (#+8) of both endoT-expressing clones and 293SGnTI−/− cells were plated in 24-well plates at 30,000 cells per well in the presence of increasing ConA concentrations: 0-22 µg/ml. ConA was added immediately upon splitting. When cells in the wells containing no ConA had grown to confluence, end points were determined microscopically. End points were defined through phase contrast microscopy, as the concentration of ConA that reduced the growth to ≤10% confluence of the well. For assessing long term stability of endoT expression, late split cells (#+28) were compared to early split cells (#+8).

EndoT CDS validation. To validate the presence of the CDS, genomic DNA was prepared from ~1 million cells of both the 293SGlycoDelete and 293SGnTI−/− cell lines with the Gentra PUREGENE® Core kit A (Qiagen, Hilden, Germany), according to the manufacturer's instructions. A touchdown PCR reaction was performed with the PHUSION® High-Fidelity DNA polymerase (New England Biolabs, Ipswich, Mass., USA) employing ~10 ng genomic DNA for each 50 µl reaction and primers PR11 and PR12. PCR cycling was a touchdown protocol with the primer annealing temperature lowered by 1° C. every two cycles, from 67° C. to 64° C. and held at 64° C. for 30 cycles (accounting for 36 cycles in total). PCR products were analyzed with a Shimadzu MULTINA™ microchip DNA/RNA electrophoresis system, employing the DNA-500 reagent kit (Shimadzu Corporation, Kyoto, Japan) according to the manufacturer's instructions.

EndoT fusion protein validation. The expression of the ST-endoT protein was assessed by Western blotting. Methods are the same as described for FIGS. 1A-1D, except that the secondary antibody was an IRDye 800 Goat anti-rabbit IgG antibody (LI-COR Biosciences, Lincoln, Nebr., USA).

DSA-FACE analysis of 293S GM-CSF. N-linked oligosaccharides were prepared from purified proteins upon blotting to PVDF membrane in the wells of 96-well plate membrane plates, and were analyzed by capillary electrophoresis with laser-induced fluorescence detection (CE-LIF) using an ABI 3130 capillary DNA sequencer as described previously.[6]

TABLE 4

(Data underlying FIG. 1C)

| hours | Well 1 | Well 2 | Well 3 | Avg | St Dev | Cells/well | Cells/well St dev |
|---|---|---|---|---|---|---|---|
| 293SGlycoDelete | | | | | | | |
| 0 | 27 | 23 | 21 | 23.67 | 3.06 | 157778 | 20367 |
| 24 | 36 | 37 | 26 | 33.00 | 6.08 | 220000 | 40552 |
| 48 | 53 | 42 | 39 | 44.67 | 7.37 | 297778 | 49141 |
| 72 | 150 | 194 | 208 | 184.00 | 30.27 | 1226667 | 201770 |
| 96 | 270 | 282 | 234 | 262.00 | 24.98 | 1746667 | 166533 |
| 120 | 468 | 510 | 378 | 452.00 | 67.44 | 3013333 | 449592 |
| 144 | 492 | 519 | 465 | 492.00 | 27.00 | 3280000 | 180000 |
| 168 | 549 | 510 | 504 | 521.00 | 24.43 | 3473333 | 162891 |
| 192 | 512 | 476 | 532 | 506.67 | 28.38 | 3377778 | 189189 |
| 293SGnTI−/− | | | | | | | |
| 0 | 29 | 27 | 23 | 26.33 | 3.06 | 175556 | 20367 |
| 24 | 55 | 58 | 45 | 52.67 | 6.81 | 351111 | 45379 |
| 48 | 51 | 61 | 72 | 61.33 | 10.50 | 408889 | 70026 |
| 72 | 199 | 176 | 168 | 181.00 | 16.09 | 1206667 | 107290 |
| 96 | 266 | 268 | 210 | 248.00 | 32.92 | 1653333 | 219494 |
| 120 | 360 | 404 | 402 | 388.67 | 24.85 | 2591111 | 165641 |
| 144 | 450 | 447 | 468 | 455.00 | 11.36 | 3033333 | 75719 |
| 168 | 501 | 444 | 471 | 472.00 | 28.51 | 3146667 | 190088 |
| 192 | 516 | 464 | 496 | 492.00 | 26.23 | 3280000 | 174865 |

TABLE 5

(data underlying FIG. 7D)

| ng/mL | 293S | | | 293 GlycoDelete | | | E. Coli | | |
|---|---|---|---|---|---|---|---|---|---|
| 54 | 0.686 | 0.709 | 0.702 | 0.665 | 0.637 | 0.731 | 0.612 | 0.661 | 0.671 |
| 18 | 0.687 | 0.657 | 0.648 | 0.691 | 0.658 | 0.724 | 0.627 | 0.705 | 0.642 |
| 6 | 0.593 | 0.665 | 0.619 | 0.63 | 0.67 | 0.693 | 0.632 | 0.704 | 0.601 |
| 2 | 0.588 | 0.646 | 0.593 | 0.615 | 0.587 | 0.719 | 0.495 | 0.577 | 0.525 |

TABLE 5-continued (data underlying FIG. 7D)

| ng/mL | 293S | | | 293 GlycoDelete | | | E. Coli | | |
|---|---|---|---|---|---|---|---|---|---|
| 0.6667 | 0.548 | 0.605 | 0.555 | 0.568 | 0.601 | 0.674 | 0.298 | 0.37 | 0.308 |
| 0.2222 | 0.463 | 0.522 | 0.49 | 0.528 | 0.557 | 0.618 | 0.138 | 0.185 | 0.143 |
| 0.0741 | 0.266 | 0.384 | 0.321 | 0.365 | 0.446 | 0.446 | 0.042 | 0.074 | 0.053 |
| 0.0247 | 0.133 | 0.202 | 0.17 | 0.248 | 0.27 | 0.314 | −0.021 | 0.015 | −0.026 |
| 0.008 | 0.048 | 0.076 | 0.068 | 0.142 | 0.132 | 0.156 | −0.056 | −0.042 | −0.069 |
| 0 | −0.07 | −0.088 | −0.082 | −0.057 | −0.102 | −0.059 | −0.081 | −0.084 | −0.101 |

TABLE 6

(data underlying FIG. 7E)

| eT sialidase + galactosidase/ R2 | eT sialidase/ R2 | eT not treated/ R2 | no protein/ R2 | eT sialidase + galactosidase/ R1 | et sialidase/ R1 | eT not treated/ R1 | no protein/ R1 | Antibody dilution | Antibody dilution |
|---|---|---|---|---|---|---|---|---|---|
| 3.5 | 3.5 | 3.5 | 0.276 | 3.5 | 3.5 | 3.5 | 0.396 | 1 | 1 |
| 3.5 | 3.5 | 3.5 | 0.189 | 3.5 | 3.5 | 3.5 | 0.197 | 2 | 2 |
| 3.5 | 3.5 | 3.5 | 0.16 | 3.5 | 3.5 | 3.5 | 0.187 | 4 | 4 |
| 3.5 | 3.5 | 3.5 | 0.195 | 3.5 | 3.5 | 3.5 | 0.218 | 8 | 8 |
| 3.5 | 3.5 | 3.5 | 0.138 | 3.058 | 3.161 | 3.015 | 0.151 | 16 | 16 |
| 3.225 | 3.279 | 3.15 | 0.126 | 2.307 | 2.326 | 2.198 | 0.16 | 32 | 32 |
| 2.789 | 2.754 | 2.695 | 0.144 | 1.564 | 1.554 | 1.462 | 0.166 | 64 | 64 |
| 1.903 | 1.865 | 1.792 | 0.123 | 0.907 | 0.924 | 0.862 | 0.098 | 128 | 128 |
| 1.192 | 1.201 | 1.13 | 0.147 | 0.57 | 0.538 | 0.533 | 0.107 | 256 | 256 |
| 0.723 | 0.746 | 0.69 | 0.106 | 0.332 | 0.353 | 0.363 | 0.08 | 512 | 512 |
| 0.439 | 0.449 | 0.419 | 0.125 | 0.228 | 0.218 | 0.199 | 0.077 | 1024 | 1024 |
| 0.106 | 0.102 | 0.115 | 0.099 | 0.128 | 0.098 | 0.102 | 0.075 | 2048 | 2048 |

TABLE 7

(data underlying FIG. 14C)

| Antibody concentration µg/mL | Anti-CD20 293 | | | Anti-CD20 293 GlycoDelete | | |
|---|---|---|---|---|---|---|
| 10 | 2637.7 | 2563.4 | 2582.8 | 2633.8 | 2599.3 | 2539.1 |
| 2.5 | 2145.8 | 2177.3 | 1924.2 | 2223.5 | 2130.6 | 2250.8 |
| 0.625 | 1501.8 | 1516.7 | 1548.3 | 1434.7 | 1511.5 | 1554.9 |
| 0.15625 | 673.3 | 673.1 | 644 | 602.4 | 662.6 | 667.1 |
| 0.039063 | 240.9 | 234 | 210.2 | 206.7 | 216.2 | 248.7 |
| 0.009766 | 76.4 | 79.7 | 72.2 | 71.5 | 68.2 | 75.9 |
| 0.002441 | 28.6 | 27.5 | 23.2 | 26.8 | 24.6 | 26.9 |
| 0.00061 | 14.1 | 12.3 | 11.3 | 14 | 10 | 19 |

TABLE 8

(data underlying FIG. 14E)

FcγRI

| Ab Concentration µg/ml | GlycoDelete Anti-CD20 | | | 293 Anti-CD20 | | |
|---|---|---|---|---|---|---|
| 50 | 0.315 | 0.324 | 0.317 | 0.085 | 0.091 | 0.084 |
| 10 | 1.163 | 1.153 | 1.143 | 0.143 | 0.143 | 0.141 |
| 2 | 2.418 | 2.324 | 2.324 | 0.388 | 0.379 | 0.377 |
| 0.4 | 3.079 | 2.886 | 2.961 | 1.138 | 1.105 | 1.102 |
| 0.08 | 3.215 | 3.165 | 3.257 | 2.243 | 2.198 | 2.332 |
| 0.016 | 3.389 | 3.339 | 3.387 | 3.049 | 3.036 | 3.156 |
| 0.0032 | 3.379 | 3.443 | 3.344 | 3.394 | 3.397 | 3.437 |
| 0.0006 | 3.474 | 3.589 | 3.506 | 3.428 | 3.598 | 3.602 |

TABLE 8-continued

FcγRIIa

| Antibody Concentration µg/ml | Anti-CD20 293 GlycoDelete | | | Anti-CD20 293 | | |
|---|---|---|---|---|---|---|
| 2.69897 | 1.559 | 2.638 | 2.573 | 0.684 | 0.732 | 0.671 |
| 2.22185 | 2.408 | 2.7 | 2.761 | 1.502 | 1.644 | 1.682 |
| 1.744731 | 2.182 | 2.905 | 2.918 | 2.113 | 2.463 | 2.359 |
| 1.267617 | 2.529 | 3.021 | 3.014 | 2.433 | 2.907 | 2.725 |
| 0.790496 | 2.389 | 2.967 | 3.191 | 2.564 | 2.907 | 2.981 |
| 0.313445 | 2.521 | 3.019 | 3.103 | 2.569 | 2.965 | 2.932 |
| −0.16368 | 2.441 | 2.944 | 3.068 | 2.687 | 3.023 | 3.099 |
| −0.64016 | 2.438 | 3.058 | 3.031 | 2.605 | 2.885 | 2.98 |

(data underlying FIG. 14F)

FcγRIIb

| Antibody Concentration µg/ml | Anti-CD20 293 GlycoDelete | | Anti-CD20 293 | |
|---|---|---|---|---|
| 2300 | 0.962 | 0.84 | | |
| 766.67 | 1.476 | 1.356 | | |
| 255.56 | 1.56 | 1.62 | | |
| 85.19 | 1.769 | 1.678 | | |
| 28.4 | 1.739 | 1.73 | | |
| 9.47 | 1.871 | 1.814 | | |
| 3.16 | 1.899 | 1.827 | | |
| 3000 | | | 0.284 | 0.274 |
| 1000 | | | 0.641 | 0.629 |
| 333.33 | | | 1.061 | 1.098 |
| 111.11 | | | 1.517 | 1.49 |
| 37.04 | | | 1.662 | 1.545 |
| 12.35 | | | 1.991 | 1.874 |
| 4.12 | | | 2.268 | 1.918 |

TABLE 8-continued

ADCC

| Antibody Concentration μg/ml | Anti-CD20 293 GlycoDelete | Anti-CD20 293 |
|---|---|---|
| 2.3 | 52.44 | 50.35 |
| 0.46 | 46.6 | 48.82 |
| 0.092 | 42.04 | 45.15 |
| 0.0184 | 33.85 | 32.4 |
| 0.00368 | 16.5 | 15.22 |
| 0.000736 | 4.52 | 4.43 |
| 0.000147 | 0.26 | −1.11 |
| 2.94E−05 | 1.66 | −0.17 |
| 3 | | 52.14 56.15 |
| 0.6 | | 53.29 49.37 |
| 0.12 | | 51.84 51.42 |
| 0.024 | | 51.76 49.07 |
| 0.0048 | | 43.7 44.64 |
| 0.00096 | | 21.62 21.36 |
| 0.000192 | | 4.26 8.44 |
| 3.84E−05 | | 2.26 1.45 |

TABLE 9

(data underlying FIG. 14F)

| 293SGlycoDelete a-CD20 + galactosidase + sialidase | | | 293SGlycoDelete a-CD20 + sialidase | | | 293SGlycoDelete a-CD20 | | | No protein | | | Antibody dilution |
|---|---|---|---|---|---|---|---|---|---|---|---|---|
| 3.5 | 3.43 | 3.5 | 3.5 | 3.5 | 3.5 | 3.5 | 3.428 | 3.5 | 0.459 | 0.458 | 0.484 | 50 |
| 3.5 | 3.5 | 3.5 | 3.441 | 3.5 | 3.5 | 3.5 | 3.5 | 3.5 | 0.179 | 0.161 | 0.162 | 150 |
| 3.231 | 3.147 | 3.212 | 3.16 | 3.398 | 3.335 | 3.252 | 3.283 | 3.25 | 0.077 | 0.081 | 0.019 | 450 |
| 2.778 | 2.628 | 2.851 | 2.815 | 2.879 | 2.864 | 2.798 | 2.689 | 2.906 | 0.054 | 0.068 | 0.025 | 1350 |
| 1.902 | 1.756 | 1.914 | 1.992 | 2.159 | 2.387 | 1.982 | 1.968 | 2.043 | 0.034 | 0.043 | 0.016 | 4050 |
| 1.048 | 0.931 | 1.024 | 1.09 | 1.281 | 1.308 | 1.07 | 1.045 | 1.188 | 0.02 | 0.049 | 0.013 | 12150 |
| 0.477 | 0.494 | 0.456 | 0.524 | 0.48 | 0.619 | 0.5 | 0.513 | 0.278 | 0.023 | 0.046 | 0.061 | 36450 |
| 0.225 | 0.211 | 0.198 | 0.232 | 0.215 | 0.274 | 0.216 | 0.21 | 0.207 | 0.02 | 0.037 | 0.002 | 109350 |
| 0.121 | 0.103 | 0.085 | 0.116 | 0.1 | 0.186 | 0.109 | 0.138 | 0.081 | 0.02 | 0.021 | 0.001 | 328050 |
| 0.083 | 0.074 | 0.043 | 0.07 | 0.06 | 0.051 | 0.073 | 0.053 | 0.035 | 0.018 | 0.03 | 0.005 | 984150 |

TABLE 10

(data underlying FIG. 14G)

| Time (h) | Anti-CD20 293s | | | | Anti-CD20 293GlycoDelete | | | |
|---|---|---|---|---|---|---|---|---|
| 1 | 16.1974 | 13.17261 | 17.00356 | 11.66813 | 28.8332 | 29.3877 | 33.474 | 36.6924 |
| 24 | 7.4006 | 9.311962 | 8.466237 | 6.55145 | 14.78954 | 16.3589 | 14.10662 | 13.68416 |
| 48 | 7.21618 | 7.227962 | 6.746963 | 7.31205 | 19.8775 | 13.93023 | 15.7465 | 17.25974 |
| 96 | 6.76923 | 8.425325 | 6.122825 | 7.1901 | 12.1798 | 14.31522 | 17.8752 | 14.34155 |
| 168 | 5.17352 | 7.374187 | 5.897713 | 6.8257 | 11.631 | 14.21366 | 11.92079 | 11.60133 |
| 240 | 4.16867 | 3.625075 | 5.712138 | 6.59155 | 11.51135 | 11.86461 | 10.81969 | 11.3477 |
| 336 | 3.88537 | 4.81935 | 4.346875 | 2.606795 | 7.239687 | 10.82754 | 7.92285 | 7.9431 |
| 504 | 3.13270 | 2.52692 | 2.639255 | 2.566235 | 5.357775 | 6.811675 | 5.078675 | 5.5248 |
| 672 | 1.59795 | 1.916417 | 1.99827 | 1.65403 | 3.349695 | 3.54475 | 3.661225 | 3.075095 |

REFERENCES

Alphabetical References

Barb A. W., and J. H. Prestegard. NMR analysis demonstrates immunoglobulin G N-glycans are accessible and dynamic. *Nat. Chem. Biol.* 2011; 7(3):147-53.

Buck P. M., S. Kumar, and S. K. Singh. Consequences of glycan truncation on Fc structural integrity. *MAbs* 2013; 5(6):904-16.

Chen X., Y. D. Liu, and G. C. Flynn. The effect of Fc glycan forms on human IgG2 antibody clearance in humans. *Glycobiology* 2009; 19(3):240-9.

Elliott, S. et al. Control of rHuEPO biological activity: The role of carbohydrate. *Experimental Hematology* 32, 1146-1155 (2004).

Ferrara, C. et al. Modulation of therapeutic antibody effector functions by glycosylation engineering: Influence of Golgi enzyme localization domain and co-expression of heterologous β1, 4-N-acetylglucosaminyltransferase III and Golgi α-mannosidase II. *Biotechnology and Bioengineering* 93, 851-861 (2006).

Huang C. Receptor-Fc fusion therapeutics, traps, and MIMETIBODY technology. *Curr. Opin. Biotechnol.* 2009; 20(6):692-9.

Jefferis R. Glycosylation of natural and recombinant antibody molecules. *Adv. Exp. Med. Biol.* 2005; 564:143-8.

Krapp S., Y. Mimura, R. Jefferis, R. Huber, and P. Sondermann. Structural analysis of human IgG-Fc glycoforms reveals a correlation between glycosylation and structural integrity. *J. Mol. Biol.* 2003; 325(5):979-89.

Lux, A., X. Yu, C. N. Scanlan, and F. Nimmerjahn. Impact of immune complex size and glycosylation on IgG binding to human FcγRs. *J. Immunol.* 190, 4315-4323 (2013).

Millward T. A., M. Heitzmann, K. Bill, U. Langle, P. Schumacher, and K. Forrer. Effect of constant and variable domain glycosylation on pharmacokinetics of therapeutic antibodies in mice. *Biologicals* 2008; 36(1):41-7.

Roopenian, D. C. and S. Akilesh. FcRn: the neonatal Fc receptor comes of age. *Nat. Rev. Immunol.* 7, 715-725 (2007).

Wright A., and S. L. Morrison. Effect of glycosylation on antibody function: implications for genetic engineering. *Trends Biotechnol.* 1997; 15(1):26-32.

Yamaguchi Y., M. Nishimura, M. Nagano, H. Yagi, H. Sasakawa, K. Uchida, K. Shitara, and K. Kato. Glycoform-dependent conformational alteration of the Fc region of human immunoglobulin G1 as revealed by NMR spectroscopy. *Biochim. Biophys. Acta.* 2006; 1760 (4): 693-700.

NUMBERED REFERENCES

1. Ferrara, C. et al. Modulation of therapeutic antibody effector functions by glycosylation engineering: Influence of Golgi enzyme localization domain and co-expression of heterologous β1, 4-N-acetylglucosaminyltransferase III and Golgi α-mannosidase II. *Biotechnology and Bioengineering* 93:851-861 (2006).
2. Li, H. and M. d'Anjou. Pharmacological significance of glycosylation in therapeutic proteins. *Current Opinion in Biotechnology* 20:678-684 (2009).
3. Elliott, S. et al. Control of rHuEPO biological activity: The role of carbohydrate. *Experimental Hematology* 32:1146-1155 (2004).
4. Reeves, P. J., N. Callewaert, R. Contreras, and H. G. Khorana. Structure and function in rhodopsin: High-level expression of rhodopsin with restricted and homogeneous N-glycosylation by a tetracycline-inducible N-acetylglucosaminyltransferase I-negative HEK293S stable mammalian cell line. *PNAS* 99:13419-13424 (2002).
5. Robbins, P. W. et al. Primary structure of the Streptomyces enzyme endo-beta-N-acetylglucosaminidase H. *J. Biol. Chem.* 259:7577-7583 (1984).
6. Stals, I. et al. Identification of a gene coding for a deglycosylating enzyme in Hypocrea jecorina. *FEMS Microbiol. Lett.* 303:9-17 (2010).
7. Paroutis, P., N. Touret, and S. Grinstein. The pH of the Secretory Pathway: Measurement, Determinants, and Regulation. *Physiology* 19:207-215 (2004).
8. Grundmann, U., C. Nerlich, T. Rein, and G. Zettlmeissl. Complete cDNA sequence encoding human beta-galactoside alpha-2,6-sialyltransferase. *Nucleic Acids Res.* 18:667 (1990).
9. Verstraete, K. et al. Structural insights into the extracellular assembly of the hematopoietic Flt3 signaling complex. *Blood* 118:60-68 (2011).
10. Stanley, P. Chinese hamster ovary cell mutants with multiple glycosylation defects for production of glycoproteins with minimal carbohydrate heterogeneity. *Mol. Cell. Biol.* 9:377-383 (1989).
11. Lee, A. S. Coordinated regulation of a set of genes by glucose and calcium ionophores in mammalian cells. *Trends in Biochemical Sciences* 12:20-23 (1987).
12. Hamblin, M. W. and M. A. Metcalf. Primary structure and functional characterization of a human 5-HT1D-type serotonin receptor. *Mol. Pharmacol.* 40:143-148 (1991).
13. Lee, F. et al. Isolation of cDNA for a human granulocyte-macrophage colony-stimulating factor by functional expression in mammalian cells. *PNAS* 82:4360-4364 (1985).
14. Mössner, E. et al. Increasing the efficacy of CD20 antibody therapy through the engineering of a new type II anti-CD20 antibody with enhanced direct and immune effector cell-mediated B-cell cytotoxicity. *Blood* 115: 4393-4402 (2010).
15. Forno, G. et al. N- and O-linked carbohydrates and glycosylation site occupancy in recombinant human granulocyte-macrophage colony-stimulating factor secreted by a Chinese hamster ovary cell line. *Eur. J. Biochem.* 271:907-919 (2004).
16. Crispin, M. et al. Inhibition of hybrid- and complex-type glycosylation reveals the presence of the GlcNAc transferase I-independent fucosylation pathway. *Glycobiology* 16:748-756 (2006).
17. Ericsson, U. B., B. M. Hallberg, G. T. DeTitta, N. Dekker, and P. Nordlund. Thermofluor-based high-throughput stability optimization of proteins for structural studies. *Anal. Biochem.* 357:289-298 (2006).
18. Kitamura, T. et al. Establishment and characterization of a unique human cell line that proliferates dependently on GM-CSF, IL-3, or erythropoietin. *J. Cell. Physiol.* 140: 323-334 (1989).
19. Nallet, S. et al. Glycan variability on a recombinant IgG antibody transiently produced in HEK-293E cells. *New Biotechnology* 29:471-476 (2012).
20. Jefferis, R. Glycosylation as a strategy to improve antibody-based therapeutics. *Nature Reviews Drug Discovery* 8:226-234 (2009).
21. Tradtrantip, L., J. Ratelade, H. Zhang, and A. S. Verkman. Enzymatic deglycosylation converts pathogenic neuromyelitis optica anti-aquaporin-4 immunoglobulin G into therapeutic antibody. *Annals of Neurology* 73:77-85 (2013).
22. Nandakumar, K. S. et al. Dominant suppression of inflammation by glycan-hydrolyzed IgG. *PNAS* (2013). doi:10.1073/pnas.1301480110
23. Allhorn, M. and M. Collin. Sugar-free Antibodies—The Bacterial Solution to Autoimmunity? *Annals of the New York Academy of Sciences* 1173:664-669 (2009).
24. Graham, F. L. and A. J. van der Eb. A new technique for the assay of infectivity of human adenovirus 5 DNA. *Virology* 52:456-467 (1973).
25. MacLean, B. et al. Skyline: an open source document editor for creating and analyzing targeted proteomics experiments. *Bioinformatics* 26:966-968 (2010).
26. Tada, H., O. Shiho, K. Kuroshima, M. Koyama, and K. Tsukamoto. An improved colorimetric assay for interleukin 2. *J. Immunol. Methods* 93:157-165 (1986).
27. Magistrelli, G. et al. Robust recombinant FcRn production in mammalian cells enabling oriented immobilization for IgG binding studies. *J. Immunol. Methods* 375:20-29 (2012).
28. Anonymous. Biosimilar, biobetter and next generation therapeutic antibodies. *MAbs* 3, 107-110 (2011).

ADDITIONAL REFERENCES FOR METHODS SECTION

1. Fenteany, F. H. and K. J. Colley. Multiple signals are required for alpha2,6-sialyltransferase (ST6Gal I) oligomerization and Golgi localization. *J. Biol. Chem.* 280: 5423-5429 (2005).
2. Stanley, P. Chinese hamster ovary cell mutants with multiple glycosylation defects for production of glycoproteins with minimal carbohydrate heterogeneity. *Mol. Cell. Biol.* 9:377-383 (1989).
3. Stals, I. et al. Identification of a gene coding for a deglycosylating enzyme in Hypocrea jecorina. *FEMS Microbiol. Lett.* 303:9-17 (2010).

4. Grundmann, U., C. Nerlich, T. Rein, and G. Zettlmeissl. Complete cDNA sequence encoding human beta-galactoside alpha-2,6-sialyltransferase. *Nucleic Acids Res.* 18:667 (1990).
5. Nagata, Y. et al. Expression cloning of beta 1,4 N-acetyl-galactosaminyltransferase cDNAs that determine the expression of GM2 and GD2 gangliosides. *J. Biol. Chem.* 267:12082-12089 (1992).
6. Laroy, W., R. Contreras, and N. Callewaert. Glycome mapping on DNA sequencing equipment. *Nat. Protoc.* 1:397-405 (2006).
7. Lockstone, H. E. Exon array data analysis using Affymetrix power tools and R statistical software. *Brief Bioinformatics* 12:634-644 (2011).
8. Smyth, G. K. Linear Models and Empirical Bayes Methods for Assessing Differential Expression in Microarray Experiments. *Statistical Applications in Genetics and Molecular Biology* 3 (2004).
9. Schägger, H. Tricine-SDS-PAGE. *Nat. Protoc.* 1:16-22 (2006).
10. Gasteiger, E. et al. in *The Proteomics Protocols Handbook* (Walker, J. M.) 571-607 (Humana Press, 2005).

The invention claimed is:

1. A plurality of Fc-containing molecules:
wherein the Fc-containing molecules are glycosylated on N297 of the Fc part,
wherein the glycosylation on N297 of the Fc part consists of one or more glycans selected from the group consisting of a trisaccharide structure Neu5Ac-Hex-HexNAc, disaccharide structure Hex-HexNAc, and a monosaccharide structure HexNAc; and
wherein at least one of the plurality of Fc-containing molecules comprises a glycan that is not a monosaccharide structure HexNAc; and
wherein the plurality of Fc-containing molecules have reduced affinity for Fc-gamma receptors as compared to Fc-containing molecules with wild-type glycosylation of N297.

2. The plurality of Fc-containing molecules of claim 1, wherein the Fc-containing molecules of the plurality are identical.

3. The plurality of Fc-containing molecules of claim 1, wherein the trisaccharide structure is Neu5Ac-α-2,3-Gal-β-1,4-GlcNAc, the disaccharide structure is Gal-β-1,4-GlcNAc, and the monosaccharide structure is GlcNAc.

4. The plurality of Fc-containing molecules of claim 1, wherein the Fc-containing molecules are antibodies.

5. The plurality of Fc-containing molecules of claim 2, wherein the Fc-containing molecules are antibodies.

6. The plurality of Fc-containing molecules of claim 3, wherein the Fc-containing molecules are antibodies.

7. A medicament comprising:
the plurality of Fc-containing molecules of claim 1.

8. A medicament comprising:
the plurality of Fc-containing molecules of claim 2.

9. A medicament comprising:
the plurality of Fc-containing molecules of claim 3.

10. A medicament comprising:
the plurality of Fc-containing molecules of claim 4.

11. A medicament comprising:
the plurality of Fc-containing molecules of claim 5.

12. A medicament comprising:
the plurality of Fc-containing molecules of claim 6.

13. A method of increasing circulation time of an Fc-containing molecule, without altering antigen binding, in a subject in need thereof, the method comprising:
administering the plurality of Fc-containing molecules of claim 1 to the subject.

14. A plurality of IgG antibodies comprising glycosylation on N297 of the Fc part thereof wherein the glycosylation on N297 comprises:
a trisaccharide structure that is Neu5Ac-α-2,3-Gal-β-1,4-GlcNAc;
a disaccharide structure that is Gal-β-1,4-GlcNAc;
a monosaccharide structure that is GlcNAc; and
wherein the plurality of IgG antibodies have a significantly increased circulation half-life as compared to IgG antibodies with wild-type glycosylation of N297.

15. The antibody of claim 14, wherein the plurality of IgG antibodies is a plurality of $IgG_1$ antibodies.

* * * * *

SEQUENCE LISTING

```
<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: Peptide from fc chain

<400> SEQUENCE: 1

Glu Gln Gln Tyr Asn Ser Thr Tyr Arg
1               5

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
aacaaggacg tacccgttaa agaactgca                                        29

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
cgcgagcacc gtacccgtta aagaactgca                                       30

<210> SEQ ID NO 4
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(28)
<223> OTHER INFORMATION: n is a, c, g, or t

<400> SEQUENCE: 4
ctcgagatgg tacccgttaa agaactcnag ttgagagc                              38

<210> SEQ ID NO 5
<211> LENGTH: 72
<212> TYPE: DNA
<213> ORGANISM: Artificial Sequence
<220> FEATURE:
<223> OTHER INFORMATION: Primer

<400> SEQUENCE: 5
```

```
gcacctgagg ttacagatct tcttcagaaa taagcttttg ttcagcgtta accatagcgt    60
agtagttgat gg                                                       72

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
gcactcgaga tgattcacac caacctgaag a                                  31

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
ttaacgggta cgtccttgtt ccacacctg                                     29

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
gcactcgaga tgtggctggg ccgccggg                                      28

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
ttaacgggta cggtgctcgc gtacaggagc c                                  31

<210> SEQ ID NO 10
<211> LENGTH: 63
<212> TYPE: DNA
<213> ORGANISM: Artificial Sequence
<220> FEATURE:
<223> OTHER INFORMATION: Primer

<400> SEQUENCE: 10
tcgagatgaa gactatcatt gctttgagct acattttctg tctggtttgg gcccaagacg    60
tac                                                                 63

<210> SEQ ID NO 11
<211> LENGTH: 55
<212> TYPE: DNA
<213> ORGANISM: Artificial Sequence
<220> FEATURE:
<223> OTHER INFORMATION: Primer

<400> SEQUENCE: 11
gtcttgggcc caaaccagac agaaaatgta gctcaaagca atgatagtct tcatc         55
```

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtgctgctcc tggttctttc                                        20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tcagccatag aaccgaaacc                                        20

<210> SEQ ID NO 14
<211> LENGTH: 58
<212> TYPE: DNA
<213> ORGANISM: Artificial Sequence
<220> FEATURE:
<223> OTHER INFORMATION: Primer

<400> SEQUENCE: 14
ctagaattcg cgatatcccg ggcccagcgc tgcggccgct cgagctagcg tttaaact    58

<210> SEQ ID NO 15
<211> LENGTH: 58
<212> TYPE: DNA
<213> ORGANISM: Artificial Sequence
<220> FEATURE:
<223> OTHER INFORMATION: Primer

<400> SEQUENCE: 15
gatcagttta aacgctagct cgagcggccg cagcgctggg cccgggatat cgcgaatt    58

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
gcagtcgacc atgtccccac tgaaccagtc agc                         33

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
gcagcggccg cggaggcctt ccggaaaggg ac                          32

<210> SEQ ID NO 18
<211> LENGTH: 55
<212> TYPE: DNA
<213> ORGANISM: Artificial Sequence
<220> FEATURE:
<223> OTHER INFORMATION: Primer

```
<400> SEQUENCE: 18
aaacttaggc gggagccacc tggctggtct cagtactggc cttccggaaa gggac        55

<210> SEQ ID NO 19
<211> LENGTH: 41
<212> TYPE: DNA
<213> ORGANISM: Artificial Sequence
<220> FEATURE:
<223> OTHER INFORMATION: Primer

<400> SEQUENCE: 19
ctcccgccta agtttaaacg tttaacccgg gtaaattccg c                      41

<210> SEQ ID NO 20
<211> LENGTH: 43
<212> TYPE: DNA
<213> ORGANISM: Artificial Sequence
<220> FEATURE:
<223> OTHER INFORMATION: Primer

<400> SEQUENCE: 20
gattatgatc agtttaaaca ctagtaaatt ctagagtcgc ggc                    43

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
ctcaagggcc ccttgacc                                                18

<210> SEQ ID NO 22
<211> LENGTH: 50
<212> TYPE: DNA
<213> ORGANISM: Artificial Sequence
<220> FEATURE:
<223> OTHER INFORMATION: Primer

<400> SEQUENCE: 22
cgagcagaat tcaatggtga tgatggtgat gctcctggac tggctcccag              50

<210> SEQ ID NO 23
<211> LENGTH: 4
<212> TYPE: PRT
<213> ORGANISM: Artificial Sequence
<220> FEATURE:
<223> OTHER INFORMATION: Carboxy-terminal tetrapeptide

<400> SEQUENCE: 23

Lys Asp Glu Leu
1

<210> SEQ ID NO 24
<211> LENGTH: 4
<212> TYPE: PRT
<213> ORGANISM: Artificial Sequence
<220> FEATURE:
<223> OTHER INFORMATION: Carboxy-terminal tetrapeptide

<400> SEQUENCE: 24

His Asp Glu Leu
1
```

```
<210> SEQ ID NO 25
<211> LENGTH: 28
<212> TYPE: PRT
<213> ORGANISM: Homo sapiens

<400> SEQUENCE: 25

Asp Thr Ala Ala Glu Met Asn Glu Thr Val Glu Val Ile Ser Glu Met
1               5                   10                  15

Phe Asp Leu Gln Glu Pro Thr Cys Leu Gln Thr Arg
            20                  25
```